United States Patent [19]

Fukumi et al.

[11] Patent Number: 5,362,725
[45] Date of Patent: Nov. 8, 1994

[54] TETRACYCLIC COMPOUNDS HAVING ANTI-ALLERGIC AND ANTI-ASTHMATIC ACTIVITIES AND THEIR USE

[75] Inventors: Hiroshi Fukumi; Toshiaki Sakamoto; Mitsuo Sugiyama; Yoshio Iizuka; Takeshi Yamaguchi, all of Hiromachi, Japan

[73] Assignee: Sankyo Company, Limited, Tokyo, Japan

[21] Appl. No.: 962,037

[22] Filed: Oct. 15, 1992

Related U.S. Application Data

[63] Continuation of Ser. No. 592,279, Oct. 3, 1990, abandoned.

[30] Foreign Application Priority Data

Oct. 5, 1989 [JP] Japan ................... 1-260592
Mar. 29, 1990 [JP] Japan ................... 2-81513

[51] Int. Cl.$^5$ ................... C07D 487/04; A61K 31/55
[52] U.S. Cl. ................... 514/214; 540/578; 540/579; 514/826
[58] Field of Search ................... 540/579; 514/214

[56] References Cited

U.S. PATENT DOCUMENTS

| | | | |
|---|---|---|---|
| 4,025,513 | 5/1977 | Olivie ................... | 544/343 |
| 4,062,848 | 12/1977 | van der Burg ................... | 514/250 |
| 4,217,452 | 8/1980 | Olivie ................... | 544/343 |
| 4,271,073 | 6/1981 | Beuder et al. ................... | 544/343 |

FOREIGN PATENT DOCUMENTS 0001585  5/1979  European Pat. Off. .
2614406  10/1976  Germany .
WO88/07997  10/1988  WIPO .

OTHER PUBLICATIONS

Ciba–Geigy A–G. Chem. Abst. 92-6566k (1980).
Copp et al., CA 110-95281 u (1989).
Van der Burg, CA 86-29883b (1977).

*Primary Examiner*—Mark L. Berch
*Assistant Examiner*—Philip I. Datlow
*Attorney, Agent, or Firm*—Frishauf, Holtz, Goodman & Woodward

[57] ABSTRACT

Compounds of formula (I):

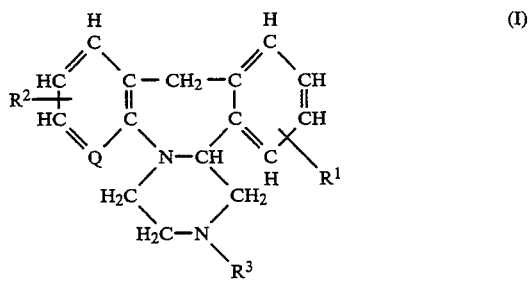

in which: Q is nitrogen or =CH—; $R^1$ and $R^2$ are hydrogen, alkyl, alkoxy, hydroxy, trifluoromethyl or halogen; and $R^3$ is a substituted alkyl groups or a pharmaceutically acceptable salt thereof have valuable anti-allergic and anti-asthmatic activities. The compounds are prepared by reacting a corresponding compound where $R^3$ is replaced by a hydrogen atom with a compound to introduce the group $R^3$.

58 Claims, No Drawings

TETRACYCLIC COMPOUNDS HAVING ANTI-ALLERGIC AND ANTI-ASTHMATIC ACTIVITIES AND THEIR USE

This application is a continuation of application Ser. No. 07/592,279, filed Oct. 3, 1990, now abandoned.

BACKGROUND TO THE INVENTION

The present invention relates to a new series of tetracyclic compounds having two or three ring nitrogen atoms, which we have found to have valuable anti-allergic and anti-asthmatic activities, and provides methods and compositions using them, as well as processes for their preparation.

The compounds of the present invention may be generally described as dibenzo-pyrazino-azepine or benzo-pyrido-pyrazino-azepine derivatives. Certain compounds of this type are known. For example, mianserin, which has the formula (A):

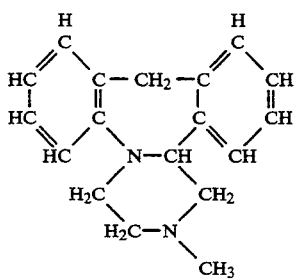

mirtazapine, which has the formula (B):

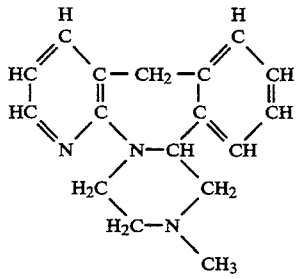

aptazapine, which has the formula (C):

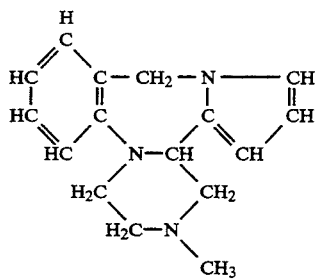

2-(2-hydroxyethyl)-1,3,4,14b-tetrahydro-2H, 10H-pyrazino[1,2-a]pyrrolo[2,1-c][1,4]benzodiazepine, which has the formula (D):

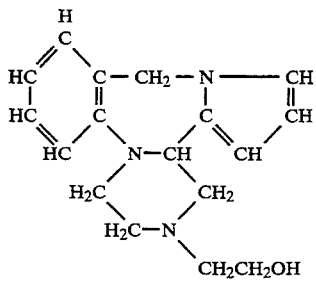

2-methoxycarbonylmethyl-1,3,4,14b-tetrahydro-2H, 10H-pyrazino[1, 2-a]pyrrolo[2,1-c][1,4]benzodiazepine, which has the formula (E):

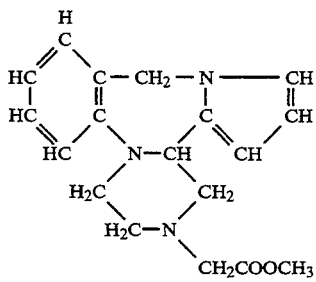

and 2-(2-carboxamidoethyl)-1,2,3,4,10,14b-hexahydrodibenzo[c,f]pyrazino[1,2-a]azepine, which has the formula (F):

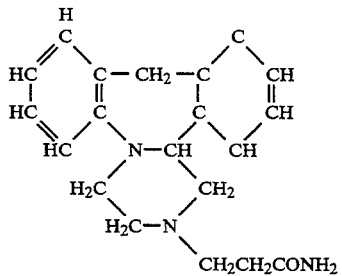

are disclosed in U.S. Pat. No. 4,025,513, U.S. Pat. No. 4,062,848, European Patent Specification No. 1585 and PCT Application No. WO-88/07997, and are said to have various activities, including anti-depressant activity and anti-histamine activity.

The compounds referred to above which are said to possess an anti-allergic activity have been found to be not entirely satisfactory, in that the intensity of the activity is less than would be desired for a useful commercial product, and side effects, such as irritation or depression of the central nervous system, often occur. It would, therefore, be desirable to develop therapeutic agents which, whilst possessing excellent anti-histamic, anti-allergic and anti-asthmatic activities, also have no substantial adverse reactions, such as depression or irritation of the central nervous system.

We have now discovered a series of tetracyclic compounds which fulfil these various desiderata.

BRIEF SUMMARY OF INVENTION

It is, therefore, an object of the invention to provide a series of new dibenzo-pyrazino-azepine and benzo-pyrido-pyrazino-azepine derivatives.

It is a further, and more specific, object of the invention to provide certain such compounds which have anti-histamic and/or anti-allergic and/or anti-asthmatic activities.

It is a still further, and more specific, object of the invention to provide certain such compounds which have excellent anti-histamic, anti-allergic and anti-asthmatic activities without such adverse reactions as inducing drowsiness, and which, moreover, exhibit an inhibitory effect on the production of SRS-A (slow reacting substance of anaphylaxis).

It is a further object of the invention to provide methods and compositions using these compounds.

Other objects and advantages will become apparent as the description proceeds.

The compounds of the present invention are those compounds of formula (I):

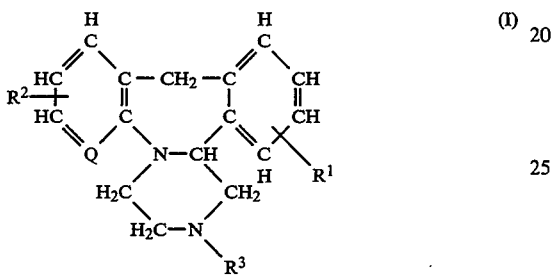

in which:

Q represents a nitrogen atom or a group of formula =CH—;

$R^1$ and $R^2$ are independently selected from the group consisting of hydrogen atoms, alkyl groups having from 1 to 6 carbon atoms, alkoxy groups having from 1 to 6 carbon atoms, hydroxy groups, trifluoromethyl groups and halogen atoms;

$R^3$ represents:

a substituted alkyl group having from 3 to 7 carbon atoms and having at least one substituent selected from the group consisting of hydroxy groups and groups of formula —COOR$^4$, where R$^4$ represents a hydrogen atom, an alkyl group having from 1 to 6 carbon atoms, an aryl group, as defined below, or an aralkyl group, as defined below;

a group of formula —B—O—D—OR$^4$, where: B represents an alkylene or alkylidene group having from 2 to 4 carbon atoms; D represents an alkylene or alkylidene group having from 2 to 7 carbon atoms or such an alkylene or alkylidene group in which the carbon chain is interrupted by 1 or 2 oxygen atoms; and R$^4$ is as defined above;

a group of formula —E—O—G—COOR$^4$, where: E represents an alkylene or alkylidene group having from 2 to 7 carbon atoms; G represents a direct carbon-carbon single bond, an alkylene or alkylidene group having from 1 to 9 carbon atoms or such an alkylene or alkylidene group in which the carbon chain is interrupted by 1 or 2 oxygen atoms, said alkylene or alkylidene group being unsubstituted or being substituted by an aryl group; and R$^4$ is as defined above;

a group of formula —E—O—G—CONR$^5$R$^6$, where: E and G are as defined above; and R$^5$ and R$^6$ are independently selected from the group consisting of hydrogen atoms, unsubstituted alkyl groups having from 1 to 6 carbon atoms, substituted alkyl groups which have from 1 to 6 carbon atoms and which have at least one substituent selected from the group consisting of substituents (a), defined below, cycloalkyl groups which have from 3 to 7 ring carbon atoms and which are unsubstituted or have at least one substituent selected from the group consisting of alkyl groups having from 1 to 4 carbon atoms, aryl groups, as defined below, and aralkyl groups, as defined below;

or R$^5$ and R$^6$ together with the nitrogen atom to which they are attached, represent a cyclic amino group having from 3 to 6 ring atoms, of which one is said nitrogen atom, 0 or 1 is an additional hetero-atom selected from the group consisting of nitrogen, oxygen and sulfur hetero-atoms and the remainder are carbon atoms, said heterocyclic group being unsubstituted or being substituted by at least one substituent selected from the group consisting of substituents (c), defined below; or a group of formula —J—CH(OH)—CH$_2$R$^7$, where: J represents an alkylene or alkylidene group having from 1 to 4 carbon atoms; and R$^7$ represents a hydroxy group, a halogen atom or a group of formula —NR$^5$R$^6$, where R$^5$ and R$^6$ are as defined above;

said aralkyl groups are alkyl groups having from 1 to 4 carbon atoms, which are substituted by from 1 to 3 aryl groups, as defined below;

said aryl groups have from 6 to 10 ring carbon atoms and are unsubstituted or have at least one substituent selected from the group consisting of substituents (b), defined below;

substituents (a):

amino groups; alkylamino groups in which the alkyl group has from 1 to 6 carbon atoms; dialkylamino groups in which each alkyl group is independently selected from the group consisting of alkyl groups having from 1 to 6 carbon atoms; and cyclic amino groups having from 3 to 6 ring atoms, of which one is a nitrogen atom, 0 or 1 is an additional hetero-atom selected from the group consisting of nitrogen, oxygen and sulfur hetero-atoms and the remainder are carbon atoms, said heterocyclic group being unsubstituted or being substituted by at least one substituent selected from the group consisting of substituents (c), defined below;

substituents (b):

alkyl groups having from 1 to 6 carbon atoms; alkoxy groups having from 1 to 6 carbon atoms; aryl groups, as defined above, provided that they are not themselves substituted by aryl groups; and halogen atoms;

substituents (c):

alkyl groups having from 1 to 4 carbon atoms; aryl groups, as defined above; and aralkyl groups, as defined above;

and pharmaceutically acceptable salts thereof.

The invention also provides a pharmaceutical composition for the treatment or prophylaxis of asthma and allergies, which comprises an effective amount of an active compound in admixture with a pharmaceutically acceptable carrier or diluent, wherein the active compound is at least one compound of formula (I) or a pharmaceutically acceptable salt thereof, as defined above.

The invention still further provides a method for the treatment or prophylaxis of asthma or allergies in a mammal, which may be human, suffering from or susceptible to asthma or allergies, which method comprises administering to said mammal an effective amount of an active compound, wherein the active compound is at least one compound of formula (I) or a pharmaceutically acceptable salt thereof, as defined above.

The invention also provides processes for preparing the compounds of the present invention, which are described in more detail hereafter.

DETAILED DESCRIPTION OF INVENTION

In the compounds of the present invention, where $R^1$, $R^2$, $R^4$, $R^5$, $R^6$, substituent (b) or the alkyl group of the alkylamino or dialkylamino group included in substituent (a) represents an alkyl group, this may be a straight or branched chain alkyl group having from 1 to 6 carbon atoms. Examples of such groups include the methyl, ethyl, propyl, isopropyl, butyl, isobutyl, sec-butyl, t-butyl, pentyl, isopentyl, t-pentyl, neopentyl, hexyl and isohexyl groups. Of these, the alkyl groups having from 1 to 4 carbon atoms are preferred.

Where $R^1$ $R^2$, or substituent (b) represents an alkoxy group, this may be a straight or branched chain alkoxy group having from 1 to 6 carbon atoms. Examples of such groups include the methoxy, ethoxy, propoxy, isopropoxy, butoxy,-isobutoxy, sec-butoxy, t-butoxy, pentyloxy, isopentyloxy, t-pentyloxy, neopentyloxy, hexyloxy and isohexyloxy groups. Of these, the alkoxy groups having from 1 to 4 carbon atoms are preferred.

Where $R^1$, $R^2$, $R^7$ or substituent (b) represents a halogen atom, this may be a fluorine, chlorine, bromine or iodine atom, and is preferably a fluorine or chlorine atom.

Where $R^3$ represents a substituted alkyl group having from 3 to 7 carbon atoms, this has at least one substituent selected from the group consisting of hydroxy groups and groups of formula —COOR$^4$, where $R^4$ represents a hydrogen atom, an alkyl group having from 1 to 6 carbon atoms (as exemplified above), an aryl group, or an aralkyl group, preferably a hydrogen atom or an alkyl group having from 1 to 4 carbon atoms. The alkyl group of $R^3$ may be a straight or branched chain alkyl group having from 3 to 7 carbon atoms. Examples of such groups include the propyl, isopropyl, butyl, isobutyl, sec-butyl, t-butyl, pentyl, isopentyl, t-pentyl, neopentyl, hexyl, isohexyl and heptyl groups. Of these, the alkyl groups having from 3 to 5 carbon atoms are preferred, especially straight chain groups having 3 or 5 carbon atoms.

Examples of aryl groups which may be represented by $R^4$, $R^5$ or $R^6$ or may be the substituent on the alkylene or alkylidene group represented by G are aryl groups having from 6 to 10 ring atoms and which are unsubstituted or have at least one substituent selected from the group consisting of substituents (b), as defined and exemplified above. Suitable unsubstituted groups include the phenyl, α-naphthyl and β-naphthyl groups, Of which the phenyl group is preferred. Where the group is substituted, there is, in principle, no limitation on the number of substituents, except such as may be dictated by the number of substitutable positions and possibly by steric constraints; hence, the maximum number of substituents on a phenyl group would be 5, whilst the maximum number on a naphthyl group would be 7. However, in practice, a maximum of 3 substituents is generally preferred, and these are selected from substituents (b), i.e. alkyl groups, alkoxy groups, aryl groups and halogen atoms, all as exemplified above, of which we prefer a methyl group, a methoxy group, a fluorine atom or a chlorine atom. Examples of substituted aryl groups include the 4-chlorophenyl, 3-chlorophenyl, 2-chlorophenyl, 4-fluorophenyl, 3-fluorophenyl, 2-fluorophenyl, 4-methylphenyl, 3-methylphenyl, 2-methylphenyl, 4-methoxyphenyl, 3-methoxyphenyl, 2-methoxyphenyl and biphenyl groups.

The aralkyl groups which may be represented by $R^4$, $R^5$ or $R^6$ are alkyl groups which have from 1 to 4 carbon atoms, which may be straight or branched chain alkyl groups, and which have from 1 to 3, preferably 1 or 2 and most preferably 3, aryl substituents. The aryl substituents may be any of the aryl groups, substituted or unsubstituted, exemplified above, and the alkyl groups may be any of those alkyl groups having from 1 to 4 carbon atoms exemplified above in relation to $R^1$ etc. Examples of unsubstituted aralkyl groups include the benzyl, phenethyl, 1-phenylethyl, 3-phenylpropyl, 2-phenylpropyl, 1 -phenylpropyl, 1-methyl-2-phenylethyl, 4-phenylbutyl, 3-phenylbutyl, 2-phenylbutyl, 1-phenylbutyl, diphenylmethyl (i.e. benzhydryl), α-naphthylmethyl, β-naphthylmethyl, 2- (α-naphthyl) ethyl, 2- (β-naphthyl)ethyl, di-β-naphthylmethyl, di-α-naphthylmethyl and trityl (i.e. triphenylmethyl) groups, of which we prefer the benzyl and benzhydryl groups. Examples of substituted aralkyl groups include the unsubstituted groups exemplified above, but in which the aryl group is replaced by one of the substituted aryl groups exemplified above, especially the 4-methoxybenzyl, 3-methoxybenzyl, 2-methoxybenzyl, 4-methylbenzyl, 3-methylbenzyl, 2-methylbenzyl, 4-chlorobenzyl, 3-chlorobenzyl, 2-chlorobenzyl, p,p'-difluorobenzhydryl, p-fluorobenzhydryl and p-chlorobenzhydryl groups, preferably the p-chlorobenzhydryl and p,p'-difluorobenzhydryl groups.

Where B represents an alkylene or alkylidene group having from 2 to 4 carbon atoms, this may be a straight or branched chain group having from 2 to 4 carbon atoms, and the "free" valencies may be on the same carbon atom (in which case the group is often referred to as "an alkylidene" group) or on different carbon atoms (often referred to as "an alkylene" group); for the avoidance of doubt, it should be noted that alkylidene and alkylene groups are often colloquially referred to collectively as "alkylene groups". Examples of such groups include the ethylene, trimethylene, 1-methylethylene, 2-methylethylene (propylene), tetramethylene, 1-, 2- and 3- methyltrimethylene, 1- and 2-ethylethylene, ethylidene, propylidene, isopropylidene and butylidene groups, of which the straight chain alkylene groups are preferred, and the ethylene and trimethylene groups are more preferred.

Where D represents an alkylene or alkylidene group having from 2 to 7 carbon atoms, this may be a straight or branched chain group having from 2 to 7 carbon atoms, and the "free" valencies may be on the same carbon atom or on different carbon atoms. Examples of such groups include the ethylene, trimethylene, 1-methylethylene, 2-methylethylene (propylene), tetramethylene, 1-, 2- and 3- methyltrimethylene, 1- and 2-ethylethylene, ethylidene, propylidene, isopropylidene, butylidene, pentamethylene, pentylidene, 1-, 2-, 3- and 4- methyltetramethylene, 1-, 2- and 3- ethyltrimethylene, 1- and 2- propylethylene, 1- and 2- isopropylethylene, hexamethylene, hexylidene, 1-, 2-, 3-, 4- and 5- methylpentamethylene, 1-, 2-, 3- and 4- ethyltetramethylene, 1-, 2- and 3- propyltrimethylene, 1-, 2- and 3-isopropyltrimethylene, 1- and 2- butylethylene, heptylidene, heptamethylene, 1-, 2-, 3-, 4-, 5- and 6-methylhexamethylene, 1-, 2-, 3-, 4- and 5- ethylpentamethylene, 1-, 2-, 3- and 4- propyltetramethylene, 1-, 2- and 3- butyltrimethylene, and 1- and 2- pentylethylene groups, of which the straight chain alkylene groups are preferred, and the ethylene and trimethylene groups are more preferred.

The group represented by D may be a simple carbon chain or it may be interrupted by 1 or 2 oxygen atoms. Examples of such oxygen-containing groups include those groups listed above but in which the carbon chain is interrupted by 1 or 2 oxygen atoms, such as the methyleneoxymethylene, ethyleneoxymethylene, methyleneoxyethylene, ethyleneoxyethylene, ethyleneoxytrimethylene, propyleneoxymethylene, trimethyleneoxymethylene, tetramethyleneoxymethylene, methyleneoxymethyleneoxymethylene, methyleneoxyethyleneoxymethylene, ethyleneoxyethyleneoxymethylene, ethyleneoxymethyleneoxymethylene, methyleneoxyethyleneoxyethylene, ethyleneoxyethyleneoxyethylene, ethyleneoxymethyleneoxyethylene, ethyleneoxyethyleneoxytrimethylene and methyleneoxymethyleneoxytrimethylene groups, of which the ethyleneoxyethylene and ethyleneoxyethyleneoxyethylene groups are preferred.

E represents an alkylene or alkylidene group having from 2 to 7 carbon atoms, and examples of such groups include the alkylene and alkylidene groups exemplified above in relation to the same groups which may be represented by D, preferably an alkylene group having from 2 to 6 carbon atoms, and more preferably an alkylene group having from 2 to 4 carbon atoms.

G represents a direct carbon-carbon single bond, an alkylene or alkylidene group having from 1 to 9 carbon atoms or such an alkylene or alkylidene group in which the carbon chain is interrupted by 1 or 2 oxygen atoms, said alkylene or alkylidene group being unsubstituted or being substituted by an aryl group. Where G represents an alkylene or alkylidene group, this may be a straight or branched chain group having from 1 to 9 carbon atoms, and the "free" valencies may be on the same carbon atom or on different carbon atoms. Examples of such groups include the methylene, ethylene, trimethylene, 1- methylethylene, 2- methylethylene (propylene), tetramethylene, 1-, 2- and 3- methyltrimethylene, 1- and 2- ethylethylene, ethylidene, propylidene, isopropylidene, butylidene, pentamethylene, pentylidene, 1-, 2-, 3- and 4- methyltetramethylene, 1-, 2- and 3- ethyltrimethylene, 1- and 2- propylethylene, 1- and 2- isopropylethylene, hexamethylene, hexylidene, 1 -, 2-, 3-, 4- and 5- methylpentamethylene, 1-, 2-, 3- and 4- ethyltetramethylene, 1-, 2- and 3- propyltrimethylene, 1-, 2- and 3- isopropyltrimethylene, 1- and 2-butylethylene, heptylidene, heptamethylene, 1-, 2-, 3-, 4-, 5- and 6-methylhexamethylene, 1-, 2-, 3-, 4- and 5- ethylpentamethylene, 1-, 2-, 3- and 4- propyltetramethylene, 1-, 2- and 3- butyltrimethylene, 1- and 2- pentylethylene, octamethylene, octylidene, 1 -, 2-, 3-, 4-, 5-, 6- and 7- methylheptamethylene, 1-, 2-, 3-, 4-, 5- and 6- ethylhexamethylene, 1-, 2-, 3-, 4- and 5- propylpentamethylene, 1-, 2-, 3- and 4- butyltetramethylene, 1-, 2- and 3- pentyltrimethylene, 1- and 2- hexylethylene, nonamethylene, nonylidene, 1 -, 2-, 3 -, 4-, 5-, 6-, 7- and 8- methyloctamethylene, 1-, 2-, 3-, 4-, 5-, 6- and 7- ethylheptamethylene, 1-, 2-, 3-, 4-, 5- and 6- propylhexamethylene, 1-, 2-, 3-, 4- and 5- butylpentamethylene, 1-, 2-, 3- and 4- pentyltetramethylene, 1-, 2- and 3- hexyltrimethylene and 1- and 2- heptylethylene groups, of which the alkylene groups having from 1 to 4 carbon atoms are preferred and the methylene and ethylene groups are most preferred.

Where G represents an alkylene or alkylidene group in which the carbon chain is interrupted by 1 or 2 oxygen atoms, this may be a methyleneoxymethylene, ethyleneoxymethylene, methyleneoxyethylene, ethyleneoxyethylene, ethyleneoxytrimethylene, propyleneoxymethylene, trimethyleneoxymethylene, tetramethyleneoxymethylene, methyleneoxymethyleneoxymethylene, methyleneoxyethyleneoxymethylene, ethyleneoxyethyleneoxymethylene, ethyleneoxymethyleneoxymethylene, methyleneoxyethyleneoxyethylene, ethyleneoxyethyleneoxyethylene, ethyleneoxymethyleneoxyethylene, ethyleneoxyethyleneoxytrimethylene, methyleneoxymethyleneoxytrimethylene, tetramethyleneoxytetramethylene, tetramethyleneoxytetramethyleneoxymethylene, trimethyleneoxytetramethylene, pentamethyleneoxytetramethylene, trimethyleneoxytrimethyleneoxytrimethylene, ethyleneoxyethyleneoxypentamethylene or pentamethyleneoxyethyleneoxyethylene group, of which the ethyleneoxymethylene, ethyleneoxyethylene, ethyleneoxyethyleneoxymethylene and ethyleneoxyethyleneoxyethylene groups are preferred and the ethyleneoxymethylene and ethyleneoxyethyleneoxymethylene groups are more preferred.

Where G represents an alkylene or alkylidene group or such a group whose carbon chain is interrupted by one or two oxygen atoms, it may also optionally be substituted by an aryl group, which may be as defined and exemplified above, and the alkylene or alkylidene group may be any of those exemplified above. Examples of such substituted alkylene and alkylidene groups include the phenylmethylene, diphenylmethylene, 1-phenylethylene, 2-phenylethylene, 1,1-diphenylethylene, 2,2-diphenylethylene, α- and β- naphthylmethylene, 1-(α- and β- naphthyl)ethylene, 2-(α- and β- naphthyl) ethylene, 1 -phenyltrimethylene, 3-phenyltrimethylene, 1-phenyltetramethylene, 4-phenyltetramethylene, 1-phenylpentamethylene, 5-phenylpentamethylene, 1-phenylhexamethylene, 6-phenylhexamethylene, 1-phenylheptamethylene, 7-phenylheptamethylene, 1-phenyloctamethylene, 8-phenyloctamethylene, 1-phenylnonamethylene and 9-phenylnonamethylene groups, or any such group whose carbon chain is interrupted by 1 or 2 oxygen atoms, as illustrated above, preferably a phenylmethylene group.

Where $R^5$ or $R^6$ represents a cycloalkyl group, this has from 3 to 6 carbon atoms, and examples include the cyclopropyl, cyclobutyl, cyclopentyl and cyclohexyl groups, which may be unsubstituted or may be substituted by at least one alkyl group having from 1 to 4 carbon atoms (e.g. a methyl, ethyl, propyl, isopropyl, butyl, isobutyl, sec-butyl or t-butyl group). Of these, the cyclopentyl and cyclohexyl groups and substituted groups, such as the 4-methylcyclopentyl or 4-methylcyclohexyl groups, are preferred, and the cyclopentyl and cyclohexyl groups are more preferred.

Where $R^5$ and $R^6$, together with the nitrogen atom to which they are attached, represent a cyclic amino group, this has from 3 to 6 ring atoms, of which one is said nitrogen atom, 0 or 1 is an additional hetero-atom selected from the group consisting of nitrogen, oxygen and sulfur hetero-atoms and the remainder are carbon atoms. Such a group may be unsubstituted or it may have at least one substituent selected from the group consisting of substituents (c), defined and exemplified above. Examples of such groups include the 1-aziridinyl, 1-azetidinyl, 1-pyrrolidinyl, piperidino, morpholino, thiomorpholino and 1-piperazinyl groups, of which the 5- and 6-membered groups are preferred. Where the group is substituted, examples of the substituents include: $C_1$-$C_4$ alkyl, aryl and aralkyl groups, of which the methyl, ethyl, phenyl, benzyl, benzhydryl, p-chlorobenzhydryl and p,p'-difluorobenzhydryl groups are preferred.

Where J represents an alkylene or alkylidene group, it may be a straight or branched chain group having from 1 to 4 carbon atoms, and the "free" valencies may be on the same carbon atom or on different carbon atoms. Examples of such groups include those of the groups exemplified in relation to G which have from 1 to 4 carbon atoms.

Preferred examples of groups which may be represented by $R^3$ include the 3-hydroxypropyl, 2-hydroxypropyl, 4-hydroxybutyl, 3-hydroxybutyl, 5-hydroxypentyl, 4-hydroxypentyl, 3-hydroxypentyl, 6-hydroxyhexyl, 2-(2-hydroxyethoxy)ethyl, 2-[2-(2-hydroxyethoxy)ethoxy]ethyl, 3-carboxypropyl, 3-methoxycarbonylpropyl, 3-ethoxycarbonylpropyl, 3-propoxycarbonylpropyl, 3-butoxycarbonylpropyl, 3-t-butoxycarbonylpropyl, 4-carboxybutyl, 4-methoxycarbonylbutyl, 4-ethoxycarbonylbutyl, 4-propoxycarbonylbutyl, 4-isopropoxycarbonylbutyl, 4-butoxycarbonylbutyl, 5-carboxypentyl, 5-methoxycarbonylpentyl, 5-ethoxycarbonylpentyl, 6-carboxyhexyl, 6-methoxycarbonylhexyl, 6-ethoxycarbonylhexyl, 2-carboxymethoxyethyl, 2-methoxycarbonylmethoxyethyl, 2-ethoxycarbonylmethoxyethyl, 3-carboxymethoxypropyl, 3-methoxycarbonylmethoxypropyl, 3-ethoxycarbonylmethoxypropyl, 4-carboxymethoxybutyl, 4-methoxycarbonylmethoxybutyl, 4-ethoxycarbonylmethoxybutyl, 5-carboxymethoxypentyl, 5-methoxycarbonylmethoxypentyl, 5-ethoxycarbonylmethoxypentyl, 6-carboxymethoxyhexyl, 6-methoxycarbonylmethoxyhexyl, 6-ethoxycarbonylmethoxyhexyl, 6-propoxycarbonylmethoxyhexyl, 2-carbamoylmethoxyethyl, 2-(N-methylcarbamoylmethoxy)ethyl, 2-(N-ethylcarbamoylmethoxy)ethyl, 2-(N-propylcarbamoylmethoxy)ethyl, 2-(N-isopropylcarbamoylmethoxy)ethyl, 2-(N-butylcarbamoylmethoxy)ethyl, 2-(N-isobutylcarbamoylmethoxy)ethyl, 2-(N-t-butylcarbamoylmethoxy)ethyl, 2-(N-cyclopropylcarbamoylmethoxy)ethyl, 2-(N-cyclobutylcarbamoylmethoxy)ethyl, 2-(N-cyclopentylcarbamoylmethoxy)ethyl, 2-(N-cyclohexylcarbamoylmethoxy)ethyl, 2-(N-cycloheptylcarbamoylmethoxy)ethyl, 2-(N-phenylcarbamoylmethoxy)ethyl, 2-(N-o-, m- or p-chlorophenylcarbamoylmethoxy)ethyl, 2-(N-o-, m- or p-methylphenylcarbamoylmethoxy)ethyl, 2-(N-o-, m- or p-methoxyphenylcarbamoylmethoxy)ethyl, 2-(N-o-, m- or p-methoxyphenylcarbamoylmethoxy)ethyl, 2-(N-o-, m- or p-fluorophenylcarbamoylmethoxy)ethyl, 2-(N,N-dimethylcarbamoylmethoxy)ethyl, 2-(N,N-diethylcarbamoylmethoxy)ethyl, 2-(N,N-dipropylcarbamoylmethoxy)ethyl, 2-(N,N-dibutylcarbamoylmethoxy)ethyl, 2-(N-ethyl-N-methylcarbamoylmethoxy)ethyl, 2-(2-dimethylaminoethylcarbamoylmethoxy)ethyl, 2-(2-methylaminoethylcarbamoylmethoxy)ethyl, 2-(2-diethylaminoethylcarbamoylmethoxy)ethyl, 2-(N-benzylcarbamoylmethoxy)ethyl, 2-(N-phenethylcarbamoylmethoxy)ethyl, 2-[2-(4-methylpiperazin-1-yl)ethylcarbamoylmethoxy]ethyl, 2-[2-(4-phenylpiperazin-1-yl)ethylcarbamoylmethoxy]ethyl, 2- (2-morpholinoethylcarbamoylmethoxy)ethyl, 2-[2-(4-benzhydrylpiperazin-1-yl-)ethylcarbamoylmethoxy]ethyl, 2-[2-(4-o-, m- and p-methylbenzhydrylpiperazin-1-yl)ethylcarbamoylmethoxy]ethyl, 2-[2-(4-o-, m- and p- chlorobenzhydrylpiperazin-1-yl)ethylcarbamoylmethoxy]ethyl, 2-{2-[4-(o-, m- or p- fluoro-o'-, m'- or p'- fluorobenzhydryl)piperazin-1-yl]ethylcarbamoylmethoxy}ethyl, 2-(N-cyclohexyl-N-methylcarbamoylmethoxy)ethyl, 2-(N-cyclopentyl-N-methylcarbamoylmethoxy)ethyl, 2-(N-methyl-N-phenethylcarbamoylmethoxy)ethyl, 2-(N-benzyl-N-methylcarbamoylmethoxy)ethyl, 2-(N-benzyl-N-ethylcarbamoylmethoxy)ethyl, 2-(N-o-, m- or p- chlorobenzyl-N-methylcarbamoylmethoxy)ethyl, 2-(N-o-, m- or p- methylbenzyl-N-methylcarbamoylmethoxy)ethyl, 2-(N-o-, m- or p- methoxybenzyl-N-methylcarbamoylmethoxy)ethyl, 2-(aziridin-1-ylcarbonylmethoxy)ethyl, 2-(pyrrolidin-1-ylcarbonylmethoxy)ethyl, 2-(piperidinocarbonylmethoxy)ethyl, 2-(morpholinocarbonylmethoxy)ethyl, 2-(thiomorpholinocarbonylmethoxy)ethyl, 2-(4-methylpiperazin-1-ylcarbonylmethoxy)ethyl, 2-(4-phenylpiperazin-1-ylcarbonylmethoxy)ethyl, 2-(4-benzylpiperazin-1-ylcarbonylmethoxy)ethyl, 3-carbamoylmethoxypropyl, 3-(N-methylcarbamoylmethoxy)propyl, 3-(N-ethylcarbamoylmethoxy)propyl, 3-(N-propylcarbamoylmethoxy)propyl, 3-(N-butylcarbamoylmethoxy)propyl, 3-(N-cyclopropylcarbamoylmethoxy)propyl, 3-(N-cyclobutylcarbamoylmethoxy)propyl, 3-(N-cyclopentylcarbamoylmethoxy)propyl, 3-(N-cyclohexylcarbamoylmethoxy)propyl, 3-(N-phenylcarbamoylmethoxy)propyl 3-(N-o-, m- or p- chlorophenylcarbamoylmethoxy)propyl, 3-(N-o-, m- or p- fluorophenylcarbamoylmethoxy)propyl, 3-(N-o-, m- or p- methylphenylcarbamoylmethoxy)propyl, 3-(N-benzylcarbamoylmethoxy)propyl, 3-(pyrrolidin-1-ylcarbonylmethoxy)propyl, 3-(piperidinocarbonylmethoxy)propyl, 3-(morpholinocarbonylmethoxy)propyl, 3- (thiomorpholinocarbonylmethoxy)propyl, 3-(4-methylpiperazin-1-yl-carbonylmethoxy)propyl, 2,3-dihydroxypropyl, 3,4-dihydroxybutyl, 3-chloro-2-hydroxypropyl, 3-fluoro-2-hydroxypropyl, 4-chloro-3-hydroxybutyl, 3-amino-2-hydroxypropyl, 2-hydroxy-3-methylaminopropyl, 3-hydroxy-4-methylaminobutyl, 3-ethylamino-2-hydroxypropyl, 2-hydroxy-3-propylaminopropyl, 3-butylamino-2-hydroxypropyl, 3-isobutylamino-2-hydroxypropyl, 3-t-butylamino-2-hydroxypropyl, 3-(N,N-dimethylamino)-2-hydroxypropyl, 3-(N-ethyl-N-methylamino)-2-hydroxypropyl, 3-(N,N-diethylamino) -2-hydroxypropyl, 3-cyclopentylamino-2-hydroxypropyl, 3-cyclohexylamino-2-hydroxypropyl, 2-hydroxy-3- (o-, m- or p- methoxyphenylamino)propyl, 2-hydroxy-3-phenylaminopropyl, 3-(o-, m- or p- chlorophenylamino)-2-hydroxypropyl, 2-hydroxy-3-(o-, m- or p- methylphenylamino)propyl, 3-(o-, m- or p- fluorophenylamino)-2-hydroxypropyl, 2-hydroxy-3-morpholinopropyl, 2-hydroxy-3-thiomorpholinopropyl, 2-hydroxy-3-(4-methylpiperazin1-yl)propyl, 2-hydroxy-3-(4-phenylpiperazin-1-yl)propyl, 3-(4-benzylpiperazin-1-yl)-2-hydroxypropyl, 3-(4-benzhydrylpiperazin-1-yl)-2-hydroxypropyl, 3-(4-o-, m- or p-chlorobenzhydrylpiperazin-1-yl)-2-hydroxypropyl, 3-(4-o-, m- or p- fluoro-o'-, m'- or p'-fluorobenzhydrylpiperazin-1-yl)-2-hydroxypropyl, 2-hydroxy-3-(pyrrolidin-1-yl)propyl, 2-hydroxy-3-piperidinopropyl, 2-carbamoyloxyethyl, 2-(N-methylcarbamoyloxy)ethyl, 2-(N-ethylcarbamoyloxy)ethyl, 2-(N-propylcarbamoyloxy)ethyl, 2-(N-butylcarbamoyloxy)ethyl, 2-(N,N-dimethylcarbamoyloxy)ethyl, 2-(N,N-diethylcarbamoyloxy)ethyl)ethyl, 3-carbamoyloxypropyl, 3-(N-methylcarbamoyloxy)propyl, 3-(N-ethylcarbamoyloxy)propyl, 3-(N,N-dimethylcarbamoyloxy)propyl and 3-(N,N-diethylcarbamoyloxy)propyl groups.

Of these, the most preferred groups represented by $R^3$ are the 3-hydroxypropyl, 2-hydroxypropyl, 4-hydroxybutyl, 5-hydroxypentyl, 6-hydroxyhexyl, 2-(2-hydroxyethoxy)ethyl, 2-[2-(2-hydroxyethoxy)ethoxy]ethyl, 3-carboxypropyl, 3-methoxycarbonylpropyl, 3-ethoxycarbonylpropyl, 3-propoxycarbonylpropyl, 3-butoxycarbonylpropyl, 3-t-butoxycarbonylpropyl, 4-carboxybutyl, 4-methoxycarbonylbutyl, 4-ethoxycarbonylbutyl, 4-propoxycarbonylbutyl, 4-isopropoxycarbonylbutyl, 4-butoxycarbonylbutyl, 5-carboxypentyl, 5-methoxycarbonylpentyl, 2-carboxymethoxyethyl, 2-methoxycarbonylmethoxyethyl, 2-ethoxycarbonylmethoxyethyl, 3-carboxymethoxypropyl, 3-methoxycarbonylmethoxypropyl, 3-ethoxycarbonylmethoxypropyl, 2-carbamoylmethoxyethyl, 2-(N-methylcarbamoylmethoxy)ethyl, 2-(N-ethylcarbamylmethoxy)ethyl, 2-(N-propylcarbamoylmethoxy)ethyl, 2-(N-isopropylcarbamoylmethoxy)ethyl, 2-(N-butylcarbamoylmethoxy)ethyl, 2-(N-isobutylcarbamoylmethoxy) ethyl, 2-(N-t-butylcarbamoylmethoxy)ethyl, 2-(N-cyclopropylcarbamoylmethoxy)ethyl, 2-(N-cyclobutylcarbamoylmethoxy)ethyl, 2-(N-cyclopentylcarbamoylmethoxy)ethyl, 2-(N-cyclohexylcarbamoylmethoxy)ethyl, 2-(N-cycloheptylcarbamoylmethoxy)ethyl, 2-(N-phenylcarbamoylmethoxy)ethyl, 2-(N-o-, m- or p- chlorophenylcarbamoylmethoxy)ethyl, 2-(N-o-, m- or p-fluorophenylcarbamoylmethoxy)ethyl, 2-(N,N-dimethylcarbamoylmethoxy)ethyl, 2-(N,N-diethylcarbamoylmethoxy)ethyl, 2-(N-ethyl-N-methylcarbamoylmethoxy)ethyl, 2-(2-dimethylaminoethylcarbamoylmethoxy)ethyl, 2-(N-benzylcarbamoylmethoxy)ethyl, 2-[2-(4-methylpiperazin-1-yl)ethylcarbamoylmethoxy]ethyl, 2-(2-morpholinoethylcarbamoylmethoxy)ethyl, 2-(pyrrolidin-1-ylcarbonylmethoxy)ethyl, 2-(piperidinocarbonylmethoxy)ethyl, 2-(morpholinocarbonylmethoxy)ethyl, 2-(4-methylpiperazin-1-ylcarbonylmethoxy)ethyl, 2-(4-phenylpiperazin-1-ylcarbonylmethoxy)ethyl, 3-carbamoylmethoxypropyl, 3-(N-methylcarbamoylmethoxy)propyl, 3-(N-methylcarbamoylmethoxy)propyl, 3-(N-propylcarbamoylmethoxy)propyl, 3-(N-butylcarbamoylmethoxy)propyl, 3-(N-cyclopropylcarbamoylmethoxy)propyl, 3-(N-cyclobutylcarbamoylmethoxy)propyl, 3-(N-cyclopentylcarbamoylmethoxy)propyl, 3-(N-cyclohexylcarbamoylmethoxy)propyl, 3-(N-phenylcarbamoylmethoxy)propyl, 3-(N-o-, m- or p-chlorophenylcarbamoylmethoxy)propyl, 3-(N-o-, m- or p-fluorophenylcarbamoylmethoxy)propyl, 3-(piperidinocarbonylmethoxy)propyl, 3-(morpholinocarbonylmethoxy)propyl, 3-(4-methylpiperazin-1-yl-carbonylmethoxy)propyl, 2,3-dihydroxypropyl, 3-chloro-2-hydroxypropyl, 3-amino-2-hydroxypropyl, 2-hydroxy-3-methylaminopropyl, 3-ethylamino-2-hydroxypropyl, 2-hydroxy-3-propylaminopropyl, 3-butylamino-2-hydroxypropyl, 3-(N,N-dimethylamino)-2-hydroxypropyl, 3-(N,N-diethylamino) -2-hydroxypropyl, 3-cyclopentylamino-2-hydroxypropyl, 3-cyclohexylamino-2-hydroxylpropyl, 2-hydroxy-3-phenylaminopropyl, 3-(o-, m- or p- chlorophenylamino)-2-hydroxypropyl, 3-(o-, m- or p- fluorophenylamino)-2-hydroxypropyl, 2-hydroxy-3-morpholinopropyl, 2-hydroxy-3-(4-methylpiperazin-1-yl)propyl, 2-hydroxy-3-(4-phenylpiperazin-1-yl)propyl, 2-hydroxy-3-piperidinopropyl, 2-carbamoyloxyethyl, 2-(N-methylcarbamoyloxy)ethyl, 2-(N-ethylcarbamoyloxy)ethyl, 2-(N-propylcarbamoyloxy)ethyl and 2-(N-butylcarbamoyloxy)ethyl groups.

The compounds of the present invention can form salts. There is no particular restriction on the nature of these salts, provided that, where they are intended for therapeutic use, they are pharmaceutically acceptable. Where they are intended for non-therapeutic uses, e.g. as intermediates in the preparation of other, and possibly more active, compounds, even this restriction does not apply. The compounds of the present invention include several basic nitrogen atoms and can, therefore, form acid addition salts. Examples of such acid addition salts include: salts with mineral acids, such as hydrofluoric acid, hydrobromic acid, hydroiodic acid, hydrochloric acid, nitric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as fumaric acid, tartaric acid, oxalic acid, maleic acid, succinic acid or citric acid; and salts with amino acids, such as glutamic acid or aspartic acid. Also, the compounds may contain a free carboxylic acid group, and, in such a case, can form salts with bases. Examples of such salts include: salts with an alkali metal or alkaline earth metal, such as sodium, potassium, lithium, barium, calcium or magnesium; and organic base salts, such as a salt with dicyclohexylamine.

The compounds of the present invention necessarily contain several asymmetric carbon atoms in their molecules, and can thus form optical isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

Preferred classes of compounds of the present invention are those compounds of formula (I) and salts thereof in which:

(A) Q represents a group of formula =CH—.

(B) $R^1$ represents a hydrogen atom.

(C) $R^2$ represents a hydrogen or halogen atom, more preferably a hydrogen atom.

(D) $R^3$ represents an alkyl group having from 3 to 6 carbon atoms and substituted by a hydroxy group or by a group of formula —COOR$^4$, in which $R^4$ represents a hydrogen atom or an alkyl group having from 1 to 4 carbon atoms.

(E) $R^3$ represents a group of formula —CH$_2$CH$_2$OCH$_2$CH$_2$OH or —CH$_2$CH$_2$OCH$_2$CH$_2$OCH$_2$CH$_2$OH.

(F) $R^3$ represents a group of formula —E—O—G—COOR$^4$, where:

E represents an alkylene group having from 2 to 6 carbon atoms; G represents an alkylene group having 1 or 2 carbon atoms or a group of formula —CH$_2$CH$_2$OCH$_2$—, —CH$_2$CH$_2$OCH$_2$CH$_2$— or —CH$_2$CH$_2$OCH$_2$CH$_2$OCH$_2$—; and $R^4$ represents a hydrogen atom or an alkyl group having from 1 to 4 carbon atoms.

(G) $R^3$ represents a group of formula —E—O—G—$CONR^5R^6$, where:

E represents an alkylene group having from 2 to 6 carbon atoms;

G represents a single bond, an alkylene group having 1 or 2 carbon atoms or a group of formula —$CH_2CH_2OCH_2$—, —$CH_2CH_2OCH_2CH_2$— or —$CH_2CH_2OCH_2CH_2OCH_2$—; and $R^5$ and $R^6$ are independently selected from the group consisting of hydrogen atoms, unsubstituted alkyl groups having from 1 to 4 carbon atoms, substituted alkyl groups which have from 1 to 4 carbon atoms and which have at least one substituent selected from the group consisting of cyclic amino groups having 5 or 6 ring atoms, of which one is said nitrogen atom, 0 or 1 is an additional hetero-atom selected from the group consisting of nitrogen, oxygen and sulfur hetero-atoms and the remainder are carbon atoms, said heterocyclic group being unsubstituted or being substituted by at least one substituent selected from the group consisting of methyl, ethyl, phenyl, benzyl, benzhydryl, p-chlorobenzhydryl and p,p'-difluorobenzhydryl groups, cycloalkyl groups having from 3 to 7 ring carbon atoms, phenyl groups, which are unsubstituted or which have at least one substituent selected from the group consisting of halogen atoms, methyl groups and methoxy groups, and substituted alkyl groups which have from 1 to 4 carbon atoms, and which are substituted by 1 or 2 phenyl groups, the phenyl groups being unsubstituted or being substituted by at least one substituent selected from the group consisting of halogen atoms, methyl groups and methoxy groups;

or $R^5$ and $R^6$ together with the nitrogen atom to which they are attached, represent a cyclic amino group having 5 or 6 ring atoms, of which one is said nitrogen atom, 0 or 1 is an additional hetero-atom selected from the group consisting of nitrogen, oxygen and sulfur hereto-atoms and the remainder are carbon atoms, said heterocyclic group being unsubstituted or being substituted by at least one substituent selected from the group consisting of methyl, ethyl, phenyl, benzyl, benzhydryl, p-chlorobenzhydryl and, p,p'-difluorobenzhydryl substituents.

(H) $R^3$ represents a group of formula —$CH_2$—CH(OH)—$CH_2R^7$, where $R^7$ represents a hydroxy group, a halogen atom or a group of formula —$NR^5R^6$, where:

$R^5$ and $R^6$ are independently selected from the group consisting of hydrogen atoms, alkyl groups having from 1 to 4 carbon atoms, cyclopentyl groups, cyclohexyl groups, unsubstituted phenyl groups and substituted phenyl groups having at least one substituent selected from the group consisting of halogen atoms, methyl groups and methoxy groups, or or $R^5$ and $R^6$ together with the nitrogen atom to which they are attached, represent a cyclic amino group having 5 or 6 ring atoms, of which one is said nitrogen atom, 0 or 1 is an additional hetero-atom selected from the group consisting of nitrogen, oxygen and sulfur hetero-atoms and the remainder are carbon atoms, said heterocyclic group being unsubstituted or being substituted by at least one substituent selected from the group consisting of methyl, ethyl, phenyl, benzyl, benzhydryl, p-chlorobenzhydryl and p,p'-difluorobenzhydryl substituents.

More preferred are compounds of formula (I) in which Q is as defined in (A) above, $R^1$ is as defined in (B) above, $R^2$ is as defined in (C) above and $R^3$ is as defined in any one of (D) to (H) above.

Still more preferred classes of compounds of the present invention are those compounds of formula (I) and salts thereof in which:

(I) $R^3$ represents a hydroxyalkyl group having from 3 to 6 carbon atoms.

(J) $R^3$ represents an alkyl group having from 3 to 5 carbon atoms and substituted by a group of formula —$COOR^4$ where:

$R^4$ represents a hydrogen atom or an alkyl group having from 1 to 4 carbon atoms.

(K) $R^3$ represents a group of formula —E—O—G—$COOR^4$, where:

E represents an alkylene group having from 2 to 4 carbon atoms;

G represents an alkylene group having 1 or 2 carbon atoms or a group of formula —$CH_2CH_2OCH_2$— or —$CH_2CH_2OCH_2CH_2OCH_2$—; and $R^4$ represents a hydrogen atom or an alkyl group having from 1 to 4 carbon atoms.

(L) $R^3$ represents a group of formula —E—O—G—$CONR^5R^6$ where:

E represents an alkylene group having from 2 to 4 carbon atoms;

G represents a single bond, an alkylene group having one or two carbon atoms or a group of formula —$CH_2CH_2OCH_2$— or —$CH_2CH_2OCH_2CH_2OCH_2$—; and $R^5$ and $R^6$ are independently selected from the group consisting of hydrogen atoms, unsubstituted alkyl groups having from 1 to 4 carbon atoms, unsubstituted cycloalkyl groups having from 3 to 7 ring carbon atoms, phenyl groups, which are unsubstituted or have at least one substituent selected from the group consisting of halogen atoms, methyl groups and methoxy groups, and substituted alkyl groups having from 1 to 4 carbon atoms and substituted by an unsubstituted phenyl group or by a substituted phenyl group which itself has at least one substituent selected from the group consisting of methyl, methoxy and halogen substituents.

Still more preferred compounds of the invention are those compounds of formula (I) and salts thereof in which Q is as defined in (A) above, $R^1$ is as defined in (B) above, $R^2$ is as defined in (C) above and $R^3$ is as defined in any one of (I) to (L) above.

The most preferred classes of compounds of the present invention are those compounds of formula (I) and salts thereof in which:

(M) $R^3$ represents a hydroxyalkyl group having from 3 to 6 carbon atoms.

(N) $R^3$ represents an alkyl group having 3 or 5 carbon atoms and substituted by a group of formula —$COOR^4$, where:

$R^4$ represents a hydrogen atom or an alkyl group having from 1 to 4 carbon atoms.

(O) $R^3$ represents a group of formula —$CH_2CH_2$—O—$CH_2$—$COOR^4$, where:

$R^4$ represents a hydrogen atom or an alkyl group having from 1 to 4 carbon atoms.

(P) $R^3$ represents a group of formula —$CH_2CH_2$—O—$CH_2$—$CONR^5R^6$, where:

$R^5$ and $R^6$ are the same or different and each represents a hydrogen atom, an alkyl group having from 1 to 4 carbon atoms, a cycloalkyl group having from 3 to 6 carbon atoms, an unsubstituted phenyl group, a substituted phenyl group having at least one substituent selected from the group consisting of methyl, methoxy, chlorine and fluorine substituents, an unsubstituted benzyl group or a substituted benzyl group having at least one substituent selected from the group consisting of methyl, methoxy, chlorine and fluorine substituents.

Especially preferred compounds of the invention are those compounds of formula (I) and salts thereof in which Q is as defined in (A) above, $R^1$ is as defined in (B) above, $R^2$ is as defined in (C) above and $R^3$ is as defined in any one of (M) to (P) above.

Although the preferred compounds of the present invention are those compounds of formula (I) and salts thereof where one or both of $R^1$ and $R^2$ represent hydrogen atoms, where $R^1$ or $R^2$ represents a group or atom other than a hydrogen atom, these are preferably at the 13- and 8- positions, respectively, i.e. the preferred compounds in this case are those compounds of formula (Ia):

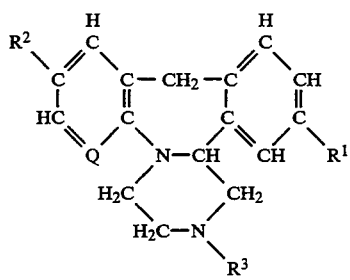

(Ia)

(where $R^1$, $R^2$, $R^3$ and Q are as defined above).

Examples of specific compounds of the invention are given in the following formulae (I-1) to (I-3), in which the substituents are as defined in the corresponding one of Tables 1 to 3, respectively [i.e. Table 1 relates to formula (I-1), Table 2 relates to formula (I-2) and Table 3 relates to formula (I-3).

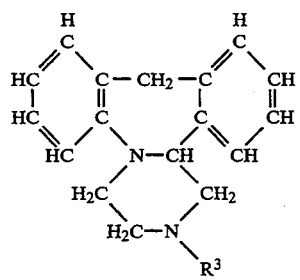

(I-1)

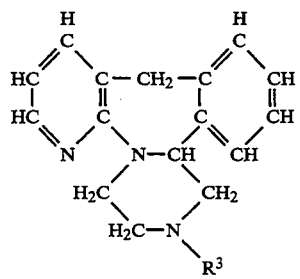

(I-2)

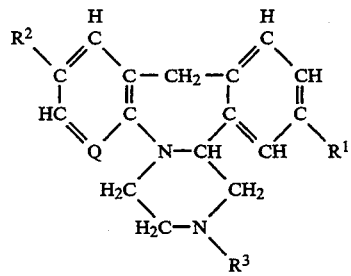

(I-3)

In the following Tables, certain abbreviations are used for the sake of brevity, and these abbreviations have the following meanings:

| | |
|---|---|
| Azi | aziridinyl |
| Bu | butyl |
| cBu | cyclobutyl |
| iBu | isobutyl |
| tBu | t-butyl |
| Bz | benzyl |
| Bzhy | benzhydryl |
| Et | ethyl |
| cHp | cycloheptyl |
| cHx | cyclohexyl |
| Me | methyl |
| Mor | morpholino |
| Ph | phenyl |
| Pip | piperidyl |
| Piz | piperazinyl |
| cPn | cyclopentyl |
| Pr | propyl |
| cPr | cyclopropyl |
| iPr | isopropyl |
| Pyrd | pyrrolidinyl |
| Thz | perhydro-1,4-thiazin-4-yl (= thiomorpholino) |

TABLE 1

| Compound No. | $R^3$ |
|---|---|
| 1-1 | —$(CH_2)_3COOH$ |
| 1-2 | —$(CH_2)_4COOH$ |
| 1-3 | —$(CH_2)_5COOH$ |
| 1-4 | —$(CH_2)_6COOH$ |
| 1-5 | —$(CH_2)_3COOMe$ |
| 1-6 | —$(CH_2)_4COOMe$ |
| 1-7 | —$(CH_2)_5COOMe$ |
| 1-8 | —$(CH_2)_6COOMe$ |

TABLE 1-continued

| Compound No. | $R^3$ |
|---|---|
| 1-9 | —$(CH_2)_3COOEt$ |
| 1-10 | —$(CH_2)_4COOEt$ |
| 1-11 | —$(CH_2)_5COOEt$ |
| 1-12 | —$(CH_2)_6COOEt$ |
| 1-13 | —$(CH_2)_3COOiPr$ |
| 1-14 | —$(CH_2)_3COOiPr$ |
| 1-15 | —$(CH_2)_4COOPr$ |
| 1-16 | —$(CH_2)_5COOPr$ |
| 1-17 | —$(CH_2)_3COOBu$ |
| 1-18 | —$(CH_2)_3COOiBu$ |
| 1-19 | —$(CH_2)_4COOBu$ |
| 1-20 | —$(CH_2)_3OH$ |
| 1-21 | —$(CH_2)_4OH$ |
| 1-22 | —$CH_2CH(OH)CH_3$ |
| 1-23 | —$(CH_2)_5OH$ |
| 1-24 | —$(CH_2)_6OH$ |
| 1-25 | —$(CH_2)_3OCH_2COOH$ |
| 1-26 | —$(CH_2)_4OCH_2COOH$ |
| 1-27 | —$(CH_2)_2OCH_2COOH$ |
| 1-28 | —$(CH_2)_2OCH_2COOMe$ |
| 1-29 | —$(CH_2)_3OCH_2COOMe$ |
| 1-30 | —$(CH_2)_4OCH_2COOMe$ |
| 1-31 | —$(CH_2)_5OCH_2COOMe$ |
| 1-32 | —$(CH_2)_6OCH_2COOMe$ |
| 1-33 | —$(CH_2)_2OCH_2COOEt$ |
| 1-34 | —$(CH_2)_3OCH_2COOEt$ |
| 1-35 | —$(CH_2)_4OCH_2COOEt$ |
| 1-36 | —$(CH_2)_5OCH_2COOEt$ |
| 1-37 | —$(CH_2)_6OCH_2COOEt$ |
| 1-38 | —$(CH_2)_2OCH_2COOPr$ |
| 1-39 | —$(CH_2)_3OCH_2COOiPr$ |
| 1-40 | —$(CH_2)_4OCH_2COOPr$ |
| 1-41 | —$(CH_2)_2OCH_2COOBu$ |
| 1-42 | —$(CH_2)_4OCH_2COOBu$ |
| 1-43 | —$(CH_2)_2OCH_2CONH_2$ |
| 1-44 | —$(CH_2)_2OCH_2CH_2CONH_2$ |
| 1-45 | —$(CH_2)_2OCH_2CONHMe$ |
| 1-46 | —$(CH_2)_2OCH_2CH_2CONHMe$ |
| 1-47 | —$(CH_2)_2OCH_2CONHEt$ |
| 1-48 | —$(CH_2)_2OCH_2CONHPr$ |
| 1-49 | —$(CH_2)_2OCH_2CONHiPr$ |
| 1-50 | —$(CH_2)_2OCH_2CONHBu$ |
| 1-51 | —$(CH_2)_2OCH_2CONHiBu$ |
| 1-52 | —$(CH_2)_2OCH_2CONHtBu$ |
| 1-53 | —$(CH_2)_2OCH_2CONMe_2$ |
| 1-54 | —$(CH_2)_2OCH_2CONiPr_2$ |
| 1-55 | —$(CH_2)_3OCH_2CONH_2$ |
| 1-56 | —$(CH_2)_3OCH_2CONHMe$ |
| 1-57 | —$(CH_2)_3OCH_2CONHEt$ |
| 1-58 | —$(CH_2)_3OCH_2CONHPr$ |
| 1-59 | —$(CH_2)_3OCH_2CONHBu$ |
| 1-60 | —$(CH_2)_2OCH_2CONHcPr$ |
| 1-61 | —$(CH_2)_2OCH_2CONHcBu$ |
| 1-62 | —$(CH_2)_2OCH_2CONHcPn$ |
| 1-63 | —$(CH_2)_2OCH_2CONH(3-MecPn)$ |
| 1-64 | —$(CH_2)_2OCH_2CONHcHx$ |
| 1-65 | —$(CH_2)_2OCH_2CONH(4-MecHx)$ |
| 1-66 | —$(CH_2)_2OCH_2CONHcHp$ |
| 1-67 | —$(CH_2)_2OCH_2CH_2CONHcPn$ |
| 1-68 | —$(CH_2)_2OCH_2CH_2CONHcHx$ |
| 1-69 | —$(CH_2)_3OCH_2CONHcPr$ |
| 1-70 | —$(CH_2)_3OCH_2CONHcPn$ |
| 1-71 | —$(CH_2)_3OCH_2CONHcHx$ |
| 1-72 | —$(CH_2)_2OCH_2CONHPh$ |
| 1-73 | —$(CH_2)_2OCH_2CONH(4-ClPh)$ |
| 1-74 | —$(CH_2)_2OCH_2CONH(3-ClPh)$ |
| 1-75 | —$(CH_2)_2OCH_2CONH(2-ClPh)$ |
| 1-76 | —$(CH_2)_2OCH_2CONH(4-FPh)$ |
| 1-77 | —$(CH_2)_2OCH_2CONH(3-FPh)$ |
| 1-78 | —$(CH_2)_2OCH_2CONH(4-MePh)$ |
| 1-79 | —$(CH_2)_2OCH_2CONH(3-MePh)$ |
| 1-80 | —$(CH_2)_2OCH_2CONH(4-MeOPh)$ |
| 1-81 | —$(CH_2)_2OCH_2CH_2CONHPh$ |
| 1-82 | —$(CH_2)_3OCH_2CONHPh$ |
| 1-83 | —$(CH_2)_3OCH_2CONH(4-ClPh)$ |
| 1-84 | —$(CH_2)_2OCH_2CONHBz$ |
| 1-85 | —$(CH_2)_2OCH_2CONH(4-ClBz)$ |
| 1-86 | —$(CH_2)_2OCH_2CONH(4-MeOBz)$ |
| 1-87 | —$(CH_2)_2OCH_2CONH(4-MeBz)$ |
| 1-88 | —$(CH_2)_2OCH_2CON(Me)Bz$ |
| 1-89 | —$(CH_2)_2OCH_2CON(Me)(4-MeBz)$ |
| 1-90 | —$(CH_2)_2OCH_2CON(Me)(4-MeOBz)$ |
| 1-91 | —$(CH_2)_2OCH_2CON(Et)Bz$ |
| 1-92 | —$(CH_2)_2OCH_2CON(Me)(4-ClBz)$ |
| 1-93 | —$(CH_2)_2OCH_2CON(Me)(2-PhEt)$ |
| 1-94 | —$(CH_2)_2OCH_2CONH(2-PhEt)$ |
| 1-95 | —$(CH_2)_2OCH_2CON(Me)cHx$ |
| 1-96 | —$(CH_2)_2OCH_2COMor$ |
| 1-97 | —$(CH_2)_2OCH_2COThz$ |
| 1-98 | —$(CH_2)_2OCH_2CH_2COMor$ |
| 1-99 | —$(CH_2)_2OCH_2CO(1-Azi)$ |
| 1-100 | —$(CH_2)_2OCH_2CO(1-Pyrd)$ |
| 1-101 | —$(CH_2)_2OCH_2CO(1-Pip)$ |
| 1-102 | —$(CH_2)_2OCH_2CO(1-Piz)$ |
| 1-103 | —$(CH_2)_2OCH_2CO(4-Me-1-Piz)$ |
| 1-104 | —$(CH_2)_2OCH_2CO(4-Ph-1-Piz)$ |
| 1-105 | —$(CH_2)_2OCH_2CO(4-Bz-1-Piz)$ |
| 1-106 | —$(CH_2)_3OCH_2COMor$ |
| 1-107 | —$(CH_2)_4OCH_2COMor$ |
| 1-108 | —$(CH_2)_3OCH_2CO(1-Pip)$ |
| 1-109 | —$(CH_2)_2OCH_2CONH(2-NH_2Et)$ |
| 1-110 | —$(CH_2)_2OCH_2CONH(2-NMe_2Et)$ |
| 1-111 | —$(CH_2)_3OCH_2CONH(2-NMe_2Et)$ |
| 1-112 | —$(CH_2)_2OCH_2CONH[2-(4-BzhyPiz)Et]$ |
| 1-113 | —$(CH_2)_2OCH_2CONH[2-(4-p,p'-diFBzhyPiz)Et]$ |
| 1-114 | —$(CH_2)_2O(CH_2)_2OCH_2CONH_2$ |
| 1-115 | —$(CH_2)_2O(CH_2)_2OCH_2CONHMe$ |
| 1-116 | —$(CH_2)_2O(CH_2)_2OCH_2CONHEt$ |
| 1-117 | —$(CH_2)_2O(CH_2)_2OCH_2CONHPr$ |
| 1-118 | —$(CH_2)_2O(CH_2)_2OCH_2CONHiPr$ |
| 1-119 | —$(CH_2)_2O(CH_2)_2OCH_2CONHBu$ |
| 1-120 | —$(CH_2)_2O(CH_2)_2OCH_2CONHiBu$ |
| 1-121 | —$(CH_2)_2O(CH_2)_2OCH_2CONHcPn$ |
| 1-122 | —$(CH_2)_2O(CH_2)_2OCH_2CONHcHx$ |
| 1-123 | —$(CH_2)_2O(CH_2)_2OCH_2CONHPh$ |
| 1-124 | —$(CH_2)_2O(CH_2)_2OCH_2CONH(4-ClPh)$ |
| 1-125 | —$(CH_2)_2O(CH_2)_2OCH_2CONH(1-Pip)$ |
| 1-126 | —$(CH_2)_2O(CH_2)_2OCH_2CONH(1-Pyrd)$ |
| 1-127 | —$(CH_2)_2O(CH_2)_2OCH_2CONHMor$ |
| 1-128 | —$(CH_2)_2OCONH_2$ |
| 1-129 | —$(CH_2)_2OCONHMe$ |
| 1-130 | —$(CH_2)_2OCONHEt$ |
| 1-131 | —$(CH_2)_2OCONHPr$ |
| 1-132 | —$(CH_2)_2OCONHBu$ |
| 1-133 | —$(CH_2)_3OCONH_2$ |
| 1-134 | —$(CH_2)_3OCONHMe$ |
| 1-135 | —$(CH_2)_3OCONHEt$ |
| 1-136 | —$(CH_2)_4OCONH_2$ |
| 1-137 | —$(CH_2)_4OCONHMe$ |
| 1-138 | —$(CH_2)_4OCONHEt$ |
| 1-139 | —$(CH_2)_2OCONMe_2$ |
| 1-140 | —$(CH_2)_3OCONMe_2$ |
| 1-141 | —$(CH_2)_2OCONEt_2$ |
| 1-142 | —$CH_2CH(OH)CH_2OH$ |
| 1-143 | —$CH_2CH(OH)CH_2Cl$ |
| 1-144 | —$CH_2CH(OH)CH_2NH_2$ |
| 1-145 | —$CH_2CH(OH)CH_2NHMe$ |
| 1-146 | —$CH_2CH(OH)CH_2NHEt$ |
| 1-147 | —$CH_2CH(OH)CH_2NHPr$ |
| 1-148 | —$CH_2CH(OH)CH_2NHiPr$ |
| 1-149 | —$CH_2CH(OH)CH_2NHBu$ |
| 1-150 | —$CH_2CH(OH)CH_2NHiBu$ |
| 1-151 | —$CH_2CH(OH)CH_2NHtBu$ |
| 1-152 | —$CH_2CH(OH)CH_2NMe_2$ |
| 1-153 | —$CH_2CH(OH)CH_2NEt_2$ |
| 1-154 | —$CH_2CH(OH)CH_2NPr_2$ |
| 1-155 | —$CH_2CH(OH)CH_2NHcPn$ |
| 1-156 | —$CH_2CH(OH)CH_2NHcHx$ |
| 1-157 | —$CH_2CH(OH)CH_2NHPh$ |
| 1-158 | —$CH_2CH(OH)CH_2NH(4-ClPh)$ |
| 1-159 | —$CH_2CH(OH)CH_2NHBz$ |
| 1-160 | —$CH_2CH(OH)CH_2(1-Pyrd)$ |
| 1-161 | —$CH_2CH(OH)CH_2(1-Pip)$ |
| 1-162 | —$CH_2CH(OH)CH_2Mor$ |
| 1-163 | —$CH_2CH(OH)CH_2Thz$ |
| 1-164 | —$CH_2CH(OH)CH_2(4-MePiz)$ |
| 1-165 | —$CH_2CH(OH)CH_2(4-BzhyPiz)$ |
| 1-166 | —$CH_2CH(OH)CH_2(4-p-ClBzhyPiz)$ |
| 1-167 | —$CH_2CH_2OCH_2CH_2OH$ |
| 1-168 | —$CH_2CH_2OCH_2CH_2OCH_2COOEt$ |
| 1-169 | —$CH_2CH_2OCH_2CH_2OCH_2CH_2OH$ |

TABLE 1-continued

| Compound No. | R³ |
|---|---|
| 1-170 | —CH₂CH₂OCH₂CH₂OCH₂CH₂OCH₂COOEt |

TABLE 2

| Compound No. | R³ |
|---|---|
| 2-1 | —(CH₂)₃OH |
| 2-2 | —(CH₂)₄OH |
| 2-3 | —(CH₂)₅OH |
| 2-4 | —(CH₂)₆OH |
| 2-5 | —(CH₂)₃COOH |
| 2-6 | —(CH₂)₄COOH |
| 2-7 | —(CH₂)₃COOMe |
| 2-8 | —(CH₂)₄COOMe |
| 2-9 | —(CH₂)₅COOMe |
| 2-10 | —(CH₂)₆COOMe |
| 2-11 | —(CH₂)₃COOEt |
| 2-12 | —(CH₂)₄COOEt |
| 2-13 | —(CH₂)₅COOEt |
| 2-14 | —(CH₂)₃COOPr |
| 2-15 | —(CH₂)₂OCH₂COOH |
| 2-16 | —(CH₂)₃OCH₂COOH |
| 2-17 | —(CH₂)₆OCH₂COOH |
| 2-18 | —(CH₂)₂OCH₂COOMe |
| 2-19 | —(CH₂)₃OCH₂COOMe |
| 2-20 | —(CH₂)₄OCH₂COOMe |
| 2-21 | —(CH₂)₅OCH₂COOMe |
| 2-22 | —(CH₂)₂OCH₂COOEt |
| 2-23 | —(CH₂)₃OCH₂COOEt |
| 2-24 | —(CH₂)₄OCH₂COOEt |
| 2-25 | —(CH₂)₂OCH₂CONH₂ |
| 2-26 | —(CH₂)₂OCH₂CONHMe |
| 2-27 | —(CH₂)₂OCH₂CONHEt |
| 2-28 | —(CH₂)₂OCH₂CONHPr |
| 2-29 | —(CH₂)₂OCH₂CONHBu |
| 2-30 | —(CH₂)₂OCH₂CONMe₂ |
| 2-31 | —(CH₂)₂OCH₂CONHcPn |
| 2-32 | —(CH₂)₂OCH₂CONHcHx |
| 2-33 | —(CH₂)₂OCH₂CONHPh |
| 2-34 | —(CH₂)₂OCH₂CO(1-pip) |
| 2-35 | —(CH₂)₂OCH₂CO(1-Pyrd) |
| 2-36 | —(CH₂)₂OCH₂COMor |
| 2-37 | —(CH₂)₂OCH₂CONEt₂ |
| 2-38 | —(CH₂)₂OCH₂CH₂COOH |
| 2-39 | —(CH₂)₂OCH₂CH₂COOMe |
| 2-40 | —(CH₂)₂OCH₂CH₂COOEt |
| 2-41 | —(CH₂)₂OCH₂CH₂COOPr |
| 2-42 | —(CH₂)₂O(CH₂)₃COOMe |
| 2-43 | —(CH₂)₂O(CH₂)₃COOEt |
| 2-44 | —CH₂CH(OH)CH2OH |
| 2-45 | —CH₂CH(OH)CH₂Mor |
| 2-46 | —CH2CH(OH)CH₂NHMe |
| 2-47 | —CH₂CH(OH)CH₂(1-Pip) |
| 2-48 | —CH₂CH(OH)CH₂(4-Me-1-Piz) |
| 2-49 | —CH₂CH(OH)CH₂(4-p-ClBzhy-1-Piz) |
| 2-50 | —(CH₂)₂OCH₂CH₂OH |
| 2-51 | —(CH₂)₂OCH₂CH₂OCH₂COOEt |
| 2-52 | —(CH₂)₂OCH₂CH₂OCH₂COOH |
| 2-53 | —(CH₂CH₂O)₃CH₂COOEt |
| 2-54 | —(CH₂CH₂O)₃CH₂COOH |

TABLE 3

| Cpd. No. | Q | R¹ | R² | R³ |
|---|---|---|---|---|
| 3-1 | =CH— | H | Cl | —(CH₂)₃OH |
| 3-2 | =CH— | H | Cl | —(CH₂)₄OH |
| 3-3 | =CH— | H | Cl | —(CH₂)₃COOH |
| 3-4 | =CH— | H | Cl | —(CH₂)₃COOMe |
| 3-5 | =CH— | H | Cl | —(CH₂)₄COOMe |
| 3-6 | =CH— | H | Cl | —(CH₂)₃COOEt |
| 3-7 | =CH— | H | Cl | —(CH₂)₄COOEt |
| 3-8 | =CH— | H | Cl | —(CH₂)₅COOEt |
| 3-9 | =CH— | H | Cl | —(CH₂)₃OCH₂COOH |
| 3-10 | =CH— | H | Cl | —(CH₂)₂OCH₂COOMe |
| 3-11 | =CH— | H | Cl | —(CH₂)₃OCH₂COOMe |
| 3-12 | =CH— | H | Cl | —(CH₂)₃OCH₂COOEt |
| 3-13 | =CH— | H | Cl | —(CH₂)₄OCH₂COOEt |
| 3-14 | =CH— | H | Cl | —(CH₂)₂OCH₂CONH₂ |
| 3-15 | =CH— | H | Cl | —(CH₂)₂OCH₂CONHMe |
| 3-16 | =CH— | H | Cl | —(CH₂)₂OCH₂CONHEt |
| 3-17 | =CH— | H | Cl | —(CH₂)₂OCH₂CONHPr |
| 3-18 | =CH— | H | Cl | —(CH₂)₂OCH₂CONHcHx |
| 3-19 | =CH— | H | Cl | —(CH₂)₂OCH₂CONHPh |
| 3-20 | =CH— | H | Cl | —(CH₂)₂OCH₂CO(1-pip) |
| 3-21 | =CH— | H | Cl | —(CH₂)₂OCH₂COMor |
| 3-22 | =CH— | H | Cl | —(CH₂)₂OCH₂CO(4-Me-1-Piz) |
| 3-23 | =CH— | H | F | —(CH₂)₃OH |
| 3-24 | =CH— | H | F | —(CH₂)₄OH |
| 3-25 | =CH— | H | F | —(CH₂)₃COOMe |
| 3-26 | =CH— | H | F | —(CH₂)₃COOEt |
| 3-27 | =CH— | H | F | —(CH₂)₄COOMe |
| 3-28 | =CH— | H | F | —(CH₂)₄COOEt |
| 3-29 | =CH— | H | F | —(CH₂)₂OCH₂CONH₂ |
| 3-30 | =CH— | H | F | —(CH₂)₂OCH₂CONHMe |
| 3-31 | =CH— | H | F | —(CH₂)₂OCH₂CONHEt |
| 3-32 | =CH— | H | F | —(CH₂)₂OCH₂CONHcHx |
| 3-33 | =CH— | H | F | —(CH₂)₂OCH₂CONHPh |
| 3-34 | =CH— | H | F | —(CH₂)₂OCH₂COMor |
| 3-35 | =CH— | H | Br | —(CH₂)₃OH |
| 3-36 | =CH— | H | Br | —(CH₂)₄OH |
| 3-37 | =CH— | H | Br | —(CH₂)₃COOH |
| 3-38 | =CH— | H | Br | —(CH₂)₄COOH |
| 3-39 | =CH— | H | Br | —(CH₂)₃COOMe |
| 3-40 | =CH— | H | Br | —(CH₂)₄COOMe |
| 3-41 | =CH— | H | Br | —(CH₂)₃COOEt |
| 3-42 | =CH— | H | Br | —(CH₂)₄COOEt |
| 3-43 | =CH— | H | Br | —(CH₂)₂OCH₂COOH |
| 3-44 | =CH— | H | Br | —(CH₂)₂OCH₂COOMe |
| 3-45 | =CH— | H | Br | —(CH₂)₂OCH₂COOEt |
| 3-46 | =CH— | H | Br | —(CH₂)₂OCH₂CONH₂ |
| 3-47 | =CH— | H | Br | —(CH₂)₂OCH₂CONHMe |
| 3-48 | =CH— | H | Br | —(CH₂)₂OCH₂CONHEt |
| 3-49 | =CH— | H | Br | —(CH₂)₂OCH₂CONHPr |
| 3-50 | =CH— | H | Br | —(CH₂)₂OCH₂CONHcHx |
| 3-51 | =CH— | H | Br | —(CH₂)₂OCH₂CONHPh |
| 3-52 | =CH— | H | Br | —(CH₂)₂OCH₂COpip |
| 3-53 | =CH— | H | Br | —(CH₂)₂OCH₂COMor |
| 3-54 | =CH— | H | Br | —(CH₂)₂OCH₂CO(4-MePiz) |
| 3-55 | N | H | Cl | —(CH₂)₃OH |
| 3-56 | N | H | Cl | —(CH₂)₄OH |
| 3-57 | N | H | F | —(CH₂)₄OH |
| 3-58 | N | H | Cl | —(CH₂)₃COOH |
| 3-59 | N | H | Cl | —(CH₂)₃COOMe |
| 3-60 | N | H | F | —(CH₂)₃COOMe |
| 3-61 | N | H | Cl | —(CH₂)₃COOEt |
| 3-62 | N | H | Cl | —(CH₂)₄COOEt |
| 3-63 | N | H | Cl | —(CH₂)₂OCH₂COOEt |
| 3-64 | N | H | Cl | —(CH₂)₂OCH₂COOH |
| 3-65 | N | H | Cl | —(CH₂)₂OCH₂CONH₂ |
| 3-66 | N | H | Cl | —(CH₂)₂OCH₂CONHMe |
| 3-67 | N | H | F | —(CH₂)₂OCH₂CONHMe |
| 3-68 | N | H | Cl | —(CH₂)₂OCH₂CONHEt |
| 3-69 | N | H | Cl | —(CH₂)₂OCH₂CONHcHx |
| 3-70 | N | H | Cl | —(CH₂)₂OCH₂CONHPh |
| 3-71 | N | H | F | —(CH₂)₂OCH₂CONHPh |
| 3-72 | N | H | Cl | —(CH₂)₂OCH₂COMor |
| 3-73 | N | H | Cl | —(CH₂)₂OCH₂CO(4-MePiz) |
| 3-74 | N | H | Br | —(CH₂)₃OH |
| 3-75 | N | H | Br | —(CH₂)₄OH |
| 3-76 | N | H | Br | —(CH₂)₂OCH₂COOMe |
| 3-77 | N | H | Br | —(CH₂)₂OCH₂COOEt |
| 3-78 | N | H | Br | —(CH₂)₃COOMe |
| 3-79 | N | H | Br | —(CH₂)₃COOEt |
| 3-80 | N | H | Br | —(CH₂)₄COOEt |
| 3-81 | N | H | Br | —(CH₂)₂OCH₂CONH₂ |
| 3-82 | N | H | Br | —(CH₂)₂OCH₂CONHMe |
| 3-83 | N | H | Sr | —(CH₂)₂OCH₂CONHEt |
| 3-84 | N | H | Br | —(CH₂)₂OCH₂CONHcHx |
| 3-85 | N | H | Br | —(CH₂)₂OCH₂CONHPh |
| 3-86 | N | H | Br | —(CH₂)₂OCH₂COMor |
| 3-87 | N | H | Br | —(CH₂)₂OCH₂CO(4-MePiz) |
| 3-88 | =CH— | H | Cl | —(CH₂)₂OCH₂COOEt |
| 3-89 | =CH— | H | Cl | —(CH₂)₂OCH₂COOH |
| 3-90 | =CH— | H | Br | —(CH₂)₂OCH₂COOMe |
| 3-91 | =CH— | H | Br | —(CH₂)₂OCH₂COOH |
| 3-92 | =CH— | Cl | H | —(CH₂)₂OCH₂COOEt |
| 3-93 | =CH— | Cl | H | —(CH₂)₂OCH₂COOH |
| 3-94 | =CH— | Br | H | —(CH₂)₂OCH₂COOH |

TABLE 3-continued

| Cpd. No. | Q | R¹ | R² | R³ |
|---|---|---|---|---|
| 3-95 | =CH— | Me | H | —(CH₂)₂OCH₂COOH |
| 3-96 | =CH— | H | F | —(CH₂)₂OCH₂COOH |
| 3-97 | =CH— | H | F | —(CH₂)₃COOH |
| 3-98 | N | H | F | —(CH₂)₂OCH₂COOH |

Of the compounds listed above, the following compounds are preferred, that i s to say Compounds No. 1-1, 1-3, 1-5, 1-7, 1-9, 1-11, 1-20, 1-21, 1-23, 1-24, 1-25, 1-26, 1-27, 1-28, 1-29, 1-30, 1-31, 1-32, 1-33, 1-34, 1-35, 1-36, 1-37, 1-38, 1-41, 1-43, 1-54, 1-67, 1-68, 1-69, 1-72, 1-114, 1-128, 1-133, 1-167, 1-168, 1-169, 1-170, 2-1, 2-2, 2-3, 2-4, 2-5, 2-7, 2-9, 2-11, 2-13, 2-15, 2-16, 2-17, 2-18, 2-19, 2-20, 2-21, 2-22, 2-23, 2-24, 2-25, 2-50, 2-53, 2-54, 3-3, 3-4, 3-6, 3-8, 3-9, 3-10, 3-11, 3-13, 3-14, 3-25, 3-26, 3-37, 3-39, 3-41, 3-58, 3-59, 3-78, 3-79, 3-88, 3-89, 3-90, 3-91, 3-92, 3-93, 3-94, 3-95, 3-96, 3-97, and 3-98, and the following are more preferred, that is to say Compounds No. 1-1, 1-3, 1-5, 1-7, 1-9, 1-11, 1-20, 1-23, 1-24, 1-27, 1-28, 1-33, 1-34, 1-37, 1-43, 1-54, 2-5, 2-7, 2-9, 2-11, 2-13, 2-15, 2-18, 2-22, 3-3, 3-4, 3-6, 3-8, 3-25, 3-26, 3-37, 3-39, 3-41, 3-78, 3-79, 3-88, 3-89, 3-90, 3-91, 3-92, 3-93, 3-94, 3-95, 3-96, and 3-97. The most preferred compounds are Compounds No.:

1-1. 4-(1,2,3,4,10,14b-hexahydrodibenzo[c,f]pyrazino-[1,2-a]azepin-2-yl)butanoic acid;

1-3. 6-(1,2,3,4,10,14b-hexahydrodibenzo[c,f-]pyrazino[1,2-a]azepin-2-yl)hexanoic acid;

1-5. methyl 4-(1,2,3,4,10,14b-hexahydrodibenzo[c,f]-pyrazino[1,2-a]azepin-2-yl)butanoate;

1-9. ethyl 4-(1,2,3,4,10,14b-hexahydrodibenzo[c,f]-pyrazino[1,2-a]azepin-2-yl)butanoate;

1-11. ethyl 6-(1,2,3,4,10,14b-hexahydrodibenzo[c,f]-pyrazino[1,2-a]azepin-2-yl )hexanoate;

1-27. 2-(1,2,3,4,10,14b-hexahydrodibenzo[c,f]pyrazino-[1,2-a]azepin-2-yl)ethoxyacetic acid;

1-33. ethyl 2-(1,2,3,4,10,14b-hexahydrodibenzo[c,f]-pyrazino[1,2-a]azepin-2-yl)ethoxyacetate;

1-43. 2-(1,2,3,4,10,14b-hexahydrodibenzo[c,f]pyrazino-[1,2-a]azepin-2-yl)ethoxyacetamide;

1-54. α-[2-(1,2,3,4,10,14b-hexahydrodibenzo[c,f]-pyrazino[1,2-a]azepin-2-yl)ethoxy]-N,N-dipropylacetamide;

3-6. ethyl 4-(8-chloro-1,2,3,4,10,14b-hexahydrodibenzo-[c,f]pyrazino[1,2-a]azepin-2-yl)butanoate;

3-26. ethyl 4-(8-fluoro-1,2,3,4,10,14b-hexahydrodibenzo[c,f]pyrazino[1,2-a]azepin-2-yl)butanoate;

3-97. 4-(8-fluoro-1,2,3,4,10,14b-hexahydrodibenzo[c,f-]pyrazino[1,2-a]azepin-2-yl]butanoic acid.

The compounds of the present invention may be prepared by a variety of processes well known for the preparation of compounds of this type. In general terms one of the processes of the present invention comprises reacting a compound of formula (II):

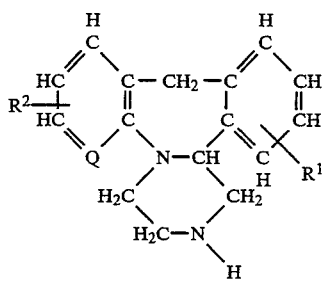

(in which R¹, R² and Q are as defined above) with a compound of formula (III):

$$R^3—X \quad (III)$$

(in which R³ is as defined above and X represents a halogen atom, preferably a chlorine, bromine or iodine atom), and then, if required, converting a group represented by R³ to any other group within the definition of R³. The reaction is normally and preferably effected in the presence of a base and of an inert solvent.

There is no particular limitation on the nature of the base used in this reaction, provided that it functions as a deacidifying reagent and has no adverse effect on any other part of the molecule. Examples of preferred bases include: organic amines, such as triethylamine, N-methylmorpholine, pyridine, 4-(N,N-dimethylamino)-pyridine, N,N-dimethylaniline and 1,8-diazabicyclo(5.4.0)undec-7-ene (DBU); and alkalis, including alkali metal and alkaline earth metal carbonates, hydrogencarbonates and hydroxides, such as sodium carbonate, potassium carbonate, sodium hydrogencarbonate, potassium hydrogencarbonate, sodium hydroxide, potassium hydroxide and barium hydroxide. Of these, we prefer the alkali metal carbonates and the alkali metal hydroxides.

There is no particular restriction on the nature of the solvent to be employed, provided that it has no adverse effect on the reaction or on the reagents involved. Examples of suitable solvents include: alcohols, such as methanol, ethanol and propanol; ketones, such as acetone, 2-butanone and 4-methyl-2-pentanone; and amides, especially fatty acid amides, such as dimethylformamide or dimethylacetamide. Of these, the ketones are most preferred.

The reaction can take place over a wide range of temperatures, and the precise reaction temperature is not critical to the invention. In general, we find it convenient to carry out the reaction at a temperature of from 0° C. to 150° C. (more preferably from 60° C. to 140° C.). The time required for the reaction may also vary widely, depending on many factors, notably the reaction temperature and the nature of the reagents. However, provided that the reaction is effected under the preferred conditions outlined above, a period of from 3 to 20 hours will usually suffice.

The reaction may be carried out in the presence of a small amount of an alkali metal iodide, such as sodium iodide or potassium iodide, which may function as a catalyst.

The compounds thus prepared can be recovered from the reaction mixture by conventional means. For example, the compounds may be recovered by distilling off the solvent from the reaction mixture or, if necessary, after distilling off the solvent from the reaction mixture, pouring the resulting residue into water and then extracting it with a water-immiscible organic solvent and finally distilling off the solvent from the extract. Moreover, if necessary, the resulting residue can be further purified by various well known techniques, such as recrystallization, reprecipitation or the various chromatography techniques, notably column chromatography or preparative thin layer chromatography.

Those compounds of formula (I) in which $R^3$ represents an alkyl group having a carboxy substituent or a group of formula —E—O—G—COOH (in which E and G are as defined above), i.e. carboxylic acids, can be prepared by hydrolysis of the corresponding compound in which $R^3$ represents an alkyl group having a substituent of formula —COOR$^{4a}$ or represents a group of formula —E—O—G—COOR$^{4a}$ (in which E and G are as defined above and R$^{4a}$ represents an alkyl group having from 1 to 6 carbon atoms, an aryl group or an aralkyl group), i.e. an ester.

The hydrolysis can be carried out by conventional means, for example, by reacting the corresponding ester with a base in an inert solvent.

There is no particular restriction on the nature of the base to be used in this hydrolysis reaction, and any base conventionally used in reactions of this type may equally be used here, provided that it has no adverse effect on other parts of the molecule. Examples of suitable bases include: alkali metal carbonates, such as sodium carbonate or potassium carbonate; and alkali and alkaline earth metal hydroxides, such as lithium hydroxide, sodium hydroxide, potassium hydroxide or barium hydroxide. Of these, the alkali metal hydroxides, such as sodium hydroxide and potassium hydroxide, are most preferred.

There is no particular restriction on the nature of the solvent to be employed, provided that it has no adverse effect on the reaction or on the reagents involved. Examples of suitable solvents include: alcohols, such as methanol, ethanol or propanol; ketones, such as acetone, 2-butanone or 4-methyl-2-pentanone; and ethers, such as dioxane or tetrahydrofuran. Of these, the alcohols are most preferred.

The reaction can take place over a wide range of temperatures, and the precise reaction temperature is not critical to the invention. In general, we find it convenient to carry out the reaction at a temperature of from 0° C. to 120° C.(more preferably from 0° C. to 80° C.). The time required for the reaction may also vary widely, depending on many factors, notably the reaction temperature and the nature of the reagents. However, provided that the reaction is effected under the preferred conditions outlined above, a period of from 1 hour to 10 hours will usually suffice.

The compound thus prepared may be recovered from the reaction mixture by conventional means. For example, the reaction mixture can be concentrated by distilling off the solvent or, if necessary, after distilling off the solvent from the reaction mixture, the resulting residue is poured into water and the aqueous layer is acidified. Alternatively, the acidified aqueous layer is extracted with a water-immiscible solvent, after which the desired compound can be obtained by distilling off the solvent from the extract. Additionally, the product can, if desired, be further purified by various well known techniques, such as recrystallization, reprecipitation or the various chromatography techniques, notably column chromatography or preparative thin layer chromatography.

Those compounds of formula (I) in which $R^3$ represents a group of formula —E—O—G—COOR$^4$ (in which E, G and R$^4$ are as defined above), can be prepared by reacting a corresponding compound of formula (I) in which $R^3$ represents a group of formula —E—OH (in which E is as defined above) with a compound having the general formula X—G—COOR$^4$ (IV) (in which G, R$^4$ and X are defined above) in an inert solvent.

This reaction is also preferably carried out in the presence of a base. There is no particular restriction on the nature of the base to be used in this reaction, and any base conventionally used in reactions of this type may equally be used here, provided that it has no adverse effect on other parts of the molecule. Examples of suitable bases include: alkali metal hydrides, such as sodium hydride and potassium hydride; alkyllithium compounds, such as methyllithium and butyllithium; and alkali metal alkoxides, such as sodium methoxide and sodium ethoxide. Of these, the alkali metal hydrides are preferred.

There is no particular restriction on the nature of the solvent to be employed, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, especially fatty acid amides, such as dimethylformamide and dimethylacetamide; and ethers, such as diethyl ether and tetrahydrofuran. Of these, the hydrocarbons are preferred.

The reaction can take place over a wide range of temperatures, and the precise reaction temperature is not critical to the invention. In general, we find it convenient to carry out the reaction at a temperature of from 0° C. to 150° C. (more preferably from room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary, after distilling off the solvent from the reaction mixture, pouring the residue into water followed by extraction with a water-immiscible organic solvent and distilling off the solvent from the extract. Additionally, the product can, if desired, be further purified by various well known techniques, such as recrystallization, reprecipitation or the various chromatography techniques, notably column chromatography or preparative thin layer chromatography.

Those compounds of formula (I) in which $R^3$ represents a group of formula —E—O—CONR$^{5a}$R$^{6a}$ (in which E is as defined above, and R$^{5a}$ and R$^{6a}$ can represent any of the groups or atoms represented by R$^5$ and R$^6$ other than a hydrogen atom) or a group of formula —E—O—CONHR$^{5a}$ (in which E and R$^{5a}$ are as defined above) can be prepared by reacting the corresponding compound of formula (I) in which $R^3$ represents a group of formula —E—OH with a compound of formula X—(C=O)—N(R$^{5a}$)R$^6$ or R$^{5a}$—NCO (in which R$^{5a}$, R$^6$ and X are as defined above) in an inert solvent and, if necessary, in the presence of a base.

Examples of the bases which may be used in this reaction are similar to those which can be used in the reaction of a compound of formula (II) with a compound of formula (III) as described above. Examples of suitable preferred bases include organic amines. Examples of inert solvents which may be used in this reaction are similar to those which can be used in the reaction of an ester with an amine, as described below, and examples of suitable preferred solvents include the halogenated hydrocarbons.

The reaction can take place over a wide range of temperatures, and the precise reaction temperature is not critical to the invention. In general, we find it convenient to carry out the reaction at a temperature of from 0° C. to 100° C. (more preferably from 0° C. to 40° C.). The time required for the reaction may also vary widely, depending on many factors, notably the reaction temperature and the nature of the reagents. However, provided that the reaction is effected under the preferred conditions outlined above, a period of from 5 minutes to 20 hours (more preferably from 10 minutes to 3 hours) will usually suffice.

Those compounds of formula (I) in which $R^3$ represents a group of formula —E—O—CONH$_2$ (in which E is as defined above) can be prepared by reacting the corresponding compound of formula (I) in which $R^3$ represents a group of formula —E—OH with a compound of formula $R^8$—NCO (in which $R^8$ represents an alkanoyl group having from 2 to 5 carbon atoms or a halogenated alkanoyl group having from 2 to 5 carbon atoms, such as an acetyl, propionyl, chloroacetyl, trichloroacetyl or trifluoroacetyl group, preferably a trichloroacetyl or trifluoroacetyl group) in an inert solvent, followed by removing the alkanoyl group from the resulting product.

Examples of inert solvents which may be used in this reaction are similar to those which can be used in the reaction of a compound of formula (II) with a compound of formula (III) as described above, and examples of suitable preferred solvents include the halogenated hydrocarbons.

The reaction can take place over a wide range of temperatures, and the precise reaction temperature is not critical to the invention. In general, we find it convenient to carry out the reaction at a temperature of from −20° C. to +50° C. (more preferably from −10° C. to room temperature). The time required for the reaction may also vary widely, depending on many factors, notably the reaction temperature and the nature of the reagents. However, provided that the reaction is effected under the preferred conditions outlined above, a period of from 30 minutes to 20 hours (more preferably from 1 hour to 5 hours) will usually suffice.

The reaction for the removal of the alkanoyl group is preferably carried out in an inert solvent and in the presence of a base or of an acid. Examples of suitable solvents are similar to those which may be used in the hydrolysis of a compound containing a group of formula —COOR$^{4a}$ (in which R$^{4a}$ is as defined above) and exemplified above, of which the alcohols are preferred.

Examples of suitable bases and acids which may be used in this reaction include: alkali metal hydroxides, such as sodium hydroxide or potassium hydroxide; alkali metal carbonates, such as sodium carbonate or potassium carbonate; alkali metal hydrogencarbonates, such as sodium hydrogencarbonate or potassium hydrogencarbonate; mineral acids, such as hydrochloric acid or sulfuric acid; acidic silica gel; and acidic alumina. Of these, we prefer weak bases and acids, such as the alkali metal carbonates, alkali metal hydrogencarbonates, dilute mineral acids and acidic silica gel.

The reaction can take place over a wide range of temperatures, and the precise reaction temperature is not critical to the invention. In general, we find it convenient to carry out the reaction at about room temperature. The time required for the reaction may also vary widely, depending on many factors, notably the reaction temperature and the nature of the reagents. However, provided that the reaction is effected under the preferred conditions outlined above, a period of from 1 to 24 hours will usually suffice.

The compound thus prepared may be recovered from the reaction mixture by conventional means. For example, the compounds may be recovered by distilling off the solvent from the reaction mixture or, if necessary, after distilling off the solvent from the reaction mixture, pouring the residue into water followed by extraction with a water-immiscible organic solvent and distilling off the solvent from the extract. Additionally, the product can, if desired, be further purified by various well known techniques, such as recrystallization, reprecipitation or the various chromatography techniques, notably column chromatography or preparative thin layer chromatography.

Those compounds of formula (I) in which $R^3$ represents a group of formula —E—O—G—CONR$^5$R$^6$ (in which E, G, R$^5$ and R$^6$ are as defined above) can be prepared by reacting a compound of formula (I) in which $R^3$ represents a group of formula —E—O—G—COOR$^4$ (in which E, G, and R$^4$ are as defined above) with an amine compound of formula HNR$^5$R$^6$ (in which R$^5$ and R$^6$ are as defined above).

Where R$^4$ represents R$^{4a}$, i e. an alkyl aryl or aralkyl group, this reaction is preferably carried out in an inert solvent.

There is no particular restriction on the nature of the solvent to be employed, provided that it has no adverse effect on the reaction or on the reagents involved. Examples of suitable solvents include: halogenated hydrocarbons, especially halogenated aliphatic hydrocarbons, such as methylene chloride, dichloroethane or chloroform; ethers, such as diethyl ether, tetrahydrofuran or dioxane; esters, such as ethyl acetate; and aromatic hydrocarbons, such as benzene, toluene or xylene. Of these, the aromatic hydrocarbons or ethers are most preferred.

Likewise, a large excess amount of the amino compound of formula HNR$^5$R$^6$ can serve both as a solvent and as a reagent.

The reaction can take place over a wide range of temperatures, and the precise reaction temperature is not critical to the invention. In general, we find it convenient to carry out the reaction at a temperature of from −10° C. to 150° C. (more preferably from 0° C. to 50° C.). The time required for the reaction may also vary widely, depending on many factors, notably the reaction temperature and the nature of the reagents. However, provided that the reaction is effected under the preferred conditions outlined above, a period of from 5 minutes to 20 hours (more preferably from 30 minutes to 10 hours) will usually suffice.

Where R$^4$ represents a hydrogen atom, this reaction is preferably carried out in an inert solvent and in the presence of a condensing agent.

There is no particular limitation on the nature of the condensing agent to be used in this reaction, provided that it can be used for preparing an amide bond from a carboxylic acid and an amine and any condensing agent conventionally used in reactions of this type may equally be used here. Examples of preferred condensing agent include: dicyclohexylcarbodiimide (DCC), diethyl cyanophosphonate (DEPC)-triethylamine, carbonyldiimidazole, diphenylphosphoryl azide (DPPA)-triethylamine and diethyl azodicarboxylate-triphenylphosphine.

There is no particular restriction on the nature of the solvent to be employed, provided that it has no adverse effect on the reaction or on the reagents involved. Examples of suitable solvents include: aromatic hydrocarbons, such as benzene, toluene or xylene; halogenated hydrocarbons, especially halogenated aliphatic hydrocarbons, such as methylene chloride or chloroform; esters, such as ethyl acetate or propyl acetate; ethers, such as diethyl ether, tetrahydrofuran or dioxane; amides, especially fatty acid amides, such as dimethylformamide, dimethylacetamide or hexamethylphosphoric triamide; and sulfoxides, such as dimethyl sulfoxide. Of these, the ethers (particularly tetrahydrofuran), halogenated hydrocarbons (particularly methylene chloride), amides (particularly dimethylformamide) and esters (particularly ethyl acetate) are most preferred.

The reaction can take place over a wide range of temperatures, and the precise reaction temperature is not critical to the invention. In general, we find it convenient to carry out the reaction at a temperature of from 0° C. to 150° C. (more preferably from 0° C. to 50° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

Where $R^4$ represents a hydrogen atom, the desired compound can also be prepared by converting the corresponding carboxylic acid to a reactive derivative thereof, followed by reacting it with an amino compound of formula $HNR^5R^6$.

Examples of suitable reactive derivatives of the carboxylic acid include: acid halides, such as acid chlorides or acid bromides; acid azides; reactive esters prepared from N-hydroxybenzotriazole or N-hydroxysuccinimide; acid anhydrides of the carboxylic acid used; and mixed anhydrides with a monoalkyl carbonate in which the alkyl group has from 1 to 4 carbon atoms (such as monomethyl carbonate, monoethyl carbonate or monoisobutyl carbonate) or with a monoaryl carbonate (such as monophenyl carbonate or monotolyl carbonate). Of these, the mixed acid anhydrides with alkyl carbonates are most preferred. The reactive derivative of the carboxylic acid, such as the acid halide or acid anhydride, can be prepared by conventional means, for example, by reacting the carboxylic acid with a halide (e.g. thionyl chloride, thionyl bromide, an acid chloride or acid bromide of the desired carboxylic acid, methyl chloroformate, ethyl chloroformate, isobutyl chloroformate, phenyl chloroformate, tolyl chloroformate etc. ) at a temperature of from 20° C. to 100° C. for a period of from 1 hour to 20 hours in an inert solvent (e.g. methylene chloride, benzene, tetrahydrofuran etc. ), if necessary, in the presence of a base (e.g. pyridine, triethylamine, dimethylaniline etc. ). Other reactive derivatives of the carboxylic acids, such as acid amides or reactive esters, can be prepared by reacting the carboxylic acid with the corresponding compound (e.g. hydrogen azide, N-hydroxybenzotriazole, N-hydroxysuccinimide etc. ) using a conventional reaction for preparing an amide bond from the said carboxylic acid and an amine.

The reaction of a reactive derivative of the carboxylic acid with the amino compound of formula $HNR^5R^6$ can be carried out in a similar manner to the reaction of the compound of formula (II) with a compound of formula (III).

Those compounds of formula (I) in which $R^3$ represents a group of $-J-CH(OH)-CH_2-NR^5R^6$ (in which J, $R^5$ and $R^6$ are as defined above) can be prepared by reacting ,the compound of formula (II) with a compound of formula (V):

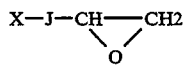   (V)

(in which J and X are as defined above) and subsequently reacting the resulting compound in which $R^3$ represents a group of formula

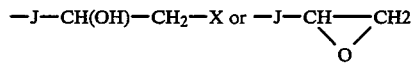

(in which J and X are as defined above), with the amino compound of formula $HNR^5R^6$ The reaction of the compound of formula (II) with a compound of formula (V) is similar to that between the compound of formula (II) and the compound of formula (III), and the reaction of the compound of formula (I) in which $R^3$ represents a group of formula

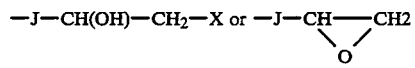

with the amino compound of formula $HNR^5R^6$ can be carried out in a similar manner to the reaction of a compound of formula (II) with a compound of formula (III).

The compounds of general formula (II) are well known or can be prepared by processes analogous to the known methods, which are described, for example, in: C. N. Filer et al., J. Org. Chem., .46, 3344 (1981); C. A. A. van Boeckel et al., Recl. Trav. Chim. Pays Bas, 104, 259 (1985); and A. Org-Lee et al J. Heterocyclic Chem., 20, 1565 (1983 ), of which the disclosures are incorporated herein by reference.

Likewise, in general, the starting materials of formula (III) are known or can be prepared by methods known for the preparation of analogous known compounds.

However, a compound of formula (III) wherein $R^3$ represents a group of formula $-E-O-G'-COOR^4$ in which E and $R^4$ are as defined above and $G'$ represents an alkylene or alkylidene group having from 1 to 9 carbon atoms, i.e. a compound of formula (III'), can alternatively be prepared by the following reaction:

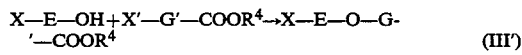   (III')

In the above formulae, $R^4$, E, $G'$ and X are as defined above and $X'$ represents a halogen atom, preferably a bromine or iodine atom.

The reaction is normally and preferably effected in the presence of a base and of a solvent.

There is no particular restriction on the nature of the base which may be used, provided that it has no adverse effect on any other part of the molecule of either reagent, and any base commonly used for reactions of this type may equally be used here. Examples of suitable bases include; alkali metal hydrides, such as lithium hydride, sodium hydride and potassium hydride; alkali metals such as sodium and potassium; alkali or alkaline earth metal carbonates, such as lithium carbonate, sodium carbonate, potassium carbonate and barium carbonate; alkali metal hydrogencarbonates, such as sodium hydrogencarbonate and potassium hydrogencarbonate; alkali metal alkoxides, such as sodium methoxide, sodium ethoxide and potassium t-butoxide; and organic amines, such as triethylamine, pyridine, 4-dimethylaminopyridine and DBU. Of these, the alkali metal hydrides and alkali metals are preferred.

There is no particular restriction on the nature of the solvent to be employed, provided that it has no adverse effect on the reaction or on the reagents involved. Examples of suitable solvents include: aliphatic hydrocarbons, such as pentane and hexane; alicyclic hydrocarbons, such as cyclohexane; aromatic hydrocarbons, such as benzene, toluene and xylene; ethers, such as diethyl ether, tetrahydrofuran and dioxane; amides, especially fatty acid amides, such as dimethylformamide and dimethylacetamide; and ketones, such as acetone, methyl ethyl ketone and methyl isobutyl ketone. A single one of these solvents or a-mixture of any two or more of them may be employed. Of these, we prefer the aliphatic hydrocarbons, cyclic hydrocarbons, aromatic hydrocarbons, ethers and amides.

The reaction can take place over a wide range of temperatures, and the precise reaction temperature is not critical to the invention. In general, we find it convenient to carry out the reaction at a temperature of from $-110°$ C. to $130°$ C., more preferably at from $-50°$ C. to about room temperature and still more preferably by raising the temperature stepwise to $-50°$ C. $-20°$ C., $-10°$ C. $-10°$ C. and room temperature, However, the preferred reaction temperature may vary depending on the nature of the starting materials. The time required for the reaction may also vary widely, depending on many factors, notably the reaction temperature and the nature of the reagents. However, provided that the reaction is effected under the preferred conditions outlined above, a period of from 1 hour to 20 hours (more preferably from 1 hour to 6 hours) will usually suffice.

After completion of the reaction, the product may be recovered from the reaction mixture by conventional means, for example by evaporating the solvent under reduced pressure, if necessary after removing insoluble material by filtration, or by adding water to the residue, extracting it with a water-immiscible organic solvent, and finally distilling off the solvent. After this, the product may, if desired, be purified by such conventional means as recrystallization or the various chromatography techniques, notably preparative thin layer chromatography or column chromatography.

A compound of formula (III') where $R^4$ represents a hydrogen atom can be prepared by hydrolysis of the ester of formula (III') where $R^4$ is $R^{4a}$ in similar manner to that described previously.

Optically active compounds of formula (II) can be prepared by either of the following two methods.

METHOD A

Method A comprises the acylation of a racemic compound of formula (II), the optical resolution of the resulting acyl derivative and the deacylation of the optically active acyl derivative.

(a) Acylation

Acylation of a racemic compound of formula (II) can be carried out by reacting the racemic compound of formula (II) with an acylating agent in the presence of a base and of an inert solvent in a similar manner to the reaction of the compound of formula (I) where $R^3$ represents a group of formula —E—O—G—COOR$^4$ with an amine of formula HNR$^5$R$^6$ as described above.

Examples of acylating agent which may be employed in this reaction include optically active carboxylic acids and reactive derivatives thereof, such as (+) or (−)-α-methoxy-α-trifluoromethyl-phenylacetic acid, (+) or (−)-α-methoxy-α-methyl-phenylacetic acid, (+) or (−)-mandelic acid, (+) and (−)-phenylethanesulfonic acid, (+) or (−)-cis-2-benzamidocyclohexane carboxylic acid, (+) or (−)-2,2'-(1,1'-binaphthyl)phosphoric acid, acid chlorides of these carboxylic acids and (+) or (−)-trans-1,2-cyclohexanedicarboxylic anhydride, preferably (+) or (−)-α-methoxy-α-trifluoromethylphenylacetyl chloride and (+) or (−)-α-methoxy-α-methyl-phenylacetyl chloride.

(b) Optical Resolution

Optical resolution of the acylated compound prepared in step (a) can be carried out by well known techniques, such as recrystallization or the various chromatography techniques, notably column chromatography or preparative thin layer chromatography.

(c) Deacylation

Deacylation of the optically active acyl derivatives can be carried out by hydrolysis or by reduction of the acyl derivatives. The hydrolysis can be carried out in a similar manner to the reaction of the compound of formula (I) where $R^3$ represents a group of formula —E—O—G—COOR$^{4a}$ (in which R$^{4a}$ is as defined above) to give the corresponding carboxylic acid.

Alternatively, the reduction may be carried out by any method known for reducing compounds of this type, but is preferably carried out using a reducing agent in the presence of an inert solvent.

Examples of suitable reducing agents which may be employed in this reaction include aluminum hydride compounds, such as lithium aluminum hydride, diisobutyl aluminum hydride and lithium tri-t-butoxyaluminum hydride, preferably diisobutyl aluminum hydride.

There is no particular restriction on the nature of the solvent to be employed, provided that it has no adverse effect on the reaction or on the reagents involved. Examples of suitable solvents include: aliphatic hydrocarbons, such as pentane and hexane; alicyclic hydrocarbons, such as cyclohexane; aromatic hydrocarbons, such as benzene, toluene and xylene; and ethers, such as diethyl ether, tetrahydrofuran and dioxane. A single one of these solvents or a mixture of any two or more of them may be employed. Of these, we prefer the aliphatic hydrocarbons, cyclic hydrocarbons and aromatic hydrocarbons.

The reaction can take place over a wide range of temperatures, and the precise reaction temperature is not critical to the invention. In general, we find it convenient to carry out the reaction at a temperature of from $-110°$ C. to $-30°$ C., more preferably at from $-78°$ C. to $-50°$ C. The time required for the reaction may also vary widely, depending on many factors, notably the reaction temperature and the nature of the reagents. However, provided that the reaction is effected under the preferred conditions outlined above, a period of from 30 minutes to 10 hours (more preferably from 1 hour to 5 hours) will usually suffice.

METHOD B

Method B comprises the optical resolution of a racemic compound of formula (A), as defined above in relation to the prior art, and demethylation of the optically active compound of formula (A).

(a) Optical Resolution

Optical resolution of the racemic compound of formula (A) can be carried out by treating the racemic compound of formula (A) with an optically active carboxylic acid in an inert solvent to give a mixture of diastereomeric salts, separating the mixture of diastereomeric salts to give an optically active salt and recovering the optically active compound of formula (II).

Examples of optically active carboxylic acids which may be employed in this step include: (+)-tartaric acid, (−)-dibenzoyltartaric acid, (−)-diacetyltartaric acid, (−)-ditoluoyltartaric acid, (−)-malic acid, (+)-10-camphorsulfonic acid, (+)-camphoric acid, (−)-pyroglutamic acid, (+)-aspartic acid, (+)-phenylethanecarboxylic acid, (+)-mandelic acid, (+)-cis-2-benzamidocyclohexanecarboxylic acid, (+)-2,2'-(1,1'-binaphthyl)phosphoric acid and optical isomers thereof, preferably (−)-dibenzoyltartaric acid, (−)-diacetyltartaric acid, (−)-ditoluoyltartaric acid or (−)-malic acid.

Examples of inert solvents which may be employed in this step include: water; alcohols, such as methanol, ethanol, propanol and isopropanol; ethers, such as tetrahydrofuran and dioxane; ketones, such as acetone, methyl ethyl ketone and 4-methyl-2-pentanone; and amides, especially fatty acid amides, such as dimethylformamide and dimethylacetamide. A single one of these solvents or a mixture of any two or more of them may be employed. Of these, we prefer the alcohols. Also, when alcohols are employed as the inert solvent, an optically active salt can be separated simply by filtration.

The reaction can take place over a wide range of temperatures, but we generally find that about room temperature is convenient. The time required for the treatment may also vary widely, depending on many factors, notably the reaction temperature and the nature of the reagents. However, provided that the reaction is effected under the preferred conditions outlined above, a period of from 10 minutes to 2 hours will usually suffice.

Separation of the mixture of diastereomeric salts can be carried out by conventional means, for example by filtering off an optically active salt or by recrystallizing the mixture from a solvent, such as the alcohols and amides above.

Recovery of an optically active compound of formula (II) from the optically active salt can be carried out by conventional means, for example by dissolving the optically active salt in an alkaline solution (such as an aqueous solution of sodium hydroxide, potassium hydroxide, sodium carbonate, potassium carbonate, sodium hydrogencarbonate or potassium hydrogencarbonate), extracting it with a water-immiscible organic solvent and finally distilling off the solvent.

(b) Demethylation

Demethylation of the optically active compound of formula (A) can be carried out in a similar manner to the known methods, which are described, for example, in: Recl. Trav. Chim. Pays-Bas, 104, 259 (1985).

After completion of any of the above reactions, the desired compounds can be recovered from the reaction mixture by conventional means. For example, the compounds may be recovered by distilling off the solvent from the reaction mixture or, if necessary, after distilling off the solvent from the reaction mixture, pouring the residue into water followed by extraction with a water-immiscible organic solvent and distilling off the solvent from the extract. Additionally, the product can, if desired, be further purified by various well known techniques, such as recrystallization, reprecipitation or the various chromatography techniques, notably column chromatography or preparative thin layer chromatography.

The hetero-tetracyclic compounds of the present invention have, as shown in the following biological activity data, exhibited excellent anti-histamic, anti-allergic and anti-asthmatic activities and an excellent inhibitory activity against the production of SRS-A. Accordingly, the compounds are useful as therapeutic agents for the treatment or prophylaxis of allergic diseases or asthma.

The compounds of the present invention may therefore be used in the treatment of such disorders, and, for this purpose, may be formulated as conventional pharmaceutical preparations, as is well known in the art. Thus, the compounds may be administered orally, e.g. in the form of tablets, capsules, granules, powders, syrups, sprays or other such well known forms, or parenterally, e.g. by injections, sprays, eyedrops, adhesive plasters or suppositories, etc.

These pharmaceutical preparations can be prepared by conventional means and may contain known adjuvants of a type commonly used in this field, for example vehicles, binders, disintegrators, lubricants, stabilizers, corrigents, etc. depending upon the intended use and form of the preparation. The dose will depend upon the condition, age, and body weight of the patient as well as upon the nature and severity of the disorder to be treated, but in the case of oral administration to an adult human patient, we would normally suggest a total daily dose of from 0.01 mg to 100 mg (more preferably from 0.1 mg to 50 mg), which may be administered in a single dose or in divided doses, e.g. from one to three times a day.

The preparation of the compounds of the present invention is further illustrated by the following Examples, and the preparation of certain of the compounds used as starting materials in some of these Examples is illustrated in the subsequent Preparations. The biological activity of certain of the compounds of the present invention is illustrated in the following Test Examples.

EXAMPLE 1

Ethyl 2-(1,2,3,4,10,14b-hexahydrodibenzo[c,f]pyrazino-[1,2-a]azepin-2-yl)ethoxyacetate 2.5 g of 1,2,3,4,10,14b-hexahydrodibenzo[c,f]-pyrazino[1,2-a]azepine, 2.4 g of ethyl 2-chloroethoxyacetate (prepared as described in Preparation 1 or 2), 3.82 g of sodium carbonate and 0.14 g of sodium iodide were added to 80 ml of 4-methyl-2-pentanone, and the mixture was heated under reflux for 18 hours. At the end of this time, it was filtered, and the solvent was removed from the filtrate by distillation under reduced pressure. The residue was subjected to column chromatography through silica gel, and 3.2 g (yield 84%) of the title compound were obtained as a light brown oil from the fractions eluted with ethyl acetate.

Infrared Absorption Spectrum (CHCl$_3$), $\nu_{max}$ cm$^{-1}$: 1495, 1750, 2830, 2950.

An equimolar amount of oxalic acid was added to a solution of the title compound in ethanol, and the mixture was stirred at room temperature for 30 minutes. At the end of this time, the solvent was removed by evaporation under reduced pressure, and the residue was recrystallized from ethanol, to give the oxalate of the title compound, melting at 141°–144 ° C.

EXAMPLE 2
2-(1,2,3,4,10,14b-Hexahydrodibenzo[c,f]pyrazino[1,2-a]azepin-2-yl)ethoxyacetic acid 7 ml of a 10 % w/v aqueous solution of sodium hydroxide and 10 ml of water were added to a solution of 3.2 g of ethyl 2-(1,2,3,4,10,14b-hexahydrodibenzo[c,f]pyrazino[1,2-a]azepin-2-yl)ethoxyacetate (prepared as described in Example 1) dissolved in 20 ml of ethanol. The mixture was then stirred at room temperature for 1 hour, after which it was concentrated to about one half of its original volume by distillation under reduced pressure. The pH of the concentrate was then adjusted to a value of 4.0 by the addition of 10% w/v aqueous hydrochloric acid, and the mixture was extracted with chloroform. Concentration of the extract by evaporation under reduced pressure yielded 2.96 g (a quantitative yield) of the title compound as a foamy substance, which was recrystallized from water to give colorless needles, melting at 135° C. (with decomposition).

Infrared Absorption Spectrum (KBr), $\nu_{max}$ cm$^{-1}$: 1426, 1450, 1491, 1602, 2820, 2940.

The following salts of this compound were then prepared by similar means to those described in Example 1:
Sodium salt, melting at 140°–145° C. (with decomposition);
Fumarate, melting at 187°–188° C. (with decomposition);
Oxalate, melting at 184°–186° C. (with decomposition).

EXAMPLE 3
Methyl 2-(1,2,3,4,10,14b-hexahydrodibenzo[c,f]pyrazino[1,2-a]azepin-2-yl)ethoxyacetate 3(a)  2-(1,2,3,4,10,14b-Hexahydrodibenzo[c,f]pyrazino[1,2-a]azepin-2-yl)ethanol 2 g Of 1,2,3,4,10,14b-hexahydrobenzo[c,f]pyrazino[1,2-a]azepine, 0.84 g of 2-chloroethanol, 3.09 g of potassium carbonate and 0.13 g of sodium iodide were added to 30 ml of ethanol, and the mixture was heated under reflux for 16 hours. At the end of this time, it was filtered, and the solvent was removed from the filtrate by distillation under reduced pressure, to afford 1.81 g (yield 77%) of the title compound, melting at 123°–125° C.

Infrared Absorption Spectrum (KBr), $\nu_{max}$ cm$^{-1}$: 1446, 1491, 2810, 3300, 3380.

The hydrochloride of this compound, melting at 252°–254° C. (with decomposition), was prepared by similar means to those described in Example 17.

Alternatively, the same compound may be prepared by the following Examples 3(b) and 3(c).

3(b)  Ethyl (1,2,3,4,10,14b-hexahydrodibenzo[c,f]pyrazino [1,2-a]azepin-2-yl) acetate 0.546 g of 1,2,3,4,10,14b-hexahydrodibenzo[c,f]pyrazino[1,2-a]azepine, 0.437 g of ethyl bromoacetate, 0.692 g of sodium carbonate and 0.016 g of sodium iodide were added to 20 ml of 4-methyl-2-pentanone, and the mixture was heated under reflux for 16 hours. At the end of this time, the mixture was diluted with water and then extracted with ethyl acetate. The solvent was then removed by evaporation under reduced pressure. The resulting residue was then subjected to column chromatography through silica gel, using a 4:1 by volume mixture of hexane and ethyl acetate as the eluent, to afford 0.602 g (yield 82%) of the title compound as a pale yellow oil. The hydrochloride of this compound, melting at 187°–190° C., may be prepared by similar means to those described in Example 17.

Infrared Absorption Spectrum (KBr), $\nu_{max}$ cm$^{-1}$: 1450, 1550, 1600, 1745, 2870, 2950.

3(c)  2-(1,2,3,4,10,14b-Hexahydrodibenzo[c,f]pyrazino[1,2-a]azepin-2-yl)ethanol

A suspension of 0.251 g of lithium aluminum hydride in 20 ml of tetrahydrofuran was added, whilst ice-cooling, over a period of 10 minutes to a solution of 2.22 g of ethyl (1,2,3,4,10,14b-hexahydrodibenzo[c,f]pyrazino[1,2-a]azepin-2-yl)acetate [prepared by the same procedure as described in Example 3(b)] dissolved in 15 ml of tetrahydrofuran, under an atmosphere of nitrogen. The mixture was then stirred at 0° C. for 30 minutes and at room temperature for 2 hours, after which 2 ml of a saturated aqueous solution of ammonium chloride were added. The mixture was filtered, and the filtrate was extracted with ethyl acetate. The extract was washed with water and concentrated by evaporation under reduced pressure, to afford 1.65 g (yield 85%) of the title compound, melting at 123°–125 ° C.

3(d) Methyl 2-(1,2,3,4,10,14b-hexahydrodibenzo[c,f]pyrazino[1,2-a]azepin-2-yl)ethoxyacetate 0.478 g of a 55% w/w dispersion of sodium hydride in mineral oil was added to a solution of 1.5 g of 2-(1,2,3,4,10,14b-hexahydrodibenzo[c,f]pyrazino[1,2-a]azepin-2-yl)ethanol [prepared as described in step (a) or (c) above] dissolved in 20 ml of toluene, under an atmosphere of nitrogen. The mixture was then stirred at 40° C. for 2 hours, after which 0.924 g of methyl bromoacetate was added, whilst ice-cooling; the mixture was then stirred at 40° C. for a further 4 hours. At the end of this time, the reaction-mixture was filtered and the filtrate was concentrated by evaporation under reduced pressure. The residue was subjected to column chromatography through silica gel, using a 1:1 by volume mixture of hexane and ethyl acetate as the eluent, to afford 0.58 g (31% yield) of the title compound as an oil.

Infrared Absorption Spectrum (CHCl$_3$) $\nu_{max}$ cm$^{-1}$: 1450, 1495, 1600, 1755, 2820, 2950, 3000.

The fumarate, melting at 135° C. (with decomposition), may be prepared from this compound by similar means to those described in Example 1.

EXAMPLE 4

Ethyl 2-(8-chloro-1,2,3,4,10,14b-hexahydrodibenzo[c,f-]pyrazino1,2-a)azepin-2-yl)ethoxyacetate Following a procedure similar to that described in Example 1, but using 8-chloro-1,2,3,4,10,14b-hexahydrodibenzo[c,f]pyrazino[1,2-a]azepine, the title compound was obtained in a yield of 52%.

Infrared Absorption Spectrum (CHCl$_3$), $v_{max}$ cm$^{-1}$: —1490, 1600, 1745, 2820, 2950.

Following a procedure similar to that described in Example 1, the oxalate of the title compound, melting at 191°–192° C. (with decomposition), was also obtained.

EXAMPLE 5

Methyl 2-(8-bromo-1,2,3,4,10,14b-hexahydrodibenzo[c,f-]pyrazino[1,2-a]azepin-2-yl)ethoxyacetate Following a procedure similar to that described in Example 1, but using 8-bromo-1,2,3,4,10,14b-hexahydrodibenzo[c,f]pyrazino[1,2-a]azepine and methyl 2-chloroethoxyacetate, the title compound was obtained in a yield of 38%.

Infrared Absorption Spectrum (CHCl$_3$), $v_{max}$ cm$_{-1}$: 1455, 1490, 1715, 1760, 2850, 2975.

Following a procedure similar to that described in Example 1, the oxalate of the title compound, melting at 183°–185° C. (with decomposition), was also prepared.

EXAMPLE 6

2-[2-(2-Hydroxyethoxy)ethyl]-1,2,3,4,10,14b-hexahydrodibenzo[c,f]pyrazino[1,2-a]azepine Following a procedure similar to that described in Example 1, but using 2-(2-hydroxyethoxy)ethyl chloride, the title compound was obtained in a yield of 65%.

Infrared Absorption Spectrum (CHCl$_3$), $v_{max}$ cm$^{-1}$: 1455, 1500, 1600, 2850, 2960.

Following a procedure similar to that described in Example 1, the fumarate, melting at 145°–159° C. (with decomposition), was also prepared.

EXAMPLE 7

2-{2-[2-(2-Hydroxyethoxy)ethoxy]ethyl}-1,2,3,4,10,14b-hexahydrodibenzo[c,f]pyrazino[1,2-a)azepine Following a procedure similar to that described in Example 1, but using 2-[2-(2-hydroxyethoxy)ethoxy]ethyl chloride, the title compound was obtained in a yield of 83%.

Following a procedure similar to that described in Example 1, the oxalate, melting at 82°–85° C. (with decomposition), was also prepared.

EXAMPLE 8

Methyl 2-(1,2,3,4,10,14b-hexahydrobenzo[c]pyrazino[1,2-a]pyrido[5,6-c]azepin-2-yl)ethoxyacetate Following a procedure similar to that described in Example 1, but using 1,2,3,4,10,14b-hexahydrobenzo[c]pyrazino[1,2-a]pyrido[5,6-c]azepine and methyl 2-chloroethoxyacetate, the title compound was obtained in a yield of 67%.

Infrared Absorption Spectrum (CHCl$_3$), $v_{max}$ cm$^{-1}$: 1455, 1595, 1755, 2970.

Following a procedure similar to that described in Example 1, the oxalate, melting at 130°–132° C. (with decomposition), was also prepared.

EXAMPLES 9 to 11

Using a procedure similar to that described in Example 2, the following compounds were synthesized from the corresponding compound of Example 4, 5 or 8, respectively.

EXAMPLE 9

2-(8-Chloro-1,2,3,4,10,14b-hexahydrodibenzo[c,f-]pyrazino1,2-a]azepin-2-yl)ethoxyacetic acid in a yield of 94%.

Infrared Absorption Spectrum (KBr), $v_{max}$ cm$^{-1}$: 1488, 1586, 2360, 2480, 2840, 2900, 2950.

The oxalate of the title compound, melting at 167°–169° C. (with decomposition), was also prepared.

EXAMPLE 10

2-(8-Bromo-1,2,3,4,10,14b-hexahydrodibenzo[c,f-]pyrazino1,2-a]azepin-2-yl)ethoxyacetic acid in a quantitative yield.

Infrared Absorption Spectrum (KBr), $v_{max}$ cm$^{-1}$: 1426, 1450, 1490, 1600, 2830, 2940.

The oxalate of the title compound, melting at 177°–178° C. (with decomposition), was also prepared.

EXAMPLE 11

2-(1,2,3,4,10,14b-Hexahydrobenzo[c]pyrazino[1,2-a]pyrido5,6-c]azepin-2-yl)ethoxyacetic acid in a yield of 72%.

Infrared Absorption Spectrum (KBr), $v_{max}$ cm$^{-1}$: 1445, 1500, 1600, 2460, 2970.

The oxalate of the title compound, melting at 197°–198° C. (with decomposition), was also prepared.

EXAMPLES 12 and 13

Using a procedure similar to that described in Example 3(d), the following compounds were synthesized from the corresponding compounds of Examples 6 and 7, respectively.

EXAMPLE 12

Ethyl 2-{2-(1,2,3,4,10,14b-hexahydrodibenzo[c,f-]pyrazino[1,2-a]azepin-2-yl)ethoxy}ethoxyacetate, in a yield of 35%.

Infrared Absorption Spectrum (CHCl$_3$), $v_{max}$ cm$^{-1}$: 1495, 1600, 1750, 2825, 2950, 3010. Mass Spectrum (m/z): 424 (56, M+), 263 (100).

EXAMPLE 13

Ethyl 2-{2-[2-(1,2,3,4,10,14b-hexahydrodibenzo[c,f-]pyrazino [1,2-a]azepin-2-yl)ethoxy]ethoxy}ethoxyacetate, in a yield of 24%.

Infrared Absorption Spectrum (CHCl$_3$), $v_{max}$ cm$^{-1}$: 1450, 1490, 1600, 1750, 2820. Mass Spectrum (m/z): 468 (29, M+), 263 (100).

EXAMPLES 14 and 15

Using a procedure similar to that described in Example 2, the following compounds were synthesized from the corresponding compound of Example 12 or 13, respectively.

EXAMPLE 14

2-{2-(1,2,3,4,10,14b-Hexahydrodibenzo[c,f-]pyrazino[1,2-a]azepin-2-yl)ethoxy}ethoxyacetic acid in a quantitative yield.

Infrared Absorption Spectrum (CHCl$_3$), $v_{max}$ cm$^{-1}$: 1455, 1500, 1600, 1740, 2460, 2980.

The fumarate of the title compound, melting at 169°–172° C. (with decomposition), was also prepared.

EXAMPLE 15

2-{2-[2-(1,2,3,4,10,14b-Hexahydrodibenzo[c,f-]pyrazino[1,2-a]azepin-2-yl)ethoxy]ethoxy}ethoxyacetic acid in a yield of 97%.

Infrared Absorption Spectrum (CHCl$_3$), $v_{max}$ cm$^{-}$: 1455, 1495, 1600, 2810, 2960, 3010.

The hydrochloride of the title compound, melting at 130°–133° C. (with decomposition), was also prepared.

EXAMPLE 16

3-(1,2,3,4,14b-Hexahydrodibenzo[c,f]pyrazino[1,2-a]azepin-2-yl)propanol 1.5 g of 1,2,3,4,10,14b-hexahydrodibenzo[c,f-]pyrazino [1,2-a]azepine, 0.74 g of 3-chloropropanol, 2.32 g of potassium carbonate and 0.10 g of sodium iodide were added to 30 ml of ethanol, and the mixture was heated under reflux for 20 hours. At the end of this time, the reaction mixture was filtered, and then the solvent was removed from the filtrate by distillation under reduced pressure. The residue was then subjected to column chromatography through silica gel, and the desired compound was obtained as crystals from the fractions eluted with 5% by volume ethanol in chloroform; it was then recrystallized from ethyl acetate, to afford 1.28 g (69% yield) of the title compound, melting at 127°–128° C.

Infrared Absorption Spectrum (KBr) $v_{max}$ cm$^{-1}$: 1448, 1492, 2821, 2895, 2956, 3194.

EXAMPLES 17 and 18

Following the procedure described in Example 16, but using 4-chlorobutanol or 6-chlorohexanol, the following compounds were synthesized:

EXAMPLE 17

4-(1,2,3,4,10,14b-Hexahydrodibenzo[c,f]pyrazino[1,2-a]azepin-2-yl)butanol, in a yield of 51%.

Infrared Absorption Spectrum (CHCl$_3$) $v_{max}$ cm$^{-1}$: 1450, 1495, 1600, 2830, 2950.

The title compound was then dissolved in ethyl acetate, and a 4N solution of hydrogen chloride in ethyl acetate was added to the resulting solution. The solvent was then removed by distillation under reduced pressure, to afford the hydrochloride of the title compound, melting at 233°–235° C. (with decomposition).

EXAMPLE 18

6-(1,2,3,4,10,14b-Hexahydrodibenzo[c,f]pyrazino[1,2-a]azepin-2-yl)hexanol, in a yield of 34%.

Infrared Absorption Spectrum (KBr) $v_{max}$ cm$^{-1}$: 1440, 1494, 1590, 2813, 2837, 2944, 3204.

The hydrochloride of the title compound, melting at 192°–193° C. (with decomposition), was also prepared.

EXAMPLES 19 to 21

Following a procedure similar to that described in Example 3(i), but using the corresponding bromoester, the following compounds were synthesized and then their salts were prepared.

EXAMPLE 19

Ethyl 4-(1,2,3,4,10,14b-hexahydrodibenzo[c,f-]pyrazino[1,2-a]azepin-2-yl)butanoate, in a yield of 94%.

Infrared Absorption Spectrum (CHCl$_3$) $v_{max}$ cm$^{-1}$: 1450, 1500, 1600, 1735, 2840, 2960.

EXAMPLE 20

Ethyl 5-(1,2,3,4,10,14b-hexahydrodibenzo[c,f-]pyrazino[1,2-a]azepin-2-yl)pentanoate, in a yield of 97%.

Infrared Absorption Spectrum (CHCl$_3$) $v_{max}$ cm$^{-1}$: 1450, 1495, 1600, 1730, 2820, 2950.

EXAMPLE 21

Ethyl 6-(1,2,3,4,10,14b-hexanhydrodibenzo[c,f-]pyrazino-[ 1,2-a]azepin-2-yl)hexanoate, in a yield of 99%.

Infrared Absorption Spectrum (CHCl$_3$) $v_{max}$ cm$^{-1}$: 1450, 1495, 1600, 1730, 2800, 2950.

Following a procedure similar to that described in Example 1 or Example 17, but using the corresponding acids, the following salts were obtained.

Ethyl 4-(1,2,3,4,10,14b-hexahydrodibenzo[c,f-]pyrazino[1,2-a]azepin-2-yl)butanoate fumarate, melting at 139°–140° C.

Ethyl 5-(1,2,3,4,10,14b-hexahydrodibenzo[c,f-]pyrazino[1,2-a]azepin-2-yl)pentanoate hydrochloride, melting at 167°–169° C.

Ethyl 6-(1,2,3,4,10,14b-hexahydrodibenzo[c,f-]pyrazino[1,2-a]azepin-2-yl)hexanoate hydrochloride, melting at 150°–152° C.

EXAMPLES 22 to 24

Following a procedure similar to that described in Example 2, but using the corresponding ester from Example 19, 20 or 21, respectively, the following carboxylic acids were synthesized.

EXAMPLE 22

4-(1,2,3,4,10,14b-Hexahydrodibenzo[c,f]pyrazino[1,2-a]azepin-2-yl)butanoic acid, in a yield of 63%.

EXAMPLE 23

5-(1,2,3,4,10,14b-Hexahydrodibenzo[c,f]pyrazino[1,2-a]azepin-2-yl)pentanoic acid, melting at 240°–243° C. (with decomposition), in a yield of 54%.

Infrared Absorption Spectrum (KBr) $v_{max}$ cm$^{-1}$: 1445, 1492, 1744, 2596, 2683, 2939, 3020.

EXAMPLE 24

6-(1,2,3,4,10,14b-Hexahydrodibenzo[c,f]pyrazino[1,2-a]azepin-2-yl)hexanoic acid, in a quantitative yield.

Infrared Absorption Spectrum (CHCl$_3$) $v_{max}$ cm$^{-1}$: 1450, 1500, 1600, 1720, 2450, 2970.

Following a procedure similar to that described in Example 17, the following salts were obtained.

4-(1,2,3,4,10,14b-Hexahydrodibenzo[c,f]pyrazino[1,2-a]azepin-2-yl)butanoic acid hydrochloride, melting at 188°–189° C.

Infrared Absorption Spectrum (KBr) $v_{max}$ cm$^{-1}$: 1447, 1492, 1595, 1729, 2362, 2949, 2981.

6-(1,2,3,4,10,14b-Hexahydrodibenzo[c,f]pyrazino[1,2-a]azepin-2-yl) hexanoic acid hydrochloride, melting at 193°–195° C. (with decomposition).

EXAMPLE 25

Ethyl 6-(1,2,3,4,10,14b-hexahydrodibenzo[c,f]pyrazino[1,2-a]azepin-2-yl)hexyloxyacetate 0.060 g of a 55% w/w dispersion of sodium hydride in mineral oil was added to a solution of 0.40 g of 6-(1,2,3,4,10,14b-hexahydrodibenzo[c,f]pyrazino[1,2-a]azepin-2-yl)hexanol (prepared as described in Example 18) dissolved in 10 ml of toluene, under an atmosphere of nitrogen. The mixture was stirred at 40° C. for 2 hours and then cooled with ice, after which 0.229 g of methyl bromoacetate were added, and the mixture was stirred at 40° C. for a further 4 hours. At the end of this time, the reaction mixture was filtered, and the solvent was removed from the filtrate by evaporation under reduced pressure. The residue was subjected to column chromatography through silica gel, using a 1:1 by volume mixture of ethyl acetate and hexane as the eluent, to afford 90 mg (yield 18%) of the title compound as an oil.

Nuclear Magnetic Resonance Spectrum (CDCl$_3$) δ ppm:
1.26 (3H, triplet); 1.53–1.72 (8H, multiplet); 2.31–2.45 (4H, multiplet); 2.94 (2H, doublet of doublets); 3.26–3.37 (3H, multiplet); 3.56–3.63 (2H, multiplet); 4.06–4.25 (4H, multiplet); 4.82 (1H, doublet); 6.86 (1H, triplet); 7.01–7.20 (8H, multiplet).

Infrared Absorption Spectrum (CHCl$_3$) $\nu_{max}$ cm$^{-1}$: 1445, 1490, 1595, 1745, 2800, 2925.

EXAMPLE 26

2-(1,2,3,4,10,14b-Hexahydrodibenzo[c,f]pyrazino[1,2-a]azepin-2-yl)ethoxyacetamide 0.358 g of 2-(1,2,3,4,10,14b-hexahydrodibenzo[c,f]pyrazino[1,2-a]azepin-2-yl)ethoxyacetic acid (prepared as described in Example 2) and 0.11 g of triethylamine were added to 15 ml of tetrahydrofuran. A solution of 0.11 g of ethyl chloroformate in 2 ml of tetrahydrofuran was then added dropwise to the mixture, whilst ice-cooling, and the mixture was stirred at room temperature for 30 minutes. At the end of this time, 2 ml of 28% aqueous ammonia was added to the mixture, whilst ice-cooling, and the mixture was then stirred at room temperature for 30 minutes. The reaction mixture was then mixed with water and extracted with methylene chloride. The extract was concentrated by evaporation under reduced pressure, and the residue was subjected to column chromatography through silica gel, using 5% by volume methanol in methylene chloride as the eluent, to afford 0.29 g (yield 82%) of the title compound, melting at 66°–68° C.

Infrared Absorption Spectrum (KBr) $\nu_{max}$ cm$^{-1}$: 1450, 1492, 1684, 2814, 2942, 3100, 3276.

EXAMPLES 27 to 29

Following a procedure similar to that described in Example 26, but using the corresponding amine, the following compounds were synthesized.

EXAMPLE 27

α-[2-(1,2,3,4,10,14b-Hexahydrodibenzo[c,f]pyrazino[1,2-a]azepin-2-yl)ethoxy]-N,N-dimethylacetamide, in a yield of 79%

Infrared Absorption Spectrum (CHCl$_3$) $\nu_{max}$ cm$^{-1}$: 1450, 1495, 1600, 1645, 2820, 2950, 3005.

EXAMPLE 28

α-[2-(1,2,3,4,10,14b-Hexahydrodibenzo[c,f]pyrazino[1,2-a]azepin-2-yl)ethoxy]-N-phenylacetamide, melting at 132–133° C., in a yield of 74%.

Infrared Absorption Spectrum (CHCl$_3$), $\nu_{max}$ cm$^{-1}$: 1445, 1490, 1530, 1600, 1680, 2820, 2950, 3400.

EXAMPLE 29

N-Benzyl-α-[2-(1,2,3,4,10,14b-Hexahydrodibenzo[c,f]pyrazino[1,2-a]azepin-2-yl)ethoxy]acetamide, melting at 92°–93° C., in a yield of 74%.

Infrared Absorption Spectrum (KBr), $\nu_{max}$ cm$^{-1}$: 1453, 1491, 1516, 1676, 2813, 2938.

Following a procedure similar to that described in Example 17, the hydrochloride of the compound of Example 27 was obtained, melting at 80°–82° C. (with decomposition).

EXAMPLE 30

N-Cyclohexyl-α-[2-(1,2,3,4,10,14b-hexahydrodibenzo[c,f]pyrazino[1,2-a]azepin-2-yl)ethoxy]acetamide 0.358 g of 2-(1,2,3,4,10,14b-hexahydrodibenzo[c,f]pyrazino[1,2-a]azepin-2-yl)ethoxyacetic acid (prepared as described in Example 2), 0.1 g of cyclohexylamine and 0.11 g of triethylamine were added to 10 ml of tetrahydrofuran, and 0.17 g of diethyl cyanophosphonate was added dropwise to the mixture, whilst ice-cooling. The mixture was then stirred at room temperature for 5 hours, after which it was mixed with water and then extracted with methylene chloride. The extract was concentrated by evaporation under reduced pressure, and the residue was subjected to column chromatography through silica gel, using 10 % by volume ethanol in ethyl acetate as the eluent, to afford 0.4 g (yield 91%) of the title compound.

Following a procedure similar to that described in Example 17, the hydrochloride of the title compound was obtained, melting at 110°–112° C. (with decomposition).

Infrared Absorption Spectrum (CHCl$_3$) $\nu_{max}$ cm$^{-1}$: 1449, 1493, 1537, 1663, 2853, 2931, 3258.

EXAMPLE 31 to 39

Following a procedure similar to that described in Example 30, but using the corresponding amine, the following compounds were synthesized.

EXAMPLE 31

α-[2-(1,2,3,4,10,14b-Hexahydrodibenzo[c,f]pyrazino[1,2-a]azepin-2-yl)ethoxy]-N,N-dipropylacetamide, in a yield of 61%.

Infrared Absorption Spectrum (CHCl$_3$) $\nu_{max}$ cm$^{-1}$: 1455, 1500, 1645, 2845, 2900, 2980, 3020.

EXAMPLE 32

N-t-Butyl-α-[2-(1,2,3,4,10,14b-hexahydrodibenzo[c,f]pyrazino[1,2-a]azepin-2-yl)ethoxy]acetamide, melting at 115°–116° C., in a yield of 53%.

Infrared Absorption Spectrum (KBr), $\nu_{max}$ cm$^{-1}$: 1449, 1491, 1523, 1673, 2804, 2951, 2969, 3401.

EXAMPLE 33

N-Cyclopropyl-α-[2-(1,2,3,4,10,14b-hexahydrodibenzo[c,f]pyrazino[1,2-a]azepin-2-yl)ethoxy]acetamide, in a yield of 83%.

Infrared Absorption Spectrum (CHCl$_3$), $\nu_{max}$ cm$^{-1}$:
1450, 1495, 1600, 1670, 1720, 2830, 3000, 3440.

EXAMPLE 34

N-Cyclobutyl-α-[2-(1,2,3,4,10,14b-hexahydrodibenzo[c,f]pyrazino[1,2-a]azepin-2-yl)ethoxy]acetamide, melting at 113°–115° C., in a yield of 88%.

Infrared Absorption Spectrum (KBr), $\nu_{max}$ cm$^{-1}$:
1445, 1491, 1508, 1651, 2806, 2947, 3246.

EXAMPLE 35

N-Cyclopentyl-α-[2-(1,2,3,4,10,14b-hexahydrodibenzo[c,f]pyrazino[1,2-a]azepin-2-yl)ethoxy]acetamide, in a yield of 88%.

Infrared Absorption Spectrum (CHCl$_3$), $\nu_{max}$ cm$^{-1}$:
1450, 1495, 1530, 1600, 1665, 2825, 2960, 3220.

EXAMPLE 36

N-Cycloheptyl-α-[2-(1,2,3,4,10,14b-hexahydrodibenzo[c,f]pyrazino[1,2-a]azepin-2-yl) ethoxy]acetamide, melting at 97°–99° C., in a quantitative yield.

Infrared Absorption Spectrum (CHCl$_3$), $\nu_{max}$ cm$^{-1}$:
1450, 1495, 1530, 1600, 1665, 2860, 2945, 3330.

EXAMPLE 37

4-{2-(1,2,3,4,10,14b-Hexahydrodibenzo[c,f]pyrazino[1,2-a]azepin-2-yl)ethoxyacetyl}morpholine, in a yield of 84%.

Infrared Absorption Spectrum (CHCl$_3$), $\nu_{max}$ cm$^{-1}$:
1450, 1495, 1600, 1640, 1730, 2820, 2860.

EXAMPLE 38

N-(2-Dimethylaminoethyl)-α- [2-(1,2,3,4,10,14b-hexahydrodibenzo[c,f]pyrazino [1,2-a]azepin-2-yl) ethoxy]acetamide, in a yield of 84%.

Infrared Absorption Spectrum (CHCl$_3$), $\nu_{max}$ cm$^{-1}$:
1450, 1495, 1530, 1600, 1670, 2840, 2960, 3430.

EXAMPLE 39

N-[2-(4-p,p'-difluorobenzhydrylpiperazin-1-yl)ethyl]-α-[2-( 1,2,3,4,10,14b-hexahydrodibenzo[c,f]pyrazino[1,2-a]azepin-2-yl)ethoxy]acetamide, in a yield of 93%.

Infrared Absorption Spectrum (CHCl$_3$), $\nu_{max}$ cm$^{-1}$:
1450, 1495, 1505, 1605, 1665, 2820, 2950, 3410.

Following a procedure similar to that described in Example 17, the following salts were obtained.

Hydrochloride of the compound of Example 31, melting at 82°–84° C.

Hydrochloride of the compound of Example 35, melting at 124°–127° C. (with decomposition).

Hydrochloride of the compound of Example 37, melting at 110°–112° C. (with decomposition).

Dihydrochloride of the compound of Example 38, melting at 133°–135° C. (with decomposition).

Trihydrochloride of the compound of Example 39, melting at 176°–178° C. (with decomposition).

EXAMPLE 40

2-(2,3-Dihydroxypropyl)-1,2,3,4,10,14b-hexahydrodibenzo[c,f]pyrazino[1,2-a]azepine A mixture of 0.41 g of glycidol and 0.9 ml of water was added, whilst ice-cooling, to a solution of 1 g of 1,2,3,4,10,14b-hexahydrodibenzo[c,f]pyrazino[1,2-a]azepine dissolved in 2 ml of ethanol, and the mixture was stirred at room temperature for 5 hours; it was then concentrated by evaporation under reduced pressure. The residue was subjected to column chromatography through silica gel, using a 10:1 by volume mixture of ethyl acetate and ethanol as the eluent, to afford 0.72 g (yield 56%) of the title compound as a colorless foam.

Infrared Absorption Spectrum (CHCl$_3$), $\nu_{max}$ cm$^{-1}$:
1455, 1500, 1605, 1740, 2850, 2980, 3040.

Following a procedure similar to that described in Example 17, the hydrochloride of this compound, melting at 205°–207° C. (with decomposition), was obtained.

EXAMPLE 41

2-(3-Chloro-2-hydroxypropyl)-1,2,3,4,10,14b-hexahydrodibenzo[c,f]pyrazino[1,2-a]azepine 0.832 g of epichlorohydrin was added to a mixture of 4.5 ml of ethanol and 1.5 g of 1,2,3,4,10,14b-hexahydrodibenzo[c,f]pyrazino[1,2-a]azepine, whilst ice-cooling, and the mixture was stirred at room temperature for 5 hours. At the end of this time, it was concentrated by evaporation under reduced pressure. The residue was subjected to column chromatography through silica gel, using a 1:1 by volume mixture of hexane and ethyl acetate as the eluent, to afford 1.56 g (yield 76%) of the title compound as a colorless foam.

Infrared Absorption Spectrum (CHCl$_3$) $\nu_{max}$ cm$^{-1}$:
1498, 1600, 3200.

Nuclear Magnetic Resonance Spectrum (CDCl$_3$), δ ppm:
2.30–3.20 (5H, multiplet);
3.20–3.50 (3H, multiplet);
3.50–3.70 (2H, doublet);
3.78–4.25 (2H, multiplet);
4.82 (1H, doublet ); 6.70–7.40 (9H, multiplet ).

EXAMPLE 42

2-(2-Hydroxy-3-morpholinopropyl)-1,2,3,4,10,14b-hexahydrodibenzo[c,f]pyrazino[1,2-a]azepine 0. 5 g of 2-(3-chloro-2-hydroxypropyl)-1,2,3,4,10,14b-hexahydrodibenzo [c,f]pyrazino [1,2-a]azepine (prepared as described in Example 41), 2.7 g of sodium carbonate, 0.014 g of sodium iodide and 0.254 g of morpholine were added to 10 ml of 4-methyl-2-pentanone, and the mixture was heated under reflux for 2 hours. At the end of this time, the reaction mixture was filtered, and then the filtrate was concentrated by evaporation under reduced pressure. The residue was subjected to column chromatography through silica gel, using ethyl acetate as the eluent, to afford 0.50 g (yield 87%) of the title compound as a colorless foam.

Infrared Absorption Spectrum (Nujol), $\nu_{max}$ cm$^{-1}$:
1454, 1491, 2853, 2951, 3400.

Following a procedure similar to that described in Example 17, the hydrochloride of the title compound was obtained, melting at 223°–226° C. (with decomposition).

EXAMPLES 43 to 46

Following a procedure similar to that described in Example 42, but using the corresponding amine, the following compounds were synthesized.

EXAMPLE 43

2-[3-(4-p-Chlorobenzhydrylpiperazin-1-yl)-2-hydroxypropyl]-1,2,3,4,10,14b-hexahydrodibenzo[c,f]pyrazino[1,2-a]azepine, in a yield of 99%.

Infrared Absorption Spectrum (CHCl$_3$), $\nu_{max}$ cm$^{-1}$:
1455, 1495, 1600, 2830, 2950, 3400.

EXAMPLE 44

2-(2-Hydroxy-3-cyclohexylaminopropyl)-1,2,3,4,10,14b-hexahydrodibenzo[c,f]pyrazino[1,2-a]azepine, in a yield of 87%.

Infrared Absorption Spectrum (CHCl$_3$), $\nu_{max}$ cm$^{-1}$: 1450, 1495, 1600, 2850, 2940, 3400.

EXAMPLE 45

2-(3-t-Butylamino-2-hydroxypropyl)-1,2,3,4,10,14b-hexahydrodibenzo[c,f]pyrazino[1,2-a]azepine, in a yield of 64%.

Infrared Absorption Spectrum (CHCl$_3$), $\nu_{max}$ cm$^{-1}$: 1450, 1495, 1600, 2830, 2960, 3350.

EXAMPLE 46

2-(2-Hydroxy-3-phenylaminopropyl)-1,2,3,4,10,14b-hexahydrodibenzo[c,f]pyrazino[1,2-a]azepine, in a yield of 69%.

Following a procedure similar to that described in Example 1 or Example 17, but using the corresponding acid, the following salts were prepared.

Hydrochloride of the compound of Example 43, melting at 213°–215° C. (with decomposition).

Maleate of the compound of Example 44, melting at 195°–197° C. (with decomposition).

Maleate of the compound of Example 45, melting at 171°–173° C.

Hydrochloride of the compound of Example 46, melting at 223°–226° C.

Infrared Absorption Spectrum (KBr), $\nu_{max}$ cm$^{-1}$: 1445, 1493, 1603, 2608, 2712, 2969, 3319.

EXAMPLE 47

Ethyl 2-(1,2,3,4,10,14b-hexahydrodibenzo[c,f]pyrazino[[1,2-a]azepin-2yl)ethoxyacetate 0.11 g of chloroethyl carbonate was added to a solution of 0.5 g of 2-(1,2,3,4,10,14b-hexahydrodibenzo[c,f-]pyrazino [1,2-azepin-2-yl)ethoxyacetic acid (prepared as described in Example 2) in 10 ml of chloroform containing 2% by volume ethanol, whilst ice-cooling, and the mixture was stirred at room temperature for 1 hour. At the end of this time, it was washed with water, and the solvent was removed by distillation under reduced pressure. The resulting residue was subjected to column chromatography through silica gel eluted with ethyl acetate, to give 0.25 g of the title compound as a colorless oil. The infrared absorption spectrum of this compound is identical with that of the compound prepared as described in Example 1.

This compound was converted by similar means to those described in Example 17 to its hydrochloride, melting at 170°–171° C.

EXAMPLES 48 & 49

Following a procedure similar to that described in Example 8, but using the corresponding chloroethoxy compound, the following compounds were synthesized.

EXAMPLE 48

2-(2-Hydroxyethoxy)ethyl-1,2,3,4,10,14b-hexahydrobenzo[c]pyrazino[1,2-a]pyrido[5,6-c]azepine, in a yield of 84%.

Infrared Absorption Spectrum (CHCl$_3$), $\nu_{max}$ cm$^{-1}$: 1440, 1590, 1730, 2820, 2870, 2950, 3300.

The dihydrochloride, melting at 132°–135° C. (with decomposition), may be prepared by similar means to those described in Example 17.

EXAMPLE 49

2-{2[2-(2-Hydroxyethoxy)ethoxy]ethyl}-1,2,3,4,10,14b-hexahydrobenzo[c]pyrazino [1,2-a]pyrido[5,6-c]azepine dihydrochloride, melting at 102°–104° C. (with decomposition), in a quantitative yield.

Infrared Absorption Spectrum (CHCl$_3$), $\nu_{max}$ cm$^{-1}$: 1440, 1590, 1705, 2870, 2950, 3450.

EXAMPLE 50

3-(1,2,3,4,10,14b-Hexahydrodibenzo[c,f]pyrazino[1,-2,a]azepin-2-yl)propyl carbamate 0.2 ml of trichloroacetyl isocyanate were added to a solution of 400 mg of 3-(1,2,3,4,10,14b-hexahydrodibenzo[c,f]pyrazino[1,2-a]azepin-2-yl)propanol (prepared as described in Example 16) in 20 ml of methylene chloride, whilst ice-cooling, and the mixture was stirred at room temperature for 2 hours. At the end of this time, the solvent was removed by distillation under reduced pressure. The resulting residue was dissolved in 22 ml of methanol, 9.0 g of silica gel were added to the solution and the mixture was stirred at room temperature for 15 hours. At the end of this time, the mixture was filtered using a Celite (trade mark) filter aid, and the filtrate was concentrated by evaporation under reduced pressure. The residue was subjected to column chromatography through silica gel eluted with ethyl acetate, to give, after recrystallization from ethyl acetate, 260 mg (yield 59%) of the title compound as crystals, melting at 160°–161° C.

Infrared Absorption Spectrum (KBr), $\nu_{max}$ cm$^{-1}$: 1638, 1722, 3119, 3313.

EXAMPLE 51

2-(1,2,3,4,10,14b-Hexahydrodibenzo[c,f]pyrazino[1,2-a]azepin-2-yl)ethyl carbamate Following a procedure similar to that described in Example 50, but using 2-(1,2,3,4,10,14b-hexahydrodibenzo[c,f]pyrazino[1,2-a]azepin-2-yl)ethanol [prepared as described in step (a) or (c) of Example 3], the title compound, melting at 182°–184° C. (with decomposition), was prepared in a 62% yield.

Infrared Absorption Spectrum (KBr), $\nu_{max}$ cm$^{-1}$: 1611, 1695, 1723, 3278, 3396.

EXAMPLES 52 TO 57

Following a procedure similar to that described in Example 1, the following compounds were synthesized from the corresponding chlorester compounds.

EXAMPLE 52

Methyl 3-(1,2,3,4,10,14b-hexahydrodibenzo[c,f-]pyrazino[1,2-a]azepin-2-yl)propoxyacetate, as an oil in a yield of 46%.

Infrared Absorption Spectrum (CHCl$_3$), $\nu_{max}$ cm$^{-1}$: 1495, 1600, 1755, 2830, 2970.

EXAMPLE 53

Ethyl 4-(1,2,3,4,10,14b-hexahydrodibenzo[c,f-]pyrazino[1,2-a]azepin-2-yl)butoxyacetate, as an oil in a yield of 50%.

Infrared Absorption Spectrum (CHCl$_3$), $\nu_{max}$ cm$^{-1}$: 1500, 1600, 1750, 2840, 2960.

EXAMPLE 54

Methyl 6-(1,2,3,4,10,14b-hexahydrodibenzo[c,f]pyrazino[1,2-a]azepin-2-yl)hexyloxyacetate, as an oil in a yield of 72%.

Infrared Absorption Spectrum (CHCl$_3$), $\nu_{max}$ cm$^{-1}$: 1495, 1600, 1750, 2830, 2950.

EXAMPLE 55

Ethyl 6-(1,2,3,4,10,14b-hexahydrodibenzo[c,f]pyrazino[1,2-a]azepin-2yl)hexyloxyacetate, as an oil in a yield of 75%.

The infrared absorption spectrum of this compound is identical with that of the compound prepared as described in Example 25.

EXAMPLE 56

Ethyl 2-[2-(1,2,3,4,10,14b-hexahydrodibenzo[c,f]1,2-a]azepin-2-yl)ethoxy]propionate, as an oil in a yield of 77%.

Infrared Absorption Spectrum (CHCl$_3$), $\nu_{max}$ cm$^{-1}$: 1495, 1600, 1740, 2840, 2960.

EXAMPLE 57

Ethyl 2-[2-(1,2,3,4,10,14b-hexahydrodibenzo[c,f]pyrazino[1,2-a]azepin-2-yl)ethoxy]butanoate, as an oil in a yield of 68%.

Infrared Absorption Spectrum (CHCl$_3$), $\nu_{max}$ cm$^{-1}$: 1495, 1750, 2830, 2950.

Following a procedure similar to that described in Example 1, the following salts were obtained.

Methyl 3-(1,2,3,4,10,14b-Hexahydrodibenzo[c,f]pyrazino[1,2-a]azepin-2-yl)propoxyacetate oxalate, melting at 102°–104° C.

Ethyl 4-(1,2,3,4,10,14b-hexahydrodibenzo[c,f]pyrazino[1,2-a]azepin-2-yl)butoxyacetate oxalate, melting at 157°–160° C.

Methyl 6-( 1,2,3,4,10,14b-hexahydrodibenzo[c,f]pyrazino[1,2-a]azepin-2-yl)hexyloxyacetate oxalate, melting at 140°–141° C.

Ethyl 6-(1,2,3,4,10,14b-hexahydrodibenzo[c,f]pyrazino[1,2-a]azepin-2-yl)hexyloxyactate oxalate, melting at 115°–120° C.

Ethyl 2-[2-(1,2,3,4,10,14b-hexahydrodibenzo[c,f]pyrazino[1,2-a]azepin-2-yl)ethoxy]propionate oxalate, melting at 160°–162° C. (with decomposition).

Ethyl 2-[2-(1,2,3,4,10,14b-hexahydrodibenzo[c,f]pyrazino[1,2-a]azepin-2-yl)ethoxy]butanoate oxalate, melting at 160°–162° C. (with decomposition).

EXAMPLE 58

Ethyl (S)-2-(1,2,3,4,10,14b-hexahydrodibenzo[c,f]pyrazino[1,2-a]azepin-2-yl)ethoxyacetate 32.48 g of (S)-1,2,3,4,10,14b-hexahydrodibenzo[c,f]pyrazino[1,2-a]azepine (prepared as described in Preparation 3), 22.7 g of ethyl 2-chloroethoxyacetate, 48.9 g of sodium carbonate and 0.79 g of sodium iodide were added to 340 ml of 4-methyl-2-pentanone, and the mixture was heated under reflux for 16 hours. At the end of this time, it was cooled to room temperature and was filtered using a Celite filter aid, and the filtrate was concentrated by evaporation under reduced pressure. The resulting residue was subjected to column chromatography through silica gel eluted with a 1:1 by volume mixture of ethyl acetate and hexane, to give 44.85 g (yield 91%) of the title compound as a pale yellow oil.

Infrared Absorption Spectrum (CHCl$_3$), $\nu_{max}$ cm$^{-1}$: 1495, 1600, 1750, 2820, 2950[$\alpha$]$_D^{25}$+275° (c=1.0, methanol).

EXAMPLE 59

(S)-2-(1,2,3,4,10,14b-hexahydrodibenzo[c,f]pyrazino[1,2-a]azepin-2-yl)ethoxyacetic acid 65 ml of a 10% w/v aqueous solution of sodium hydroxide and 200 ml of water were added to a solution of 44.85 g of ethyl (S)-2-(1,2,3,4,10,14b-hexahydrodibenzo[c,f]pyrazino[1,2-a]azepin-2-yl)ethoxyacetate (prepared as described in Example 58) in 450 ml of ethanol, and the mixture was stirred at room temperature for 2 hours. At the end of this time, it was adjusted to a pH value of 4 by the addition of concentrated hydrochloric acid and concentrated by evaporation under reduced pressure. The crystals which precipitated were collected by filtration and recrystallized from water to give 39.20 g (yield 90%) of the title compound as the monohydrate, melting at 105°–108° C.

Infrared Absorption Spectrum (KBr), $\nu_{max}$ cm$^{-1}$: 1446, 1492, 1598, 1633, 3404, 3449. [$\alpha$]$_D^{25}$+325° (c=1.0, dimethylformamide).

10% v/v solution of hydrochloric acid in ethanol was added to a solution of the title compound in ethanol, and the mixture was stirred at room temperature was removed by evaporation under reduced pressure, and the residue was recrystallized from water to give the hydrochloride of the title compound, melting at 210°–212° C.

[$\alpha$]$_D^{25}$+230° (c=1.0, dimethylformamide).

A 10% v/v solution of hydrochloric acid in ethanol solution of the title compound in ethanol, and the mixture was stirred at room temperature for 30 minutes. At the end of this time, the solvent was removed by evaporation under reduced pressure, and ethyl acetate was added to the residue to give the hemifumarate of the title compound, melting at 161°–163° C.

[$\alpha$]$_D^{25}$+265° (c=1.0, dimethylformamide).

Following a procedure similar to that described in Example 58, but using the corresponding bromoester compound, the following compounds were synthesized.

EXAMPLE 60

Ethyl (S)-4-(1,2,3,4,10,14b-hexahydrodibenzo[c,f]pyrazino[1,2-a]azepin-2-yl)butanoate, as an oil in a yield of 97%.

Infrared Absorption Spectrum (CHCl$_3$), $\nu_{max}$ cm$^{-1}$: 1495, 1680, 1730, 2830, 2960. [$\alpha$]$_D^{25}$+301° (c=1.0, methanol). Example 1, the fumarate of the title compound was obtained, melting at 139°–141° C.

[$\alpha$]$_D^{25}$+215° (c=1.0, methanol).

EXAMPLE 61

Ethyl (S)-6-(1,2,3,4,10,14b-hexahydrodibenzo[c,f]pyrazino[1,2-a]azepin-2-yl)hexanoate, as an oil in yield of 98%.

Infrared Absorption Spectrum (CHCl$_3$), $\nu_{max}$ cm$^{-1}$: 1495, 1600, 1730, 2840, 2955. [$\alpha$]$_D^{25}$+284° (c=1.0, methanol).

Following a procedure similar to that described in Example 58, but using (R)-1,2,3,4,10,14b-hexahydrodibenzo[c,f]pyrazino[1,2-a]azepine (prepared as described in Preparation 4) and the corresponding chloride, ethyl (R)-2-(1,2,3,4,10,14b-hexahydrodibenzo[c,f]pyrazino[1,2-a]azepin-2-yl)ethoxyacetate was obtained as an oil in a yield of 91%.

Infrared Absorption Spectrum (CHCl3), $\nu_{max}$ cm$^{-1}$: 1495, 1600, 1750, 2820, 2950. $[\alpha]_D^{25} -303°$ (c=1.0, methanol).

Following a procedure similar to that described in Example 1, the fumarate of the title compound was obtained, melting at 128°-130° C. $[\alpha]_D^{25} -241°$ (c=1.0, dimethylformamide).

EXAMPLES 63 & 64

Following a procedure similar to that described in Example 58, but using (R)-1,2,3,4,10,14b-hexahydrodibenzo[c,f]pyrazino[1,2-a]azepine (prepared as described in Preparation 4) and the corresponding synthesized.

EXAMPLE 63

Ethyl (R)-4-(1,2,3,4,10,14b-hexahydrodibenzo[c,f-]pyrazino[1,2-a]azepin-2-yl)butanoate, as an oil in a yield of 99%.

Infrared Absorption Spectrum (CHCl3), $\nu_{max}$ cm$^{-1}$: 1495, 1600, 1730, 2830, 2960. $[\alpha]_D^{25} -296°$ (c=1.0, methanol).

Following a procedure similar to that described in Example 1, the fumarate of the title compound was obtained, melting at 139°-141° C. $[\alpha]_D^{25} -216°$ (c=1.0, methanol).

EXAMPLE 64

Ethyl (R)-6-(1,2,3,4,10,14b-hexahydrodibenzo[c,f-]pyrazino[1,2-a]azepin-2-yl)hexanoate, as an oil in a yield of 98%.

Infrared Absorption Spectrum (CHCl3), $\nu_{max}$ cm$^{-1}$: 1495, 1600, 1730, 2840, 2955.

$[\alpha]_D^{25} -296°$ (c=1.0, methanol).

EXAMPLE 65

Following a procedure similar to that described in Example 59, (R)-2-( 1,2,3,4,10,14b-hexahydrodibenzo[c,f]pyrazino[melting at 104°-107° C. was prepared in a yield of 88% from ethyl (R)-2-(1,2,3,4,10,14b-hexahydrodibenzo[c,f]pyrazino[1,2-a]azepin-2-yl)ethoxyacetate (prepared as described in Example 62).

$[\alpha]_D^{25} -322°$ (c=1.0, dimethylformamide).

Following a procedure similar to that described in Example 1 or Example 17, the hydrochloride and fumarate of the title compound were obtained, melting at 209°-211° C. and 154°-156° C., respectively.

$[\alpha]_D^{25} -225°$ (c=1.0, dimethylformamide) for the hydrochloride $[\alpha]_D^{25} -207°$ (c=1.0, dimethylformamide) for the fumarate.

EXAMPLES 66 & 67

Following a procedure similar to that described in Example 59 and then a procedure similar to that described in Example 17, the following hydrochlorides were synthesized from the corresponding esters prepared as described in Examples 61 and 64.

EXAMPLE 66

(S)-6-( 1,2,3,4,10,14b-Hexahydrodibenzo[c,f-]pyrazino[1,2-a]azepin-2-yl)hexanoic acid hydrochloride in a yield of 85%, melting at 255°-259° C. (with decomposition). $[\alpha]_D^{25} +256°$ (c=1.0, dimethylformamide).

EXAMPLE 67

(R)-6-(1,2,3,4,10,14b-Hexahydrodibenzo[c,f-]pyrazino[1,2-a]azepin-2-yl)hexanoic acid hydrochloride in a yield of 92%, melting at 243°-250° C. (with decomposition).

$[\alpha]_D^{25} -254°$ (c=1.0, dimethylformamide).

PREPARATION 1

Ethyl 2-chloroethoxyacetate

A suspension of 25.0 g of sodium hydride (as a 60% w/w suspension in mineral oil ) in 100 ml of dimethylformamide was added dropwise to a solution of 50 g of 2-chloroethanol and 104 g of ethyl bromoacetate in 350 ml of dimethylformamide at between −45° C. and −40° C., and the mixture was stirred at the same temperature for 1 hour, at between −30° C. and −25° C. for 2 hours, at −5° C.-5° C. for 1 hour and then at room temperature for 2 hours. At the end of this time, it was concentrated by evaporation under reduced pressure, and 1000 ml of toluene were added to the residue. The solution was then washed with water, and the solvent was removed by evaporation under reduced pressure. Distillation gave 77.6 g (yield 75%) of the title compound, boiling at 57°-58° C./2.5 mmHg (333 Pa).

Nuclear Magnetic Resonance Spectrum (CDCl$^3$), δ ppm:

1.30 (3H, triplet, J=7.0 Hz);
3.70 (2H, triplet, J=4.5 Hz);
3.84 (2H, triplet, J=4.5 Hz);
4.15 (2H, singlet);
4.22 (2H, quartet, J=7.0 Hz);

PREPARATION 2

Ethyl 2-chloroethoxyacetate

A solution of 30 g of 2-(2-chloroethoxy)ethanol in 300 ml of acetone was added dropwise to a mixture of 240 ml of Jones' reagent (prepared by dissolving 133.5 g of chromium trioxide by adding 115 ml of concentrated sulfuric acid and water, followed by adding further water to a total volume of 500 ml) and 1050 ml of acetone at −5°-0° C., and the mixture was stirred at the same temperature for 30 minutes. At the end of this time, 150 ml of isopropanol were added to the mixture, which was then stirred at room temperature for 1 hour. At the end of this time, it was filtered, and the filtrate was concentrated by evaporation under reduced pressure and adjusted to a pH value of 3 by adding aqueous sodium bicarbonate. The mixture was extracted with ethyl acetate, and the solvent was evaporated from the extract, to give 24.9 g (yield 75%) of 2-chloroethoxyacetic acid as a pale green oil. Gaseous hydrogen chloride was passed through a solution of 24.9 g of this acid in 250 ml of ethanol, and the mixture was heated under reflux for 3 hours. At the end of this time, it was concentrated by evaporation under reduced pressure. Distillation gave 29.2 g (yield 95%) of the title compound as a colorless oil, boiling at 96° C./14 mmHg (1866 Pa).

PREPARATION 3

(S)-1,2,3,4,10,14b-Hexahydrodibenzo[c,f]pyrazino[1,2-a]azepine

3(a) Ethyl (S)-(1,2,3,4,10,14b-hexahydrodibenzo[c,f-]pyrazino [1,2-a]azepin-2-yl)carboxylate A solution of 5.52 g of (S)-1,2,3,4,10,14b-hexahydro-2-methyldibenzo[c,f]pyrazino[1,2-a]azepine (prepared as described in preparation 6) in 30 ml of toluene was added dropwise to a solution of 6.8 g of ethyl chloroformate in 50 ml of toluene at 80° C. over a period of 10 minutes, and the mixture was heated under reflux for 3hours. At the end of this time, the crystals which precipitated were removed by filtration, and solvent was removed from the filtrate by evaporation under reduced pressure, to give 6.57 g (yield 98%) of the title compound as a pale yellow oil.

Infrared Absorption Spectrum (CHCl3), $\nu_{max}$ cm$^{-1}$: 1240, 1435, 1495, 1600, 1690, 3010. $[\alpha]_D^{25}+286°$ (c=1.0, methanol).

3(b) (S)-(1,2,3,4,10,14b-Hexahydrodibenzo[c,f]pyrazino[1,2-a]azepine

A solution of 10.2 g of potassium hydroxide in 34 ml of water was added to a solution of 6.54 g of ethyl (S)-(1,2,3,4,10,14b-hexahydrodibenzo[c,f]pyrazino[1,2-a]azepin-2-yl)carboxylate [prepared as described in step (a) above] in 85 ml of ethylene glycol, and the mixture was heated under reflux for 16 hours. At the end of this time, the mixture was poured into ice-water and extracted with ethyl acetate. Evaporation of the solvent from the extract gave 4.71 g (yield 93%) of the title compound as colorless crystals, melting at 122°-124° C.

Infrared Absorption Spectrum (KBr), $\nu_{max}$ cm$^{-1}$: 1489, 2791, 2899, 3191. $[\alpha]_D^{25}+488°$ (c=1.0, methanol).

(R)-1,2,3,4,10,14b-Hexahydrodibenzo[c,f]pyrazino[1,2-a]azepine

4(a) Ethyl (R)-(1,2,3,4,10,14b-hexahydrodibenzo[c,f]pyrazino[1,2-a]azepin-2-yl)carboxylate Following a procedure similar to that described in Preparation 3(a), but using (R)-1,2,3,4,10,14b-hexahydro-2-methyldibenzo[c,f]pyrazino[1,2-a]azepine, the title compound was obtained in a 98% yield.

Infrared Absorption Spectrum (CHCl3), $\nu_{max}$ cm$^{-1}$: 1240, 1435, 1495, 1600, 1690, 3010. $[\alpha]_D^{25}-255°$ (c=1.0, methanol).

4(b) (R)-1,2,3,4,10,14b-Hexahydrodibenzo[c,f]pyrazino[1,2-a]azepine

Following a procedure similar to that described in Preparation 3(b), but using ethyl (R)-(1,2,3,4,10,14b-hexahydrodibenzo[c,f]pyrazino[1,2-a]azepin-2-yl)carboxylate, the title compound was obtained in a 95% yield, melting at 122°-124° C.

PREPARATION 5 $[\alpha]_D^{25}-255°$ (c=1.0, methanol).

(S)-1,2,3,4,10,14b-Hexahydrodibenzo[c,]pyrazino[1,2-a]azepine and (R)-1,2,3,4,10,14b-Hexahydrodibenzo[c,f]pyrazino[1,2-a]azepine 12.01 g of α-methoxy-α-(trifluoromethyl)phenylacetic acid chloride were added dropwise to a solution of 10.81 g of the racemate of 1,2,3,4,10,14b-hexahydrodibenzo[c,f]pyrazino[1,2-a]azepine and 8.77 g of triethylamine in 90 ml of chloroform whilst stirring and ice-cooling, over a period of 15 minutes, and then the mixture was stirred at 0°-5° C. for 1 hour. At the end of this time, water was added to the mixture, which was then extracted with chloroform. Evaporation of the solvent from the extract gave a residue. This residue was subjected to column chromatography through silica gel eluted with a 1:19 by volume mixture of ethyl acetate and hexane, to give 8.39 g (yield 42%) of a less polar substance as colorless needles, melting at 59°161° C., and 9.06 g (yield 45%) of a more polar substance as colorless prisms, melting at 224°-227° C.

$[\alpha]_D^{25}+171°$ (c=1.0, dimethylformamide) for the less polar substance. $[\alpha]_D^{25}-211°$ (c=1.0, dimethylformamide) for the more polar substance.

23.7 ml of a 1.5M solution of diisobutylaluminum hydride in toluene was added dropwise to a solution of 8.30 g of the less polar substance prepared as described above in 140 ml of toluene at −60° C. over a period of 40 minutes, and the mixture was stirred at the same temperature for 1.5 hours. At the end of this time, a saturated aqueous solution of ammonium chloride was added to the mixture and the temperature was raised to room temperature. The mixture was then filtered and the filtrate was extracted with toluene. The solvent was removed from the extract by evaporation under reduced pressure, and the residue was subjected to column chromatography through silica gel eluted with a 1:19 by volume mixture of methanol and methylene chloride, to give 2.30 g (yield 52%) of (S)-1,2,3,4,10,14b-hexahydrodibenzo[c,f]pyrazino[1,2-a]azepine, melting at 128°-130° C.

$[\alpha]_D^{25}+504°$ (c=1.0, dimethylformamide).

Following the procedure described above, but using 9.00 g of the more polar substance, 3.12 g (yield 65%) of (R)-1,2,3,4,10,14b-hexahydrodibenzo[c,f]pyrazino[1,2-a]azepine, melting at 129°-131° C., were obtained.

Infrared Absorption Spectrum (KBr), $\nu_{max}$ cm$^{-1}$: 1489, 2791, 2898, 3189. $[\alpha]_D^{25}-483°$ (c=1.0, dimethylformamide).

PREPARATION 6

(R)-1,2,3,4,10,14b-Hexahydro-2-methyldibenzo[c,f]pyrazino[1,2-a]azepine and (S)-1,2,3,4,10,14b-Hexahydro-2-methyldibenzo[c,f]pyrazino[1,2-a]azepine A solution of 10.8 g of dibenzoyl-L-tartaric acid in 20 ml of methanol was added to a solution of 15 g of the racemate of 1,2,3,4,10,14b-hexahydro-2-methyldibenzo,[c,f]pyrazino[1,2-a]azepine in 180 ml of methanol. The crystals which precipitated were collected by filtration and dried to give a salt, melting at 186° C. (with decomposition).

$[\alpha]_D^{25}-266°$ (c=1.0, dimethylformamide).

The whole of this salt was suspended in a 10% w/v aqueous solution of potassium carbonate and extracted with ethyl acetate. Evaporation of the solvent from the extract gave 4.62 g (yield 31%) of (R)-1,2,3,4,10,14b-hexahydro-2-methyldibenzo[c,f]pyrazino[1,2-a]azepine.

$[\alpha]_D^{25}-457°$ (c=1.0, methanol).

A solution of 10.8 g of dibenzoyl-D-tartaric acid in 30 ml of methanol was added to a solution of 15 g of the racemate of 1,2,3,4,10,14b-hexahydro-2-methyldibenzo[c,f]pyrazino[1,2-a]azepine in 270 ml of methanol. The crystals which precipitated were collected by filtration and dried to give a salt, melting at 186° C. (with decomposition).

$[\alpha]_D^{25}+243°$ (c=1.0, dimethylformamide).

The whole of this salt was suspended in a 10% w/v aqueous solution of potassium carbonate and extracted with ethyl acetate. Evaporation of the solvent from the extract gave 4.79 g (yield 32%) of (S)-1,2,3,4,10,14b-hexahydro-2-methyldibenzo[c,f]pyrazino[1,2-a]azepine.

$[\alpha]_D^{25}+469°$ (c=1.0, methanol).

PREPARATION 7

(R)-1,2,3,4,10,14b-Hexahydro-2-methyldibenzo[c,f-]pyrazino[1,2-a]azepine and
(S)-1,2,3,4,10,14b-Hexahydro-2-methyldibenzo[c,f]pyrazino[1,2-a]azepine A solution of 2.66 g of diacetyl-L-tartaric acid in 20 ml of ethanol were added to a solution of 5 g of the racemate of 1,2,3,4,10,14b-hexahydro-2-methyldibenzo[c,f]pyrazino[1,2-a]azepine in 180 ml of ethanol. The crystals which precipitated were collected by filtration and dried to give a salt, melting at 188°–189° C. (with decomposition).

$[\alpha]_D^{25} -274°$ (c=1.0, dimethylformamide).

The whole of this salt was recrystallized from methanol, suspended in a 10% w/v aqueous solution of potassium carbonate and extracted with ethyl acetate. Evaporation of the solvent from the extract gave 1.5 g (yield 30%) of (R)-1,2,3,4,10,14b-hexahydro-2-methyldibenzo[c,f]pyrazino[1,2-a]azepine.

$[\alpha]_D^{25} -477°$ (c=1.0, methanol).

The mother liquors obtained from recrystallization of the above salts were evaporated and the residues were treated with potassium carbonate as above to give 2.73 g of an (R) and (S) mixture of 1,2,3,4,10,14b-hexahydro2-methyldibenzo[c,f]pyrazino[1,2-a]azepine. The mixture and 2.27 g of the racemate of 1,2,3,4,10,14b-hexahydro2-methyldibenzo[c,f]pyrazino[1,2-a]azepine were combined and dissolved in 180 ml of ethanol. A solution of 2.66 g of diacetyl-D-tartaric acid in 20 ml of ethanol was added to the solution. The crystals which precipitated were collected by filtration and dried to give a salt, melting at 189°–190° C. (with decomposition).

$[\alpha]_D^{25} +250°$ (c=1.0, dimethylformamide).

The whole of this salt was recrystallized from methanol and treated with aqueous potassium carbonate in a similar manner to that described above to give 1.65 g (yield 33%) of (S)-1,2,3,4,10,14b-hexahydro-2-methyldibenzo[c,f]pyrazino[1,2-a]azepine.

$[\alpha]_D^{25} +467°$ (c=1.0, methanol).

TEST EXAMPLE 1

Inhibitory effect on passive cutaneous anaphylaxis (PCA) in rats

According to Mota's method [I. Mota, Immunology, 7, 681–699 (1964)], antiserum (256 times the PCA titer) of rat against egg albumin was prepared and diluted four times with physiological saline. Male SD rats (5 weeks old) were used as the test animals in groups, each containing 4 animals. The rats were sensitized by intradermal injection of 0.05 ml of the diluted antiserum solution in the dorsal position. 48 hours after this injection, a suspension of the test compound in an aqueous 0.5% w/v tragacanth solution was orally administered to the rats, fasted for one day, and 60 minutes later they were injected in the caudal vein with 5 ml/kg body weight of physiological saline containing 0.4% w/v egg albumin and 1.0% w/v Evans Blue. 30 minutes after this last injection, the rats were sacrificed with carbon dioxide and the Evans Blue exuded in the dorsal intradermal portion was determined according to Harada's method (Harada et al., J. Pharm. Pharmac., 23, 218–219 (1971)].

The results achieved from the rest groups which were treated with a test compound were evaluated to determine the inhibitory rate by comparison with the average amount of exuded dye in a control group, which was not given the test compound.

The inhibitory rate was calculated by the following equation.

Inhibitory rate (%)=(1−B/A)×100
A: amount of exuded dye in the control group
B: amount of exuded dye in the test group.

The results are shown in Table 4.

TABLE 4

| Compound of Example No. | Salt | Dose (p.o., mg/kg) | Inhibitory rate (%) |
|---|---|---|---|
| 1 | Oxalate | 3.1 | 65 |
|   |   | 0.2 | 56 |
| 2 | — | 0.8 | 74 |
|   |   | 0.05 | 62 |
| 4 | Oxalate | 3.1 | 63 |
| 5 | Oxalate | 3.1 | 67 |
|   |   | 0.8 | 23 |
| 7 | Oxalate | 12.5 | 72 |
|   |   | 3.1 | 57 |
|   |   | 0.8 | 50 |
| 9 | Oxalate | 3.1 | 63 |
| 10 | Oxalate | 3.1 | 53 |
| 11 | Oxalate | 3.1 | 60 |
|   |   | 0.8 | 49 |
| 16 | — | 3.1 | 63 |
|   |   | 0.8 | 48 |
| 19 | Fumarate | 0.2 | 61 |
|   |   | 0.05 | 55 |
| 24 | Hydrochloride | 3.1 | 74 |
|   |   | 0.05 | 46 |
| 26 | — | 0.2 | 63 |
|   |   | 0.05 | 44 |
| 27 | Hydrochloride | 3.1 | 69 |
| 31 | Hydrochloride | 3.1 | 76 |
|   |   | 0.8 | 32 |
| 59 | Fumarate | 0.2 | 74 |
|   |   | 0.05 | 59 |
| 65 | Hydrate | 0.4 | 58 |
|   |   | 0.05 | 45 |
| Prior art compound D | — | 3.1 | 30 |
| Prior art compound F | — | 3.1 | 52 |
| Prior art compound G* | Sodium | 3.1 | 28 |

*Sodium (1,3,4,14b-tetrehydro-2H, 10H-pyrazino[1,2-a]-pyrrolo[2,1-c][1,4]benzodiazepin-2-yl)acetate Prior art compounds D and F are as previously defined when discussing the prior art.

TEST EXAMPLE 2

Effect on antigen-induced bronchoconstriction in sensitized guinea pigs

The test animals used were male guinea pigs of the Hartley strain (weighing about 400 to 500 g). These animals were sensitized according to Morris' method [H. R. Morris; Br. J. Pharmac. , 67, 179–184 (1979)]. The guinea pigs were subcutaneously and intraperitoneally injected twice, each time with 25 mg of egg albumin (grade 5, Sigma) at weekly intervals. 7 days after the second of these weekly injections, the animals were fasted for one day and then exposed to an aerosol of egg albumin (10 mg/ml). All of the animals so exposed responded with convulsions, indicating respiratory distress due to airway constriction, within 6 minutes.

60 minutes before the egg albumin challenge, one of the test compounds shown in the following. Table 5 was administered orally to each of the animals. The compound was regarded as effective if the animal did not respond with convulsions during the 6 minutes inhalation. The results are shown in Table 5.

TABLE 5

| Compound of Example No. | Salt | Dose (p.o., mg/kg) | Inhibitory rate (%) |
|---|---|---|---|
| 1 | Oxalate | 0.1 | 50 |
|   |   | 0.025 | 20 |
| 2 | — | 0.1 | 80 |
|   |   | 0.025 | 20 |
| 7 | Oxalate | 0.4 | 100 |
| 16 | — | 0.4 | 100 |
|   |   | 0.1 | 60 |
| 18 | — | 0.4 | 100 |
| 19 | Fumarate | 0.4 | 100 |
|   |   | 0.025 | 40 |
| 24 | Hydrochloride | 0.4 | 100 |
|   |   | 0.1 | 80 |
| 26 | — | 0.4 | 80 |
| 59 | Fumarate | 0.05 | 60 |
| 65 | Hydrate | 0.1 | 60 |

We claim:

1. A compound of formula (I):

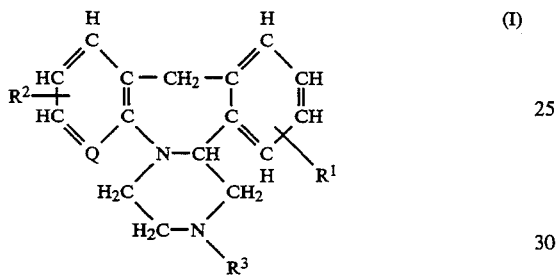

in which:

Q represents a group of formula =CH—;

$R^1$ $R^2$ and are independently selected from the group consisting of hydrogen atoms, alkyl groups having from 1 to 6 carbon atoms, alkoxy groups having from 1 to 6 carbon atoms, hydroxy groups, tri fluoromethyl groups and halogen atoms;

$R^3$ represents:

a substituted alkyl group having from 3 to 7 carbon atoms and having at least one substituent selected from the group consisting of hydroxy groups and groups of formula —COOR$^4$, where $R^4$ represents a hydrogen atom, an alkyl group having from 1 to 6 carbon atoms, an aryl group, as defined below, or an aralkyl group, as defined below;

a group of formula —B—O—D—OR$^4$, where: B represents an alkylene or alkylidene group having from 2 to 4 carbon atoms; D represents an alkylene or alkylidene group having from 2 to 7 carbon atoms or such an alkylene or alkylidene group in which the carbon chain is interrupted by 1 or 2 oxygen atoms; and R$^4$ is as defined above;

a group of formula 'E—O—G—COOR$^4$, where: E represents an alkylene or alkylidene group having from 2 to 7 carbon atoms; G represents a direct carbon-carbon single bond, an alkylene or alkylidene group having from 1 to 9 carbon atoms or such an alkylene or alkylidene group in which the carbon chain is interrupted by 1 or 2 oxygen atoms, said alkylene or alkylidene group being unsubstituted or being substituted by an aryl group; and R$^4$ is as defined above;

a group of formula —E—O—G—CONR$^5$R$^6$, where: E and G are as defined above; and R$^5$ and R$^6$ are independently selected from the group consisting of hydrogen atoms, unsubstituted alkyl groups having from 1 to 6 carbon atoms, substituted alkyl groups which have from 1 to 6 carbon atoms and which have at least one substituent selected from the group consisting of substituents (a), defined below, cycloalkyl groups which have from 3 to 7 ring carbon atoms and which are unsubstituted or have at least one substituent selected from the group consisting of alkyl groups having from 1 to 4 carbon atoms, aryl groups, as defined below, and aralkyl groups, as defined below; or R$^5$ and R$^6$, together with the nitrogen atom to which they are attached, represent a cyclic amino group having from 3 to 6 ring atoms, of which one is said nitrogen atom, optionally having an additional hetero-atom selected from the group consisting of nitrogen, oxygen and sulfur hetero-atoms and the remainder are carbon atoms, said heterocyclic group being unsubstituted or being substituted by at least one substituent selected from the group consisting of substituents (c), defined below; or a group of formula —J—CH(OH)—CH$_2$R$^7$, where: J represents an alkylene or alkylidene group having from 1 to 4 carbon atoms; and R$^7$ represents a hydroxy group, a halogen atom or a group of formula —NR$^5$R$^6$, where R$^5$ and R$^6$ are as defined above;

said aralkyl groups are alkyl groups having from 1 to 4 carbon atoms, which are substituted by 1 to 3 aryl groups, as defined below;

said aryl groups have from 6 to 10 ring carbon atoms and are unsubstituted or have at least one substituent selected from the group consisting of substituents (b), defined below;

substituents (a):

amino groups; alkylamino groups in which the alkyl group has from 1 to 6 carbon atoms; dialkylamino groups in which each alkyl group is independently selected from the group consisting of alkyl groups having from 1 to 6 carbon atoms; and cyclic amino groups having from 3 to 6 ring atoms, of which one is a nitrogen atom, optionally having an additional hetero-atom selected from the group consisting of nitrogen, oxygen and sulfur hetero-atoms and the remainder are carbon atoms, said heterocyclic group being unsubstituted or being substituted by at least one substituent selected from the group consisting of substituents (c), defined below;

substituents (b):

alkyl groups having from 1 to 6 carbon atoms; alkoxy groups having from 1 to 6 carbon atoms; aryl groups, as defined above, provided that they are not themselves substituted by aryl groups; and halogen atoms;

substituents (c):

alkyl groups having from 1 to 4 carbon atoms; aryl groups, as defined above; and aralkyl groups, as defined above;

or a pharmaceutically acceptable salt thereof.

2. The compound of claim 1, wherein R$^1$ represents a hydrogen atom.

3. The compound of claim 1, wherein $R^2$ represents a hydrogen or halogen atom.

4. The compound of claim 1, wherein $R^2$ represents a hydrogen atom.

5. The compound of claim 1, wherein $R^3$ represents an alkyl group having from 3 to 6 carbon atoms which is substituted by a hydroxy group or by a group of formula $-COOR^4$, in which $R^4$ represents a hydrogen atom or an alkyl group having from 1 to 4 carbon atoms.

6. The compound of claim 1, wherein $R^3$ represents a group of formula $-CH_2CH_2OCH_2CH_2OH$ or $-CH_2CH_2OCH_2CH_2OCH_2CH_2OH$.

7. The compound of claim 1, wherein $R^3$ represents a group of formula $-E-O-G-COOR^4$, where:

E represents an alkylene group having from 2 to 6 carbon atoms; G represents an alkylene group having 1 or 2 carbon atoms or a group of formula $-CH_2CH_2OCH_2-$, $-CH_2CH_2OCH_2CH_2-$ or $-CH_2CH_2OCH_2CH_2OCH_2-$; and $R^4$ represents a hydrogen atom or an alkyl group having from 1 to 4 carbon atoms.

8. The compound of claim 1, wherein $R^3$ represents a group of formula $-E-O-G-CONR^5R^6$, where:

E represents an alkylene group having from 2 to 6 carbon atoms;

G represents a single bond, an alkylene group having 1 or 2 carbon atoms or a group of formula $-CH_2CH_2OCH_2-$, $-CH_2CH_2OCH_2CH_2-$ or $-CH_2CH_2OCH_2CH_2OCH_2-$; and $R^5$ and $R^6$ are independently selected from the group consisting of hydrogen atoms, unsubstituted alkyl groups having from 1 to 4 carbon atoms, substituted alkyl groups which have from 1 to 4 carbon atoms and which have at least one substituent selected from the group consisting of cyclic amino groups having 5 or 6 ring atoms, of which one is said nitrogen atom, optionally having an additional hetero-atom selected from the group consisting of nitrogen, oxygen and sulfur hetero-atoms and the remainder are carbon atoms, said heterocyclic group being unsubstituted or being substituted by at least one substituent selected from the group consisting of methyl, ethyl, phenyl, benzyl, benzhydryl, p-chlorobenzhydryl and p,p'-difluorobenzhydryl groups, cycloalkyl groups having from 3 to 7 ring carbon atoms, phenyl groups, which are unsubstituted or which have at least one substituent selected from the group consisting of halogen atoms, methyl groups and methoxy groups, and substituted alkyl groups which have from 1 to 4 carbon atoms, and which are substituted by 1 or 2 phenyl groups, the phenyl groups being unsubstituted or being substituted by at least one substituent selected from the group consisting of halogen atoms, methyl groups and methoxy groups;

or $R^5$ and $R^6$ together with the nitrogen atom to which they are attached, represent a cyclic amino group having 5 or 6 ring atoms, of which one is said nitrogen atom, optionally having an additional hetero-atom selected from the group consisting of nitrogen, oxygen and sulfur hetero-atoms and the remainder are carbon atoms, said heterocyclic group being unsubstituted or being substituted by at least one substituent selected from the group consisting of methyl, ethyl, phenyl, benzyl, benzhydryl, p-chlorobenzhydryl and p,p'-difluorobenzhydryl substituents.

9. The compound of claim 1, wherein $R^3$ represents a group of formula $-CH_2-CH(OH)-CH_2R^7$, where $R^7$ represents a hydroxy group, a halogen atom or a group of formula $-NR^5R^6$, where:

$R^5$ and $R^6$ are independently selected from the group consisting of hydrogen atoms, alkyl groups having from 1 to 4 carbon atoms, cyclopentyl groups, cyclohexyl groups, unsubstituted phenyl groups and substituted phenyl groups having at least one substituent selected from the group consisting of halogen atoms, methyl groups and methoxy groups, or or $R^5$ and $R^6$, together with the nitrogen atom to which they are attached, represent a cyclic amino group having 5 or 6 ring atoms, of which one is said nitrogen atom, optionally having an additional hetero-atom selected from the group consisting of nitrogen, oxygen and sulfur hetero-atoms and the remainder are carbon atoms, said heterocyclic group being unsubstituted or being substituted by at least one substituent selected from the group consisting of methyl, ethyl, phenyl, benzyl, benzhydryl, p-chlorobenzhydryl and p,p'-difluorobenzhydryl substituents.

10. The compound of claim 1, wherein:

Q represents a group of formula $=CH-$;

$R^1$ represents a hydrogen atom;

$R^2$ represents a hydrogen or halogen atom; and $R^3$ represents an alkyl group having from 3 to 6 carbon atoms which is and substituted by a hydroxy group or by a group of formula $-COOR^4$ in which $R^4$ represents a hydrogen atom or an alkyl group having from 1 to 4 carbon atoms.

11. The compound of claim 1, wherein:

Q represents a group of formula $=CH-$;

$R^1$ represents a hydrogen atom;

$R^2$ represents a hydrogen or halogen atom; and $R^3$ represents a group of formula $-CH_2CH_2OCH_2CH_2OH$ or $-CH_2CH_2OCH_2CH_2OCH_2CH_2OH$.

12. The compound of claim 1, wherein:

Q represents a group of formula $=CH-$;

$R^1$ represents a hydrogen atom;

$R^2$ represents a hydrogen or halogen atom; and $R^3$ represents a group of formula $-E-O-G-COOR^4$, where: E represents an alkylene group having from 2 to 6 carbon atoms; G represents an alkylene group having 1 or 2 carbon atoms or a group of formula $-CH_2CH_2OCH_2-$, $-CH_2CH_2OCH_2CH_2-$ or $-CH_2CH_2CH_2OCH_2-$; and $R^4$ represents a hydrogen atom or an alkyl group having from 1 to 4 carbon atoms.

13. The compound of claim 1, wherein:

Q represents a group of formula $=CH-$;

$R^1$ represents a hydrogen atom;

$R^2$ represents a hydrogen or halogen atom; and $R^3$ represents a group of formula $-E-O-G-CONR^5R^6$, where:

E represents an alkylene group having from 2 to 6 carbon atoms;

G represents a single bond, an alkylene group having 1 or 2 carbon atoms or a group of formula $-CH_2CH_2OCH_2-$, $-CH_2CH_2OCH_2CH_2-$ or $-CH_2CH_2OCH_2CH_2OCH_2-$; and $R^5$ and $R^6$ are independently selected from the group consisting of hydrogen atoms, unsubstituted alkyl groups having from 1 to 4 carbon atoms, substituted alkyl groups which have from 1 to 4 carbon atoms and which have at least one substituent selected from the group consisting of cyclic amino groups having 5 or 6 ring atoms, of which one is said nitrogen atom, optionally having an additional hetero-atom selected from the group consisting of nitrogen, oxygen and sulfur hetero-atoms and the remainder are carbon atoms, said heterocyclic group being unsubstituted or being substituted by at least one substituent selected from the group consisting of methyl, ethyl, phenyl, benzyl, benzhydryl, p-chlorobenzhydryl and p,p'-difluorobenzhydryl groups, cycloalkyl groups having from 3 to 7 ring carbon atoms, phenyl groups, which are unsubstituted or which have at least one substituent selected from the group consisting of halogen atoms, methyl groups and methoxy groups, and substituted alkyl groups which have from 1 to 4 carbon atoms, and which are substituted by 1 or 2 phenyl groups, the phenyl groups being unsubstituted or being substituted by at least one substituent selected from the group consisting of halogen atoms, methyl groups and methoxy groups;

or $R^5$ and $R^6$ together with the nitrogen atom to which they are attached, represent a cyclic amino group having 5 or 6 ring atoms, of which one is said nitrogen atom, optionally having an additional hetero-atom selected from the group consisting of nitrogen, oxygen and sulfur hetero-atoms and the remainder are carbon atoms, said heterocyclic group being unsubstituted or being substituted by at least one substituent selected from the group consisting of methyl, ethyl, phenyl, benzyl, benzhydryl, p-chlorobenzhydryl and p,p'-difluorobenzhydryl substituents.

14. The compound of claim 1, wherein:

Q represents a group of formula $=CH-$;

$R^1$ represents a hydrogen atom;

$R^2$ represents a hydrogen or halogen atom; and $R^3$ represents a group of formula $-CH_2-CH(OH)-CH_2R^7$, where $R^7$ represents a hydroxy group, a halogen atom or a group of formula $-NR^5R^6$, where:

$R^5$ and $R^6$ are independently selected from the group consisting of hydrogen atoms, alkyl groups having from 1 to 4 carbon atoms, cyclopentyl groups, cyclohexyl groups, unsubstituted phenyl groups and substituted phenyl groups having at least one substituent selected from the group consisting of halogen atoms, methyl groups and methoxy groups, or $R^5$ and $R^6$, together with the nitrogen atom to which they are attached, represent a cyclic amino group having 5 or 6 ring atoms, of which one is said nitrogen atom, optionally having an additional hetero-atom selected from the group consisting of nitrogen, oxygen and sulfur hetero-atoms and the remainder are carbon atoms, said heterocyclic group being unsubstituted or being substituted by at least one substituent selected from the group consisting of methyl, ethyl, phenyl, benzyl, benzhydryl, p-chlorobenzhydryl and p,p'-difluorobenzhydryl substituents.

15. The compound of claim 1, wherein $R^3$ represents a hydroxyalkyl group having from 3 to 6 carbon atoms.

16. The compound of claim 1, wherein $R^3$ represents an alkyl group having from 3 to 5 carbon atoms which is substituted by a group of formula $-COOR^4$, where:

$R^4$ represents a hydrogen atom or an alkyl group having from 1 to 4 carbon atoms.

17. The compound of claim 1, wherein $R^3$ represents a group of formula $-E-O-G-COOR^4$, where:

E represents an alkylene group having from 2 to 4 carbon atoms;

G represents an alkylene group having 1 or 2 carbon atoms or a group of formula $-CH_2CH_2OCH_2-$ or $-CH_2CH_2OCH_2CH_2OCH_2-$; and $R^4$ represents a hydrogen atom or an alkyl group having from 1 to 4 carbon atoms.

18. The compound of claim 1, wherein $R^3$ represents a group of formula $-E-O-G-CONR^5R^6$, where:

E represents an alkylene group having from 2 to 4 carbon atoms;

G represents a single bond, an alkylene group having 1 or 2 carbon atoms or a group of formula $-CH_2CH_2OCH_2-$ or $-CH_2CH_2OCH_2CH_2OCH_2-$; and $R^5$ and $R^6$ are independently selected from the group consisting of hydrogen atoms, unsubstituted alkyl groups having from 1 to 4 carbon atoms, unsubstituted cycloalkyl groups having from 3 to 7 ring carbon atoms, phenyl groups, which are unsubstituted or have at least one substituent selected from the group consisting of halogen atoms, methyl groups and methoxy groups, and substituted alkyl groups having from 1 to 4 carbon atoms and substituted by an unsubstituted phenyl group or by a substituted phenyl group which itself has at least one substituent selected from the group consisting of methyl, methoxy and halogen substituents.

19. The compound of claim 1, wherein $R^2$ represents a hydrogen, chlorine or fluorine atom, and $R^3$ represents a hydroxyalkyl group having from 3 to 6 carbon atoms.

20. The compound of claim 1, wherein $R^3$ represents an alkyl group having 3 or 5 carbon atoms which is substituted by a group of formula $-COOR^4$, where:

$R^4$ represents a hydrogen atom or an alkyl group having from 1 to 4 carbon atoms.

21. The compound of claim 1, wherein $R^3$ represents a group of formula $-CH_2CH_2-O-CH_2-COOR^4$, where:

$R^4$ represents a hydrogen atom or an alkyl group having from 1 to 4 carbon atoms.

22. The compound of claim 1, wherein $R^3$ represents a group of formula $-CH_2CH_2-O-CH_2-CONR^5R^6$, where:

$R^5$ and $R^6$ are the same or different and each represents a hydrogen atom, an alkyl group having from 1 to 4 carbon atoms, a cycloalkyl group having from 3 to 6 carbon atoms, an unsubstituted phenyl group, a substituted phenyl group having at least one substituent selected from the group consisting of methyl, methoxy, chlorine and fluorine substituents, an unsubstituted benzyl group or a substituted benzyl group having at least one substituent selected from the group consisting of methyl, methoxy, chlorine and fluorine substituents.

23. The compound of claim 1, wherein:
Q represents a group of formula =CH—;
$R^1$ represents a hydrogen atom;
$R^2$ represents a hydrogen or halogen atom; and
$R^3$ represents a hydroxyalkyl group having from 3 to 6 carbon atoms.

24. The compound of claim 1, wherein:
Q represents a group of formula =CH—;
$R^1$ represents a hydrogen atom;
$R^2$ represents a hydrogen or halogen atom; and
$R^3$ represents an alkyl group having 3 or 5 carbon atoms which is substituted by a group of formula —COOR$^4$, where:
$R^4$ represents a hydrogen atom or an alkyl group having from 1 to 4 carbon atoms.

25. The compound of claim 1, wherein:
Q represents a group of formula =CH—;
$R^1$ represents a hydrogen atom;
$R^2$ represents a hydrogen or halogen atom; and
$R^3$ represents a group of formula —CH$_2$CH$_2$—O—CH$_2$—COOR$^4$, where:
$R^4$ represents a hydrogen atom or an alkyl group having from 1 to 4 carbon atoms.

26. The compound of claim 1, wherein:
Q represents a group of formula =CH—;
$R^1$ represents a hydrogen atom;
$R^2$ represents a hydrogen or halogen atom; and
$R^3$ represents a group of formula —CH$_2$CH$_2$—O—CH$_2$CONR$^5$R$^6$, where:
$R^5$ and $R^6$ are the same or different and each represents a hydrogen atom, an alkyl group having from 1 to 4 carbon atoms, a cycloalkyl group having from 3 to 6 carbon atoms, an unsubstituted phenyl group, a substituted phenyl group having at least one substituent selected from the group consisting of methyl, methoxy, chlorine and fluorine substituents, an unsubstituted benzyl group or a substituted benzyl group having at least one substituent selected from the group consisting of methyl, methoxy, chlorine and fluorine substituents.

27. The compound of claim 1, selected from the group consisting of 4-(1,2,3,4,10,14b-hexahydrodibenzo[c,f]pyrazino[1,2-a]azepin-2-yl)butanoic acid or a pharmaceutically acceptable salt thereof.

28. The compound of claim 1, selected from the group consisting of 6-(1,2,3,4,10,14b-hexahydrodibenzo[c,f]pyrazino[1,2-a]azepin-2-yl)hexanoic acid or a pharmaceutically acceptable salt thereof.

29. The compound of claim 1, selected from the group consisting of methyl 4-(1,2,3,4,10,14b-hexahydrodibenzo[c,f]pyrazino[1,2-a]azepin-2-yl)butanoate or a pharmaceutically acceptable salt thereof.

30. The compound of claim 1, selected from the group consisting of ethyl 4-(1,2,3,4,10,14b-hexahydrodibenzo[c,f]pyrazino[1,2-a]azepin-2-yl)butanoate or a pharmaceutically acceptable salt thereof.

31. The compound of claim 1, selected from the group consisting of ethyl 6-(1,2,3,4,10,14b-hexahydrodibenzo[c,f]pyrazino[1,2-a]azepin-2-yl)hexanoate or a pharmaceutically acceptable salt thereof.

32. The compound of claim 1, selected from the group consisting of 2-(1,2,3,4,10,14b-hexahydrodibenzo[c,f]pyrazino[1,2-a]azepin-2-yl)ethoxyacetic acid or a pharmaceutically acceptable salt thereof.

33. The compound of claim 1, selected from the group consisting of ethyl 2-(1,2,3,4,10,14b-hexahydrodibenzo[c,f]pyrazino[1,2-a]azepin-2-yl)ethoxyacetate or a pharmaceutically acceptable salt thereof.

34. The compound of claim 1, selected from the group consisting of 2-(1,2,3,4,10,14b-hexahydrodibenzo[c,f] pyrazino[1,2-a]azepin-2-yl)ethoxyacetamide or a pharmaceutically acceptable salt thereof.

35. The compound of claim 1, selected from the group consisting of α-[2-(1,2,3,4,10,14b-hexahydrodibenzo[c,f]pyrazino[1,2-a]azepin-2-yl)ethoxy]-N,N-dipropylacetamide or a pharmaceutically acceptable salt thereof.

36. The compound of claim 1, selected from the group consisting of ethyl 4-(8-chloro-1,2,3,4,10,14b-hexahydrodibenzo[c,f]pyrazino[1,2-a]azepin-2-yl)butanoate or a pharmaceutically acceptable salt thereof.

37. The compound of claim 1, selected from the group consisting of ethyl 4-(8-fluoro-1,2,3,4,10,14b-hexahydrodibenzo[c,f]pyrazino[1,2-a]azepin-2-yl)butanoate or a pharmaceutically acceptable salt thereof.

38. The compound of claim 1, selected from the group consisting of 4-(8-fluoro-1,2,3,4,10,14b-hexahydrodibenzo[c,f]pyrazino[1,2-a]azepin-2-yl)butanoic acid or a pharmaceutically acceptable salt thereof.

39. A pharmaceutical composition for the treatment or prophylaxis of asthma and allergies, which comprises an effective amount of an active compound in admixture with a pharmaceutically acceptable carrier or diluent, wherein the active compound is at least one compound of formula (I) or a pharmaceutically acceptable salt thereof, as defined in claim 1.

40. The composition of claim 39, wherein said active compound is selected from the group consisting of:
4-(1,2,3,4,10,14b-hexahydrodibenzo[c,f]pyrazino[1,2-a]azepin-2-yl)butanoic acid;
6-(1,2,3,4,10,14b-hexahydrodibenzo[c,f]pyrazino[1,2-a]azepin-2-yl)hexanoic acid;
methyl 4-(1,2,3,4,10,14b-hexahydrodibenzo[c,f]pyrazino[1,2-a]azepin-2-yl)butanoate;
ethyl 4-(1,2,3,4,10,14b-hexahydrodibenzo[c,f]pyrazino[1,2-a]azepin-2-yl)butanoate;
ethyl 6-(1,2,3,4,10,14b-hexahydrodibenzo[c,f]pyrazino[1,2-a]azepin-2-yl)hexanoate;
2-(1,2,3,4,10,14b-hexahydrodibenzo[c,f]pyrazino[1, 2-a]azepin-2-yl)ethoxyacetic acid;
ethyl 2-(1,2,3,4,10,14b-hexahydrodibenzo[c,f]pyrazino[1,2-a]azepin-2-yl)ethoxyacetate;
2-(1,2,3,4,10,14b-hexahydrodibenzo[c,f]pyrazino[1,2-a]azepin-2-yl)ethoxyacetamide;
α-[2-(1,2,3,4,10,14b-hexahydrodibenzo[c,f-]pyrazino[1,2-a]azepin-2-yl)ethoxy]-N,N-dipropylacetamide;
ethyl 4-(8-chloro-1,2,3,4,10,14b-hexahydrodibenzo[c,f-]pyrazino[1,2-a]azepin-2-yl)butanoate;
ethyl 4-(8-fluoro-1,2,3,4,10,14b-hexahydrodibenzo[c,f-]pyrazino[1,2-a]azepin-2-yl)butanoate;
4-(8-fluoro-1,2,3,4,10,14b-hexahydrodibenzo[c,f-]pyrazino[1,2-a]azepin-2-yl)butanoic acid;
or a pharmaceutically acceptable salt thereof.

41. A method for the treatment or prophylaxis of asthma or allergies in a mammal suffering from or susceptible to asthma or allergies, which method comprises administering to said mammal an effective amount of an active compound, wherein the active compound is at least one compound of formula (I) or a pharmaceutically acceptable salt thereof, as defined in claim 1.

42. The method of claim 41, wherein said active compound is selected from the group consisting of:

4-(1,2,3,4,10,14b-hexahydrodibenzo[c,f]pyrazino[1,2-a]azepin-2-yl)butanoic acid;

6-(1,2,3,4,10,14b-hexahydrodibenzo[c,f]pyrazino[1,2-a]azepin-2-yl)hexanoic acid;

methyl 4-(1,2,3,4,10,14b-hexahydrodibenzo[c,f]pyrazino[1,2-a]azepin-2-yl)butanoate;

ethyl 4-(1,2,3,4,10,14b-hexahydrodibenzo[c,f]pyrazino[1,2-a]azepin-2-yl)butanoate;

ethyl 6-(1,2,3,4,10,14b-hexahydrodibenzo[c,f]pyrazino[1,2-a]azepin-2-yl)hexanoate;

2-(1,2,3,4,10,14b-hexahydrodibenzo[c,f]pyrazino[1,2-a]azepin-2-yl)ethoxyacetic acid;

ethyl 2-(1,2,3,4,10,14b-hexahydrodibenzo[c,f]pyrazino[1,2-a]azepin-2-yl)ethoxyacetate;

2-(1,2,3,4,10,14b-hexahydrodibenzo[c,f]pyrazino[1,2-a]azepin-2-yl)ethoxyacetamide;

α-[2-(1,2,3,4,10,14b-hexahydrodibenzo[c,f]pyrazino[1,2-a]azepin-2-yl)ethoxy]-N,N-dipropylacetamide;

ethyl 4-(8-chloro-1,2,3,4,10,14b-hexahydrodibenzo[c,f]pyrazino[1,2-a]azepin-2-yl)butanoate;

ethyl 4-(8-fluoro-1,2,3,4,10,14b-hexahydrodibenzo[c,f]pyrazino[1,2-a]azepin-2-yl)butanoate;

4-(8-fluoro-1,2,3,4,10,14b-hexahydrodibenzo[c,f]pyrazino[1,2-a]azepin-2-yl)butanoic acid; or a pharmaceutically acceptable salt thereof.

43. A compound of formula ( I ):

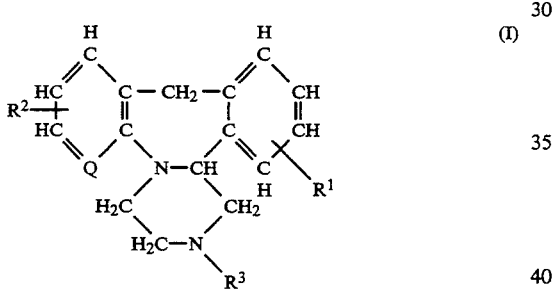

in which:

Q represents a group of formula =CH—; $R^1$ and $R^2$ are hydrogen atoms;

$R^3$ represents:

a substituted alkyl group having from 3 to 7 carbon atoms and having at least one substituent selected from the group consisting of hydroxy groups and groups of formula —COOR$^4$, where R$^4$ represents a hydrogen atom, an alkyl group having from 1 to 6 carbon atoms, an aryl group, as defined below, or an aralkyl group, as defined below;

a group of formula —B—O—D—OR$^4$, where: B represents an alkylene or alkylidene group having from 2 to 4 carbon atoms; D represents an alkylene or alkylidene group having from 2 to 7 carbon atoms or such an alkylene or alkylidene group in which the carbon chain is interrupted by 1 or 2 oxygen atoms; and R$^4$ is as defined above;

a group of formula —E—O—G—COOR$^4$, where: E represents an alkylene or alkylidene group having from 2 to 7 carbon atoms; G represents a direct carbon-carbon single bond, an alkylene or alkylidene group having from 1 to 9 carbon atoms or such an alkylene or alkylidene group in which the carbon chain is interrupted by 1 or 2 oxygen atoms, said alkylene or alkylidene group being unsubstituted or being substituted by an aryl group; and R$^4$ is as defined above; a group of formula —E—O—G—CONR$^5$R$^6$ where: E and G are as defined above; and R$^5$ and R$^6$ are independently selected from the group consisting of hydrogen atoms, unsubstituted alkyl groups from 1 to 6 carbon atoms, substituted alkyl groups which have from 1 to 6 carbon atoms and which have at least one substitutent selected from the group consisting of substituents (a), defined below, cycloalkyl groups which have from 3 to 7 ring carbon atoms and which are unsubstituted or have at least one substituent selected from the group consisting of alkyl groups having from 1 to 4 carbon atoms, aryl groups, as defined below, and aralkyl groups, as defined below;

or R$^5$ and R$^6$, together with the nitrogen atom to which they are attached, represent a cyclic amino group having from 3 to 6 ring atoms, of which one is said nitrogen atom, optionally having an additional hetero-atom selected from the group consisting of nitrogen, oxygen and sulfur hetero-atoms and the remainder are carbon atoms, said heterocyclic group being unsubstituted or being substituted by at least one substituent selected from the group consisting of substituents (c), defined below; or a group of formula —J—CH(OH)-CH$_2$R$^7$, where: J represents an alkylene or alkylidene group having from 1 to 4 carbon atoms; and R$^7$ represents a hydroxy group, a halogen atom or a group of formula —NR$^5$R$^6$, where R$^5$ and R$^6$ are as defined above;

said aralkyl groups are alkyl groups having from 1 to 4 carbon atoms, which are substituted by 1 to 3 aryl groups, as defined below;

said aryl groups have from 6 to 10 ring carbon atoms and are unsubstituted or have at least one substituent selected from the group consisting of substituents (b), defined below;

substituents (a):

amino groups; alkylamino groups in which the alkyl group has from 1 to 6 carbon atoms; dialkylamino groups in which each alkyl group is independently selected from the group consisting of alkyl groups having from 1 to 6 carbon atoms; and cyclic amino groups having from 3 to 6 ring atoms, of which one is a nitrogen atom, optionally having an additional hetero-atom selected from the group consisting of nitrogen, oxygen and sulfur hetero-atoms and the remainder are carbon atoms, said heterocyclic group being unsubstituted or being substituted by at least one substituent selected from the group consisting of substituents (c), defined below;

substituents (b):

alkyl groups having from 1 to 6 carbon atoms; alkoxy groups having from 1 to 6 carbon atoms; aryl groups, as defined above, provided that they are not themselves substituted by aryl groups; and halogen atoms;

substituents (c):

alkyl groups having from 1 to 4 carbon atoms; aryl groups, as defined above; and aralkyl groups, as defined above; or a pharmaceutically acceptable salt thereof.

44. The compound of claim 43, wherein $R^3$ represents an alkyl group having from 3 to 6 carbon atoms which is substituted by a hydroxy group or by a group of formula —COOR$^4$, in which $R^4$ represents a hydrogen atom or an alkyl group having from 1 to 4 carbon atoms.

45. The compound of claim 43, wherein $R^3$ represents a group of formula —CH$_2$CH$_2$OCH$_2$CH$_2$OH or —CH$_2$CH$_2$OCH$_2$CH$_2$OCH$_2$CH$_2$OH.

46. The compound of claim 43, wherein $R^3$ represents a group of formula —E—O—G—COOR$^4$, where:
E represents an alkylene group having from 2 to 6 carbon atoms; G represents an alkylene group having 1 or 2 carbon atoms or a group of formula —CH$_2$CH$_2$OCH$_2$—, —CH$_2$CH$_2$OCH$_2$CH$_2$— or —CH$_2$CH$_2$OCH$_2$CH$_2$OCH$_2$—; and $R^4$ represents a hydrogen atom or an alkyl group having from 1 to 4 carbon atoms.

47. The compound of claim 43, wherein $R^3$ represents a group of formula —E—O—G—CONR$^5$R$^6$ where:
E represents an alkylene group having from 2 to 6 carbon atoms;
G represents a single bond, an alkylene group having 1 or 2 carbon atoms or a group of formula —CH$_2$CH$_2$OCH$_2$—, —CH$_2$CH$_2$OCH$_2$CH$_2$— or —CH$_2$CH$_2$OCH$_2$CH$_2$OCH$_2$—; and
$R^5$ and $R^6$ are independently selected from the group consisting of
hydrogen atoms,
unsubstituted alkyl groups having from 1 to 4 carbon atoms,
substituted alkyl groups which have from 1 to 4 carbon atoms and which have at least one substituent selected from the group consisting of cyclic amino groups having 5 or 6 ring atoms, of which one is said nitrogen atom, optionally having an additional hetero-atom selected from the group consisting of nitrogen, oxygen and sulfur hetero-atoms and the remainder are carbon atoms, said heterocyclic group being unsubstituted or being substituted by at least one substituent selected from the group consisting of methyl, ethyl, phenyl, benzyl, benzhydryl, p-chlorobenzhydryl and p,p'-difluorobenzhydryl groups,
cycloalkyl groups having from 3 to 7 ring carbon atoms,
phenyl groups, which are unsubstituted or which have at least one substituent selected from the group consisting of halogen atoms, methyl groups and methoxy groups, and substituted alkyl groups which have from 1 to 4 carbon atoms, and which are substituted by 1 or 2 phenyl groups, the phenyl groups being unsubstituted or being substituted by at least one substituent selected from the group consisting of halogen atoms, methyl groups and methoxy groups;
or $R^5$ and $R^6$, together with the nitrogen atom to which they are attached, represent a cyclic amino group having 5 or 6 ring atoms, of which one is said nitrogen atom, optionally having an additional hetero-atom selected from the group consisting of nitrogen, oxygen and sulfur hetero-atoms and the remainder are carbon atoms, said heterocyclic group being unsubstituted or being substituted by at least one substituent selected from the group consisting of methyl, ethyl, phenyl, benzyl, benzhydryl, p-chlorobenzhydryl and p,p'-difluorobenzhydryl substituents.

48. The compound of claim 43, wherein $R^3$ represents a group of formula —CH$_2$—CH(OH)—CH$_2$R$^7$, where $R^7$ represents a hydroxy group, a halogen atom or a group of formula —NR$^5$R$^6$, where:
$R^5 R^6$ and are independently selected from the group consisting of hydrogen atoms, alkyl groups having from 1 to 4 carbon atoms, cyclopentyl groups, cyclohexyl groups, unsubstituted phenyl groups and substituted phenyl groups having at least one substituent selected from the group consisting of halogen atoms, methyl groups and methoxy groups, or
or $R^5$ and $R^6$ together with the nitrogen atom to which they are attached, represent a cyclic amino group having 5 or 6 ring atoms, of which one is said nitrogen atom, 0 or 1 is an additional hereto-atom selected from the group consisting of nitrogen, oxygen and sulfur hetero-atoms and the remainder are carbon atoms, said heterocyclic group being unsubstituted or being substituted by at least one substituent selected from the group consisting of methyl, ethyl, phenyl, benzyl, benzhydryl, p-chlorobenzhydryl and p,p'-difluorobenzhydryl substituents.

49. The compound of claim 43, wherein $R^3$ represents a hydroxyalkyl group having from 3 to 6 carbon atoms.

50. The compound of claim 43, wherein $R^3$ represents an alkyl group having from 3 to 5 carbon atoms which is substituted by a group of formula —COOR$^4$, where:
$R^4$ represents a hydrogen atom or an alkyl group having from 1 to 4 carbon atoms.

51. The compound of claim 43, wherein $R^3$ represents a group of formula —E—O—G—COOR$^4$, where:
E represents an alkylene group having from 2 to 4 carbon atoms;
G represents an alkylene group having 1 or 2 carbon atoms or a group of formula —CH$_2$CH$_2$OCH$_2$— or —CH$_2$CH$_2$OCH$_2$CH$_2$OCH$_2$—; and
$R^4$ represents a hydrogen atom or an alkyl group having from 1 to 4 carbon atoms.

52. The compound of claim 43, wherein $R^3$ represents a group of formula —E—O—G—CONR$^5$R$^6$, where:
E represents an alkylene group having from 2 to 4 carbon atoms;
G represents a single bond, an alkylene group having 1 or 2 carbon atoms or a group of formula —CH$_2$CH$_2$OCH$_2$— or —CH$_2$CH$_2$OCH$_2$CH$_2$OCH2—; and
$R^5$ and $R^6$ are independently selected from the group consisting of
hydrogen atoms,
unsubstituted alkyl groups having from 1 to 4 carbon atoms,
unsubstituted cycloalkyl groups having from 3 to 7 ring carbon atoms,
phenyl groups, which are unsubstituted or have at least one substituent selected from the group consisting of halogen atoms, methyl groups and methoxy groups, and
substituted alkyl group having from 1 to 4 carbon atoms and substituted by an unsubstituted phenyl group or by a substituted phenyl group which itself has at least one substituent selected from the group consisting of methyl, methoxy and halogen substituents.

53. The compound of claim 43, wherein $R^2$ represents a hydrogen, chlorine or fluorine atom, and $R^3$ represents a hydroxyalkyl group having from 3 to 6 carbon atoms.

54. The compound of claim 43, wherein $R^3$ represents an alkyl group having 3 or 5 carbon atoms which is substituted by a group of formula —$COOR^4$, where:

$R^4$ represents a hydrogen atom or an alkyl group having from 1 to 4 carbon atoms.

55. The compound of claim 43, wherein $R^3$ represents a group of formula —$CH_2CH_2$—O—$CH_2$—$COOR^4$, where:

$R^4$ represents a hydrogen atom or an alkyl group having from 1 to 4 carbon atoms.

56. The compound of claim 43, wherein $R^3$ represents a group of formula —$CH_2CH_2$—O—$CH_2$—$CONR^5R^6$, where:

$R^5$ and $R^6$ are the same or different and each represents a hydrogen atom, an alkyl group having from 1 to 4 carbon atoms, a cycloalkyl group having from 3 to 6 carbon atoms, an unsubstituted phenyl group, a substituted phenyl group having at least one substituent selected from the group consisting of methyl, methoxy, chlorine and fluorine substituents, an unsubstituted benzyl group or a substituted benzyl group having at least one substituent selected from the group consisting of methyl, methoxy, chlorine and fluorine substituents.

57. A pharmaceutical composition for the treatment or prophylaxis of asthma and allergies, which comprises an effective amount of an active compound in admixture with a pharmaceutically acceptable carrier or diluent, wherein the active compound is at least one compound of formula (I) or a pharmaceutically acceptable salt thereof, as defined in claim 43.

58. A method for the treatment of prophylaxis of asthma or allergies in a mammal suffering from or susceptible to asthma or allergies, which method comprises administering to said mammal an effective amount of an active compound, wherein the active compound is at least one compound of formula (I) or a pharmaceutically acceptable salt thereof, as defined in claim 43.

* * * * *

UNITED STATES PATENT AND TRADEMARK OFFICE
CERTIFICATE OF CORRECTION

PATENT NO. : 5,362,725
DATED : November 8, 1994
INVENTOR(S) : FUKUMI et al

It is certified that error appears in the above-identified patent and that said Letters Patent is hereby corrected as shown below:

Column 5, line 64 delete "Of" and insert --of--.

Column 46, line 25 insert --A-- before "10%".

Column 46, line 27 after "temperature" insert --for 30 minutes. At the end of this time, the solvent--.

Column 46, line 33 delete line entirely and insert --An equimolar amount of fumaric acid was added to a--.

Column 46 between lines 40 and 41 insert --EXAMPLES 60 & 61--.

Column 46, line 51 before "Example" insert --Following a procedure similar to that described in--.

Column 46 between lines 61 and 62 insert --"EXAMPLE 62--.

Column 49 between lines 27 and 28 insert -- PREPARATION 4--.

Column 49, line 46 delete "PREPARATION 5" and insert --PREPARATION 5-- between lines 46 and 47.

UNITED STATES PATENT AND TRADEMARK OFFICE
CERTIFICATE OF CORRECTION

PATENT NO. : 5,362,725

DATED : November 8, 1994

INVENTOR(S) : FUKUMI et al

It is certified that error appears in the above-identified patent and that said Letters Patent is hereby corrected as shown below:

Column 53, line 57, claim 1 delete " 'E- " and insert -- -E- --.

Signed and Sealed this

Ninth Day of April, 1996

*Attest:*

BRUCE LEHMAN

*Attesting Officer*     *Commissioner of Patents and Trademarks*